(12) United States Patent
Yuan et al.

(10) Patent No.: US 12,213,955 B2
(45) Date of Patent: Feb. 4, 2025

(54) COMPOSITIONS AND METHODS FOR BROAD-SPECTRUM ANTIVIRAL THERAPY

(71) Applicant: VERSITECH LIMITED, Telegraph Bay (HK)

(72) Inventors: Shuofeng Yuan, Shek Tong Tsui (HK); Fuk Woo Jasper Chan, Kowloon (HK); Hin Chu, Sai Ying Pun (HK); Johnson Yiu-Nam Lau, Houston, TX (US); Kwok Yung Yuen, Pok Fu Lam (HK)

(73) Assignee: VERSITECH LIMITED, Hong Kong (CN)

( * ) Notice: Subject to any disclaimer, the term of this patent is extended or adjusted under 35 U.S.C. 154(b) by 125 days.

(21) Appl. No.: 16/757,312

(22) PCT Filed: Oct. 16, 2018

(86) PCT No.: PCT/US2018/056138
§ 371 (c)(1),
(2) Date: Apr. 17, 2020

(87) PCT Pub. No.: WO2019/079339
PCT Pub. Date: Apr. 25, 2019

(65) Prior Publication Data
US 2020/0338032 A1  Oct. 29, 2020

Related U.S. Application Data

(60) Provisional application No. 62/573,933, filed on Oct. 18, 2017.

(51) Int. Cl.
*A61K 31/192* (2006.01)
*A61P 31/14* (2006.01)
*A61P 31/16* (2006.01)
*A61P 31/20* (2006.01)

(52) U.S. Cl.
CPC ................ *A61K 31/192* (2013.01)

(58) Field of Classification Search
CPC ..... A61K 31/192; A61K 31/203; A61P 31/12; A61P 31/14; A61P 31/16; A61P 31/18; A61P 31/20; A61P 31/22
See application file for complete search history.

(56) References Cited

U.S. PATENT DOCUMENTS

| 8,536,196 B2 | 9/2013 | Sorensen | |
|---|---|---|---|
| 2004/0152073 A1 | 8/2004 | Herget | |
| 2006/0151574 A1* | 7/2006 | Herget | A61P 31/14 228/101 |
| 2017/0007672 A1* | 1/2017 | Wu | G01N 33/84 |

FOREIGN PATENT DOCUMENTS

| WO | 2008017692 | 2/2008 | |
|---|---|---|---|
| WO | 2013159243 | 10/2013 | |
| WO | 2015138354 | 9/2015 | |
| WO | WO2018/054891 | * 3/2018 | ............. A61K 38/16 |

OTHER PUBLICATIONS

Dawson et al. BMC Immunology 2008, 9, 16, p. 1-14.*
Kapadia et al. PNAS 2005, 102 (7), 2561-2566.*
Radkowski et al. Journal of General Virology 2004, 85, 47-59.*
Hajjou et al. Journal of Medical Virology 2005, 77, 57-65.*
Nguyen et al. J Med Virol. 2017, 89, 1224-1234.*
Altan-Bonnet, "Lipid Tales of Viral Replication and Transmission", Trends Cell Biol., 27(3):201-213 (2017).
Arafa, et al., "Selective agonists of retinoic acid receptors: comparative toxicokinetics and embryonic exposure", Arch. Toxicol., 73(10-11):547-56 (2000).
Burke, et al., "Beta interferon regulation of glucose metabolism is PI3K/Akt dependent and important for antiviral activity against coxsackievirus B3", J. Virol., 88(6): 3485-95 (2014).
Burnum-Johnson, et al., "MPLEx: a method for simultaneous pathogen inactivation and extraction of samples for multi-omics profiling", Analyst, 142(3): 442-448 (2017).
Chan, et al., "Carcinoembryonic Antigen-Related Cell Adhesion Molecule 5 Is an Important Surface Attachment Factor That Facilitates Entry of Middle East Respiratory Syndrome Coronavirus", J. Virol., 90(20): 9114-27 (2016).
Chan, et al., "Middle East respiratory syndrome coronavirus: another zoonotic Betacoronavirus causing SARS-like disease", Clin. Microbiol. Rev., 28(2): 465-522 (2015).
Chan, et al., "Novel antiviral activity and mechanism of bromocriptine as a Zika virus NS2B-NS3 protease inhibitor", Antiviral Res., 141: 29-37 (2017).
Chu, et al., "Middle East Respiratory Syndrome Coronavirus Efficiently Infects Human Primary T Lymphocytes and Activates the Extrinsic and Intrinsic Apoptosis Pathways", J. Infect. Dis., 213(6): 904-14 (2016).
De Clercq, "Strategies in the design of antiviral drugs", Nat. Rev. Drug Discov., 1(1): 13-25 (2002).
De Wilde, et al., "MERS-coronavirus replication induces severe in vitro cytopathology and is strongly inhibited by cyclosporin A or interferon-alpha treatment", J. Gen. Virol., 94(Pt 8):1749-60 (2013).
Di Paolo, et al., "Linking lipids to Alzheimer's disease: cholesterol and beyond", Nat. Rev. Neurosci., 12(5):284-96 (2011).
Dimitrov, "Virus entry: molecular mechanisms and biomedical applications", Nat. Rev. Microbiol., 2(2): 109-22 (2004).

(Continued)

*Primary Examiner* — Irina Neagu
(74) *Attorney, Agent, or Firm* — PABST PATENT GROUP LLP

(57) ABSTRACT

AM580 and structurally related compounds have been found to be useful in treating infection by a wide range of RNA and DNA viruses, and also in reducing associated inflammation. This activity is independent of RAR-α signaling, and is not a result of activation of the hosts innate immune response. Broad antiviral activity of AM580 and structurally related compounds is a due to modulation of lipogenesis so as to correct disregulation of this pathway in virus-infected cells, via inhibition of nSREPBP.

14 Claims, 39 Drawing Sheets

Specification includes a Sequence Listing.

(56) References Cited

OTHER PUBLICATIONS

Dooley, et al., "Sterol regulation of 3-hydroxy-3 methylglutaryl-coenzyme A synthase gene through a direct interaction between sterol regulatory element binding protein and the trimeric CCAAT-binding factor/nuclear factor Y", J. Biol. Chem., 273(3): 1349-56 (1998).
Furuta, et al., "Favipiravir (T-705), a novel viral RNA polymerase inhibitor", Antiviral Res., 100(2): 446-54 (2013).
Goldstein, et al., "Protein sensors for membrane sterols", Cell, 124(1):35-46 (2006).
Goodwin, et al., "Stealing the Keys to the Kitchen: Viral Manipulation of the Host Cell Metabolic Network", Trends Microbiol., 23(12):789-98 (2015).
Graci, et al., "Mechanisms of action of ribavirin against distinct viruses", Rev. Med. Virol., 16(1):37-48 (2006).
Greseth, et al., "De novo fatty acid biosynthesis contributes significantly to establishment of a bioenergetically favorable environment for vaccinia virus infection", PLoS Pathog., 10(3): e1004021 (2014).
Heaton, et al., "Dengue virus nonstructural protein 3 redistributes fatty acid synthase to sites of viral replication and increases cellular fatty acid synthesis", PNAS, 107(40):17345-50 (2010).
Horton, et al., "SREBPs: activators of the complete program of cholesterol and fatty acid synthesis in the liver", J. Clin. Invest., 109(9):1125-31 (2002).
Kaletsky, et al., "Proteolysis of the Ebola virus glycoproteins enhances virus binding and infectivity", J. Virol., 81(24):13378-84 (2007).
Kao, et al., "Identification of influenza A nucleoprotein as an antiviral target", Nat. Biotechnol., 28(6):600-5 (2010).
Kast, et al., "Farnesoid X-activated receptor induces apolipoprotein C-II transcription: a molecular mechanism linking plasma triglyceride levels to bile acids", Molecular Endocrinology, 15(10):1720-1728 (2001).
Kim, et al., "HISAT: a fast spliced aligner with low memory requirements", Nat. Methods, 12(4):357-60 (2015).
Kim, et al., "Nutritional and insulin regulation of fatty acid synthetase and leptin gene expression through ADD1/SREBP1", J. Clin. Invest., 101(1):1-9 (1998).
Kim, et al., "PubChem Substance and Compound databases", Nucleic Acids Res., 44(D1): D1202-13 (2016).
Lands, "Stories about acyl chains", Biochim. Biophys. Acta., 1483(1):1-14 (2000).
Langmead, et al., "Ultrafast and memory-efficient alignment of short DNA sequences to the human genome", Genome Biol., 10(3): R25.1-25.10 (2009).
Lee, et al., "The structure of importin-beta bound to SREBP-2: nuclear import of a transcription factor", Science, 302(5650):1571-5 (2003).
Lorizate, et al., "Role of lipids in virus replication", Cold Spring Harb. Perspect. Biol., 3(10):a004820 (2011).
Magana, et al., "Two tandem binding sites for sterol regulatory element binding proteins are required for sterol regulation of fatty-acid synthase promoter", J. Biol. Chem., 271(51):32689-94 (1996).
Mitchell, et al., "Protein palmitoylation by a family of DHHC protein S-acyltransferases", J. Lipid. Res., 47(6):1118-27 (2006).
Miwako, et al., "Tamibarotene", Drugs Today (Barc.), 43(8):563-8 (2007). Abstract Only.
Mortazavi, et al., "Mapping and quantifying mammalian transcriptomes by RNA-Seq.", Nat. Methods, 5(7):621-8 (2008).
Munger, et al., "Systems-level metabolic flux profiling identifies fatty acid synthesis as a target for antiviral therapy", Nat. Biotechnol., 26(10): 1179-86 (2008).
Noguchi, et al., "Ketogenic essential amino acids modulate lipid synthetic pathways and prevent hepatic steatosis in mice", PLoS One, 5(8): e12057, 14 pages (2010).

Parraga, et al., "Co-crystal structure of sterol regulatory element binding protein 1a at 2.3 A resolution", Structure, 6(5): 661-72 (1998).
Peiris, et al., "Coronavirus as a possible cause of severe acute respiratory syndrome", Lancet, 361(9366):1319-25 (2003).
Qian, et al., "Brain-Region-Specific Organoids Using Mini-bioreactors for Modeling ZIKV Exposure", Cell, 165(5): 1238-1254 (2016).
Sastry, et al., "Protein and ligand preparation: parameters, protocols, and influence on virtual screening enrichments", J. Comput. Aided Mol. Des., 27(3):221-34 (2013).
Sheahan, et al., "Broad-spectrum antiviral GS-5734 inhibits both epidemic and zoonotic coronaviruses", Sci. Transl. Med., 9(396), 20 pages (2017).
Shimano, et al., "Elevated levels of SREBP-2 and cholesterol synthesis in livers of mice homozygous for a targeted disruption of the SREBP-1 gene", J. Clin. Invest., 100(8):2115-24 (1997).
Simmons, et al., "Inhibitors of cathepsin L prevent severe acute respiratory syndrome coronavirus entry", PNAS, 102(33):11876-81 (2005).
Stroganov, et al., "Lead finder: an approach to improve accuracy of protein-ligand docking, binding energy estimation, and virtual screening", J. Chem. Inf. Model, 48(12):2371-85 (2008).
Tam, et al., "Lipidomic profiling of influenza infection identifies mediators that induce and resolve inflammation", Cell, 154(1):213-27 (2013).
Tang, et al., "Inhibition of SREBP by a small molecule, betulin, improves hyperlipidemia and insulin resistance and reduces atherosclerotic plaques", Cell Metab., 13(1):44-56 (2011).
Thakur, et al., "Small-molecule activators of RNase L with broad-spectrum antiviral activity", PNAS, 104(23):9585-90 (2007).
To, et al., "The emergence of influenza A H7N9 in human beings 16 years after influenza A H5N1: a tale of two cities", Lancet Infect Dis, 13(9):809-21 (2013).
Veit, et al., "S-acylation of influenza virus proteins: Are enzymes for fatty acid attachment promising drug targets?", Vaccine, 33(49): 7002-7 (2015).
Warren, et al., "Protection against filovirus diseases by a novel broad-spectrum nucleoside analogue BCX4430", Nature, 508(7496): 402-5 (2014).
Webb, et al., "Inhibition of protein palmitoylation, raft localization, and T cell signaling by 2-bromopalmitate and polyunsaturated fatty acids", J. Biol. Chem., 275(1): 261-70 (2000).
Yang, et al., "The I-TASSER Suite: protein structure and function prediction", Nat. Methods., 12(1):7-8 (2015).
Yuan, et al., "A novel small-molecule compound disrupts influenza A virus PB2 cap-binding and inhibits viral replication", J. Antimicrob. Chemother., 71(9):2489-2497 (2016a).
Yuan, et al., "Identification of a small-molecule inhibitor of influenza virus via disrupting the subunits interaction of the viral polymerase", Antiviral Res., 125:34-42 (2016b).
Yuen, et al., "Clinical features and rapid viral diagnosis of human disease associated with avian influenza A H5N1 virus", Lancet, 351(9101): 467-71 (1998).
Zheng, et al., "Delayed antiviral plus immunomodulator treatment still reduces mortality in mice infected by high inoculum of influenza A/H5N1 virus", PNAS, 105(23): 8091-6 (2008).
Zhou, et al., "Active replication of Middle East respiratory syndrome coronavirus and aberrant induction of inflammatory cytokines and chemokines in human macrophages: implications for pathogenesis", J. Infect. Dis., 209(9):1331-42 (2014).
Zhou, et al., "Human intestinal tract serves as an alternative infection route for Middle East respiratory syndrome coronavirus", Sci. Adv., 3(11): eaao4966, 13 pages (2017).
Zhu, et al., "Broad-spectrum antiviral agents", Front. Microbiol., 6(517), 15 pages (2015).
Zumla, et al., "Coronaviruses—drug discovery and therapeutic options", Nat. Rev. Drug Discov., 15(5):327-47 (2016).
International Search Report for PCT/US2018/056138 dated Feb. 11, 2019.
Yuan, et al., "A novel small-molecule compound disrupts influenza A virus PB2 cap-binding and inhibits viral replication", *J. Antimicrob. Chemother.*, 71(9):2489-2497 (2016).

(56) References Cited

OTHER PUBLICATIONS

Yuan, et al., "Identification of a small-molecule inhibitor of influenza virus via disrupting the subunits interaction of the viral polymerase", *Antiviral Res.*, 125:34-42 (2016).

* cited by examiner

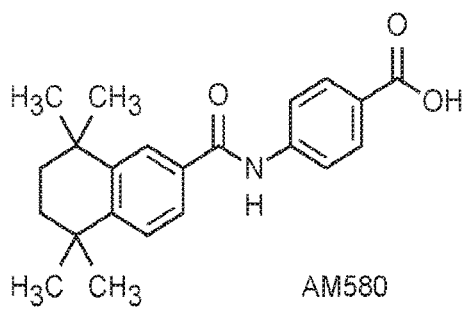
FIG. 1
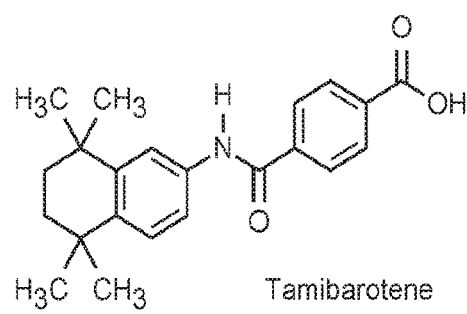
FIG. 2
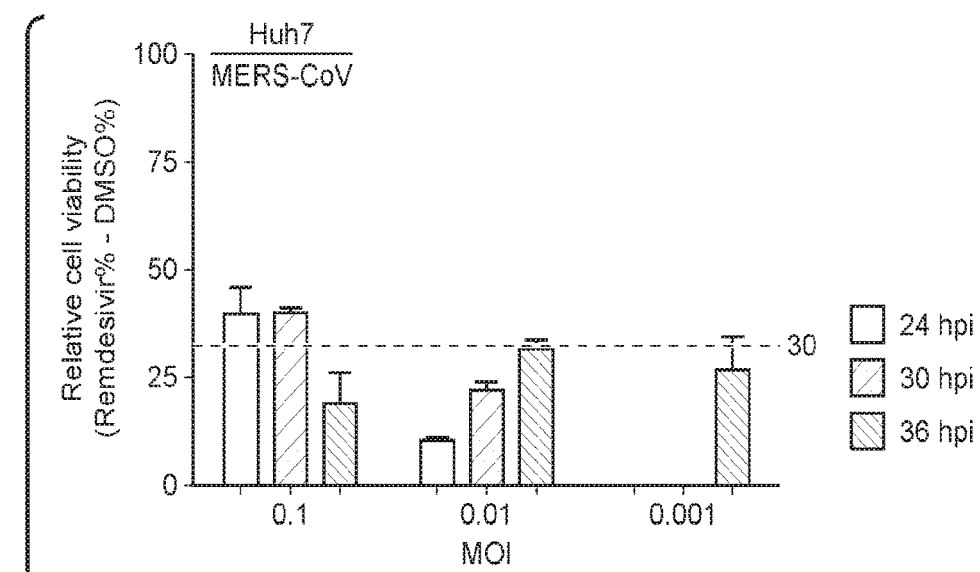
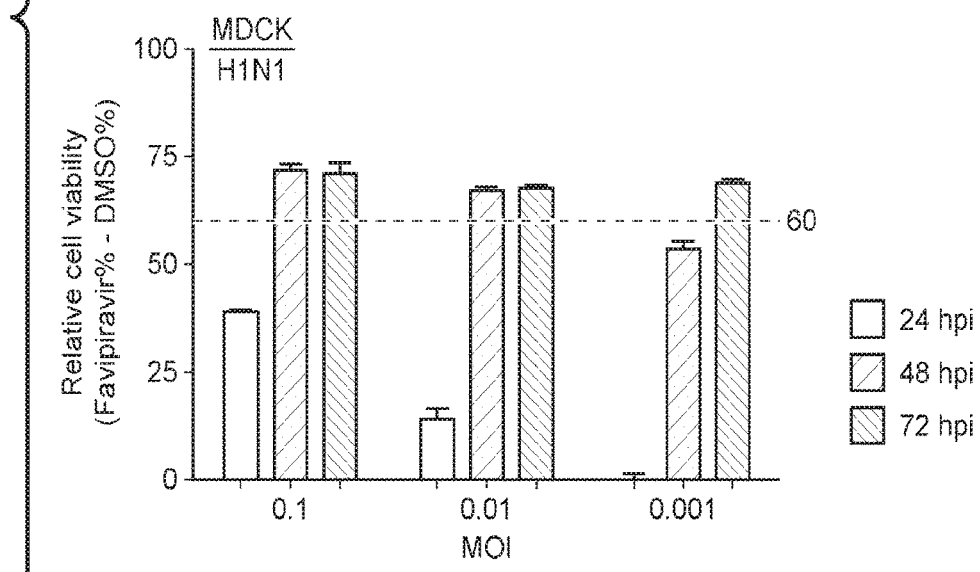
FIG. 3

FIG. 4

| The identified anti-MERS inhibitors | |
|---|---|
| ID | Name |
| 2-E9 | AM580 |
| 2-F10 | 25-hydroxy Vitamin D3 |

| The identified anti-influenza inhibitors | |
|---|---|
| ID | Name |
| 1-E2 | FICZ |
| 1-F2 | C16 Ceramide |
| 2-E9 | AM580 |

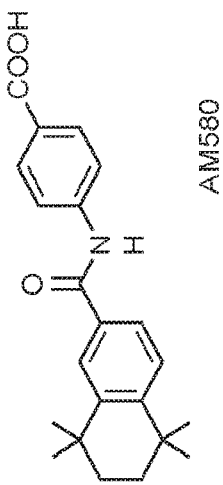
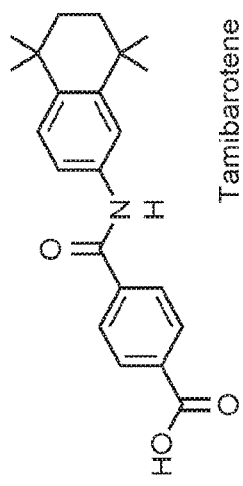
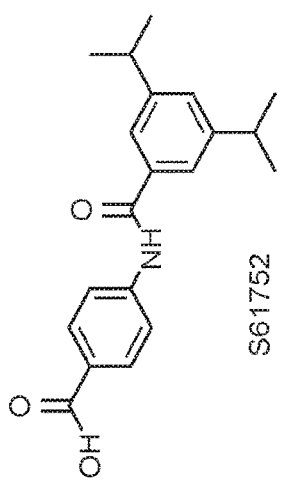
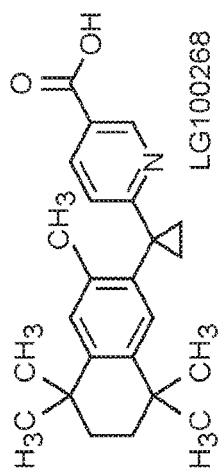
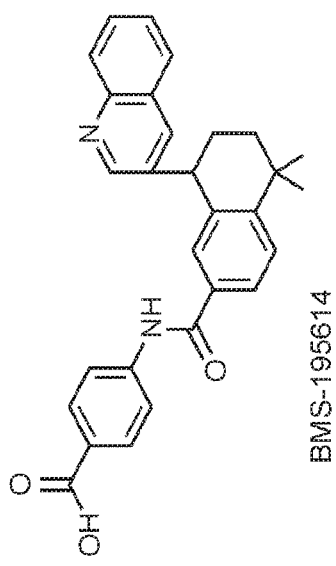
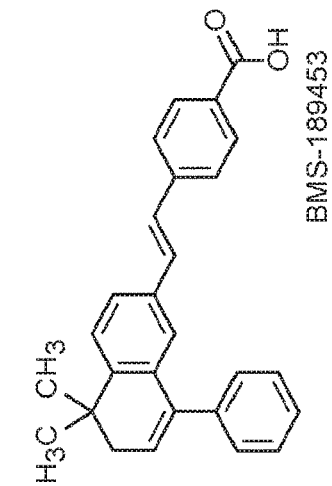
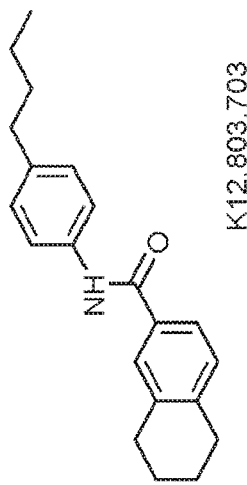
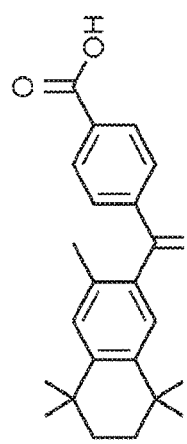
FIG. 15

| Antiviral activity of AM580 | | |
|---|---|---|
| Virus family | Virus | $IC_{50}$ (μM) |
| Coronaviridae | MERS-CoV (HCoV-EMC/2012) | 0.25 ± 0.03 |
| | SARS-CoV (GZ50) | 1.11 ± 0.83 |
| Picornaviridae | EV-A71 (SZ/HK05) | 2.19 ± 1.35 |
| | Human Rhinovirus B | 9.35 ± 2.46 |
| Flaviviridae | ZIKV (PRVABC59) | 5.70 ± 1.08 |
| Orthomyoxoviridae | Influenza A virus (H1N1)pdm09 | 1.34 ± 1.07 |
| Adenoviridae | Human AdV 5 (clinical isolate) | 1.51 ± 0.37 |

Cytotoxicity of AM580

| Cell line | CC$_{50}$ (µM) MTT assay | CC$_{50}$ (µM) CellTiter-Glo assay |
|---|---|---|
| Huh7 | 118.1 ± 1.1 | 106.2 ± 3.1 |
| HEp-2 | 132.6 ± 1.2 | 152.6 ± 6.5 |
| RD | 127.6 ± 3.2 | 117.4 ± 2.1 |
| HEK293T | 115.7 ± 3.2 | 192.1 ± 6.3 |
| Vero | 126.7 ± 1.7 | 135.4 ± 2.9 |
| MDCK | 212.8 ± 12.3 | 142.8 ± 4.1 |

*FIG. 26*

| Virus family | Virus | Select Index (CC$_{50}$/IC$_{50}$) |
|---|---|---|
| Coronaviridae | MERS-CoV (HCoV-EMC/2012) | 507 |
| | SARS-CoV (GZ50) | 114 |
| Picornaviridae | EV-A71 (SZ/HK05) | 58 |
| | HRV-B (clincal isolate) | 14 |
| Flaviviridae | ZIKV (PRVABC59) | 22 |
| Orthomyoxoviridae | Influenza A virus (H1N1)pdm09 | 159 |
| Adenoviridae | Human AdV 5 (clinical isolate) | 51 |

*FIG. 27*

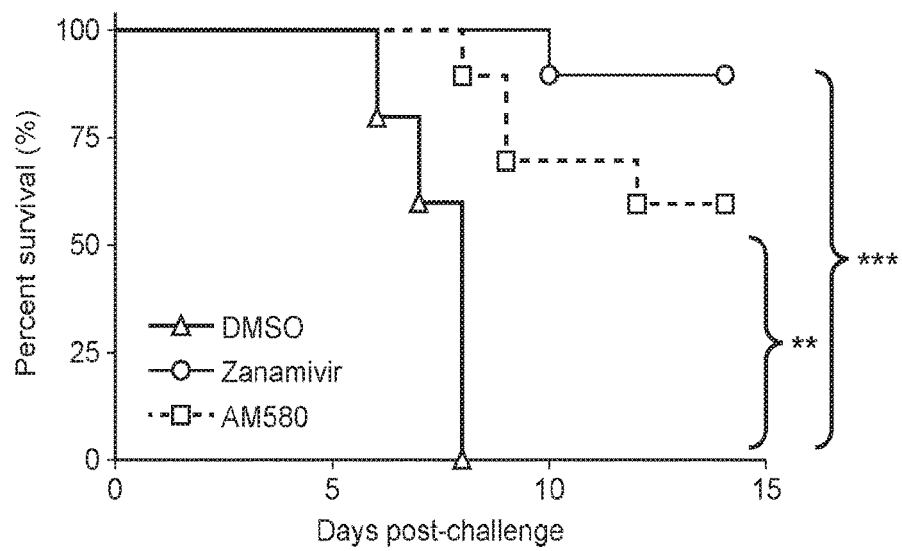

COMPOSITIONS AND METHODS FOR BROAD-SPECTRUM ANTIVIRAL THERAPY

This application claims the benefit of U.S. Provisional Application No. 62/573,933, filed Oct. 18, 2017. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is antiviral therapy, particularly antiviral therapy using small molecules.

BACKGROUND

The background description includes information that may be useful in understanding the present invention. It is not an admission that any of the information provided herein is prior art or relevant to the presently claimed invention, or that any publication specifically or implicitly referenced is prior art.

The epidemic viral diseases of severe acute respiratory syndrome (SARS), pandemic influenza A (H1N1), Middle East respiratory syndrome (MERS), Western/Eastern equine encephalitis (WEE/EEE), Ebola, as well as Zika (ZIKV) occurred in 2003, 2009, 2012, 2013, 2014, and 2016, respectively. These infectious diseases are lethal and transmissible. The high virulence of these viruses and the absence of effective therapies pose an ongoing threat to global public health. The conventional "one-bug-one-drug" paradigm, in which a specific drub is developed to target a specific virus, is insufficient to address the challenge of emerging and re-emerging viral pathogens [1]. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. It is imperative to develop a broad-spectrum class of antiviral agents to manage an effective control of epidemic viral diseases with novel underlying pathogens. Such cross-protective antivirals enable rapid use in patients with viral syndrome when a quick diagnosis is unavailable, which in turn minimize the risks of potential epidemics or pandemics [2].

Current strategies for the development of broad-spectrum antiviral agents primarily focus on two aspects, targeting viral infectivity and modulating the host's defense systems. Successful candidates to reduce viral infectivity are available, including blockers of viral attachment and fusion [3, 4], as well as inhibitors of viral polymerase activities [5]. Due to the evolution of drug-resistance, however, specificity to viral components limits the long-term application of such drugs [6]. Alternatively, type I interferons (IFNs) and IFN-induced proteins trigger the cellular machineries of defense to suppress viral replication. Cellular protein inhibitors and associated pathway modulators intervene with the virus life cycle to restrain the replication fitness [7, 8]. Nevertheless, the challenges of drug toxicity to hosts and generation of resistant viral progenies remain to be addressed. Ribavirin is currently the only FDA-approved drug for broad-spectrum antiviral therapy. However, numerous defects (such as the unfavorable pharmacokinetics and narrow therapeutic windows) restrict its wide application in clinical settings [9].

Viruses are obligatory intracellular parasites. Virus-induced lipid-metabolic reprogramming can substantially impact infectious outcomes, indicating the potential of targeting these processes for broad-spectrum antiviral development [10, 11]. Lipids have long been known as structural elements of viral and cellular membranes. Animal viruses must cross host boundary for cell entry and exit. In enveloped viruses, this occurs by fusion of the incoming virus with, and budding of the nascent virus through a cellular membrane. In nonenveloped viruses, virus entry requires transient disturbance of a cellular (mostly endosomal) membrane to transfer the viral genome into the cytoplasm[12]. Intracellularly, viruses induce cytoplasmic membrane structures and compartments, in which genome replication and assembly occurs. Recently, lipids are emerged as key signaling molecules in eukaryotes, transmitting messages both within and between cells [13].

Thus, there is still a need for safe and effective compounds that effectively treat a broad range of viruses.

SUMMARY OF THE INVENTION

The inventive subject matter provides apparatus, systems and methods in which a—

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1: Structure of AM580.

FIG. 2: Structure of Tamibarotene.

FIG. 3: FIG. 3 depicts results of a study of AM580 as an antiviral. Optimization of MOI conditions and time-points for screening of MERS-CoV inhibitors and for influenza A(H1N1)pdm09 virus inhibitors are shown. Favipiravir (50 μm/ml) and Remdesivir (5 μM) were used as positive controls. Results are normalized by the cell-viability of mock-infected cells.

FIG. 4: FIG. 4 depicts a heatmap showing the library screening for anti-MERS-CoV and/or anti-influenza-virus candidates. Huh7 cells were infected with MERS-CoV (0.1 MOI) and MDCK cells were infected with influenza A(H1N1) virus (0.01 MOI), followed by treatment with bioactive lipid compounds (10 μM) or DMSO vehicle immediately after infection. Cell viability was determined at 24 hpi (for MERS-CoV) and 48 hpi (for influenza-virus), respectively. Normalization was done by setting the DMSO control as 0 and mock-infection as 1. Average from three independent screenings is shown.

FIG. 5 shows anti-MERS-CoV inhibitors identified as identified in FIG. 4.

FIG. 6 shows anti-influenza-virus inhibitors a identified in FIG. 4.

FIG. 7 shows results of studies characterizing anti-MERS-CoV activity of AM580 using a multi-cycle MERS-CoV growth assay. Huh7 cells were infected with 0.001 MOI of MERS-CoV, the inoculum was replaced by 20 μM of AM580 in DMEM medium, at 1 hour after virus infection ("hpi"). Viral titer in the cell culture supernatant was quantified by plaque assay at different time-points as indicated.

FIG. 8 shows results of immunoblot studies characterizing anti-MERS-CoV activity of AM580. Western blotting showed reduced MERS-CoV NP production after AM580 treatment. Huh7 cell lysate was collected at indicated time points after 1 MOI virus infection. β-actin was detected as an internal control and indicator of cell viability.

FIG. 9 shows results of studies flow cytometry studies characterizing anti-MERS-CoV activity of AM580. MERS-CoV-NP positive cells were detected with flow cytometry. Huh7 cells were infected with 0.01 MOI of MERS-CoV. After 24 hours of incubation with AM580 or DMSO control cells were detached, fixed, permeabilized, and stained with anti-MERS-CoV-NP antibodies for flow cytometry. Shown are results of a typical experiment.

FIG. 10 shows results of immunocytochemistry studies characterizing anti-MERS-CoV activity of AM580. Immunofluorescence staining of Huh7 cells representing the MERS-CoV-NP antigen (green), and cell nucleus (blue).

FIG. 11 shows results of viral replication studies characterizing anti-MERS-CoV activity of AM580. AM580 reduced MERS-CoV replication as detected in the cell culture supernatant of A549 (0.1 MOI), Calu-3 (0.1 MOI) and Vero (0.01 MOI) cells at 24 hpi.

FIG. 12 shows results of viral replication studies characterizing anti-MERS-CoV activity of AM580. AM580 reduced MERS-CoV replication as detected in the cell lysate of monocyte-derived macrophage (MDM, 1 MOI) and THP-1 (0.1 MOI) cells at 24 hpi.

FIG. 13 shows results of gene expression analyses of MERS-CoV-infected cells with or without AM580 treatment. AM580 reduced the MERS-CoV induced proinflammatory cytokine up-regulation in Huh7 cells and Monocyte-derived macrophages (MDMs), shown are representative cytokine markers for TNF-α, IL-1β, and IL-8. The difference between MERS-CoV and MERS-CoV treated by AM580 groups were statistically analyzed with the Student's t-test. Error bars represent standard deviations. *$p<0.05$.

FIG. 14 shows the results of antiviral activity and cytotoxicity studies of AM580. Structural-activity analyses of AM580 analogs. Upper panel shows antiviral potency of individual compound at different concentrations (20, 5, 1.25 and 0 μM), lower panel is a summary of their chemical structures and biological functions, respectively.

FIG. 15: FIG. 15 shows the chemical structures of AM580 and select analogs having an $IC_{50}<1$ μM against MERS-CoV infection.

FIG. 16 shows the results studies of anti-MERS-CoV activity of AM580 in organoids. AM580 showed anti-MERS-CoV activity in human intestinal organoid (intestinoid). The differentiated intestinoids were inoculated with MERS-CoV (MOI≈0.1) in triplicate and then re-embedded in Matrigel and maintained in culture medium. At the indicated hpi, intestinoids, cell-free Matrigel, and culture medium were harvested for quantification of viral yield. The dissolved Matrigel and culture medium were applied to viral titration with plaque assay.

FIG. 17 shows the results studies of anti-MERS-CoV activity of AM580 in organoids. AM580 showed anti-MERS-CoV activity in human intestinal organoid (intestinoid). The differentiated intestinoids were inoculated with MERS-CoV (MOI≈0.1) in triplicate and then re-embedded in Matrigel and maintained in culture medium. At the indicated hpi, intestinoids, cell-free Matrigel, and culture medium were harvested for quantification of viral yield. The absolute viral loads in intestinoids were quantified by RT-qPCR and normalized with GAPDH (glyceraldehyde-3-phosphate dehydrogenase) mRNA transcripts.

FIG. 18 shows the results studies of anti-MERS-CoV activity of AM580 in organoids. AM580 showed anti-MERS-CoV activity in human intestinal organoid (intestinoid). The differentiated intestinoids were inoculated with MERS-CoV (MOI≈0.1) in triplicate and then re-embedded in Matrigel and maintained in culture medium. At the indicated hpi, intestinoids, cell-free Matrigel, and culture medium were harvested for quantification of viral yield. At 24 hpi, AM580 (20 μM) or DMSO (0.1%) treated intestinoids, after fixation and immunofluorescence staining of MERS-CoV NP, DAPI and Phalloidin, were whole-mounted and 3D-imaged with a confocal microscope.

FIG. 19 shows the results of immunocytochemistry studies of anti-MERS-CoV of AM580 in lung tissue, with immunofluorescence staining of (MERS-CoV)-infected ex vivo lung tissue for MERS-CoV NP (green). Normal lung tissues were infected with MERS-CoV at $1\times10^8$ PFU per milliliter or subjected to mock infection for 1 hour at 37° C. A total of 18 hours after infection, tissues were fixed, cryoprotected, and cryosectioned. Slides were sequentially stained and confocal images were captured with a Carl Zeiss LSM 800 microscope. Immunoreactivity to NP was detected in epithelial cells of terminal bronchiole (DMSO group). AM580 (20 μM) treatment dramatically reduced MERS-CoV-NP antigen expression.

FIG. 20 shows the results of studies of anti-MERS-CoV activity of AM580 in an animal model. DDP4 transgenic mice (18/group) were treated with AM580 or 0.1% DMSO (placebo control) for 2 days after challenged with 50 PFU of MERS-CoV. Drugs were injected through intraperitoneal route. Survivals and sick signals of the mice were monitored for 14 days or till the mouse death. Differences of survival rates between treated and control groups were compared and analyzed using Log-rank (Mantel-Cox) test, **$p<0.01$.

FIG. 21 shows the results of studies of anti-MERS-CoV activity of AM580 in an animal model. Characterization of anti-MERS-CoV activity of AM580. Daily body weight change of the surviving mice.

FIG. 22 shows the results of studies of anti-MERS-CoV activity of AM580 in an animal model. Four mice from each group were euthanized at days 2 and 4 post-infection and lungs were collected for detection of viral loads using RT-qPCR. Results are presented as mean values+SD. **$p<0.01$ compared with DMSO-treated groups using Student's t-test test.

FIG. 23 shows the results of studies of anti-MERS-CoV activity of AM580 in an animal model. Histopathologic changes in mouse lung tissues collected on days 2 and 4 post-infection. Shown are the representative histologic sections of the lung tissues from the indicated groups with hematoxylin and eosin (H&E) staining.

FIG. 24 summarizes the broad-spectrum antiviral activity of AM580. AM580 showed broad-spectrum antiviral effect against the viruses indicated. Plaque reduction assays were performed to evaluate antiviral activity of AM580 in MERS-CoV and SARS-CoV (Vero-E6 cells), ZIKV (Vero cells), Influenza A H1N1 virus (MDCK cells), and EV71 (RD cells). *Viral load reduction assay was done for AdV5 (Hep-2 cell). Shown are the PFU or viral load of indicated concentrations relative to controls in the absence of compound (%).

FIG. 25 shows the results of antiviral activity and cytotoxicity studies of AM580. The $IC_{50}$ of AM580 against different viruses was determined by plaque reduction assays, with the exception of AdV5 (which was evaluated using a viral load reduction assay).

FIG. 26: FIG. 26 shows the results of antiviral activity and cytotoxicity studies of AM580. The $CC_{50}$ of AM580 in different cell lines was determined by either evaluating cellular NAD(P)H-dependent cellular oxidoreductase enzymes (MTT assay) or ATP activity (CellTiter-Glo assay), respectively.

FIG. 27: FIG. 27 shows the results of antiviral activity and cytotoxicity studies of AM580. The selectivity index ($CC_{50}$/$IC_{50}$) of AM580 antiviral treatment against different viruses is shown.

FIG. 28: FIG. 28 shows the results of studies characterizing the broad-spectrum antiviral activity of AM580 in an animal model. Balb/c mice (18/group) were treated with AM580, zanamivir or 0.1% DMSO for 3 days after challenged with 100 PFU of influenza A (H7N9) virus. Drugs were delivered through intranasal route after anesthesia. Survival rate is shown. Mouse tissue samples were harvested at days 3 and 6 post-infection.

FIG. 29 shows the results of studies characterizing the broad-spectrum antiviral activity of AM580 in an animal model. Balb/c mice (18/group) were treated with AM580, zanamivir or 0.1% DMSO for 3 days after challenged with 100 PFU of influenza A (H7N9) virus. Drugs were delivered through intranasal route after anesthesia. Body weight change is shown. Mouse tissue samples were harvested at days 3 and 6 post-infection.

FIG. 30 shows the results of studies characterizing the broad-spectrum antiviral activity of AM580 in an animal model. Balb/c mice (18/group) were treated with AM580, zanamivir or 0.1% DMSO for 3 days after challenged with 100 PFU of influenza A (H7N9) virus. Drugs were delivered through intranasal route after anesthesia. Lung tissue viral load is shown. Mouse tissue samples were harvested at days 3 and 6 post-infection.

FIG. 31 shows the results of studies characterizing the broad-spectrum antiviral activity of AM580 in an animal model. Balb/c mice (18/group) were treated with AM580, zanamivir or 0.1% DMSO for 3 days after challenged with 100 PFU of influenza A (H7N9) virus. Drugs were delivered through intranasal route after anesthesia. Results of H&E histopathological stain analyses are shown. Mouse tissue samples were harvested at days 3 and 6 post-infection.

FIG. 32 shows the results of studies of the effects of AM580 on RAR-α-signaling or innate antiviral response. Huh7 cells were transfected with RAR-α-targeted siRNA for 24 h, followed by MERS-CoV infection (0.01 MOI) for another 24 h. Viral loads in the cell culture supernatants are shown. Efficiency of siRNA knock-down (KD) was detected by western blotting using β-actin as an internal control. Differences between wild type (mock) and the pretreated (siRNA knockdown or exogenous gene overexpression) were compared.

FIG. 33 shows the results of studies of the effects of AM580 on RAR-α-signaling or innate antiviral response. Huh7 cells were transfected with RAR-α overexpression plasmid for 24 h, followed by MERS-CoV infection (0.01 MOI) for another 24 h. Viral loads in the cell culture supernatants are shown. Overexpression (OE) of RAR-α was detected by western blotting using β-actin as an internal control. Differences between wild type (mock) and the pretreated (siRNA knockdown or exogenous gene overexpression) were compared.

FIG. 34 shows the results of studies of the effects of AM580 on RAR-α-signaling or innate antiviral response. Results of studies with the combined use of an RAR-α antagonist and AM580 did not reduce the antiviral activity.

FIG. 35 shows the results of studies of the effects of AM580 on RAR-α-signaling or innate antiviral response. Results of luciferase assays genetically modified cells carrying genes encoding luciferase-labeled reporting constructs showed that AM580 did not inhibit transactivation of promoters such as TK, CMV and SV40.

FIG. 36 shows the results of studies of the effects of AM580 on RAR-α-signaling or innate antiviral response. Dual-luciferase assays were performed to evaluate the expression of reporter genes as indicated. IFN-β (100 units/ml) was taken as a positive control for the measurement of IFN-β-Luc and ISRE-Luc activities. The concentration of AM580 (20 μM) and DMSO (0.5%) were consistent among the luciferase assays. Results are presented as mean values+SD of two independent experiments.

FIG. 37: FIG. 37 shows the results of studies of the effects of AM580 on RAR-α-signaling or innate antiviral response. AM580 exhibited similar antiviral activity patterns in both WT and RIG-I deficient A549 cells with MERS-CoV infection.

FIG. 38: FIG. 38 shows the results of studies of the affect of AM580 on MERS-CoV entry and internalization. Huh7 cells were treated by the mixture of AM580 (20 μM) and MERS-CoV (2 MOI) for 2 h, following by intensive washes, dissociation from culture plate and subject to flow cytometry analysis of MERS-CoV-NP positive cells.

FIG. 39 shows the results of studies of the effect of AM580 on SREBP-dependent lipid biosynthesis. Lipidomic analyses of MERS-infected cells after AM580 treatment. Shown is the hierarchical clustering analysis based on the identified lipid list. Each bar represents a lipid colored by its average intensities on normalized scale from blue (decreased level) to red (increased level). The dendrogram on the top was constructed based on the lipid intensity.

Figures 40, 41:
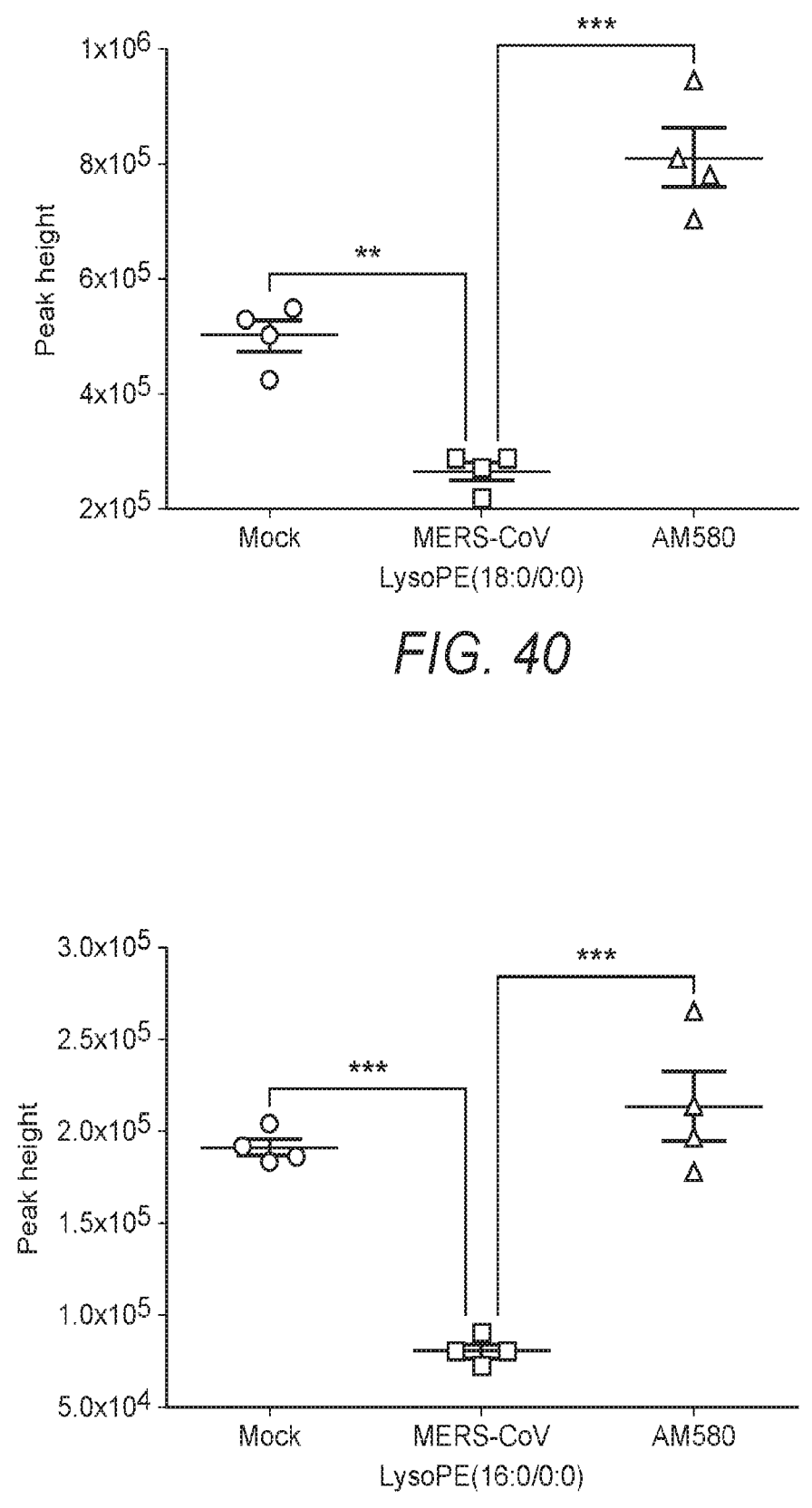

FIG. 40: FIG. 40 shows the peak height of a LysoPE(18:0/0:0) metabolite as shown in FIG. 39. Difference between groups were analyzed by one-way ANOVA test. *$p<0.001$, $p<0.01$, *$p<0.05$.

FIG. 41: FIG. 41 shows the peak height of a LysoPE(16:0/0:0) metabolite as shown in FIG. 39. Difference between groups were analyzed by one-way ANOVA test. *$p<0.001$, $p<0.01$, *$p<0.05$.

FIG. 42 shows the peak height of a LysoPE(16:1/0:0) metabolite as shown in FIG. 39. Difference between groups were analyzed by one-way ANOVA test. *$p<0.001$, $p<0.01$, *$p<0.05$.

FIG. 43 shows the peak height of a LysoPE(18:1/0:0) metabolite as shown in FIG. 39. Difference between groups were analyzed by one-way ANOVA test. *$p<0.001$, $p<0.01$, *$p<0.05$.

FIG. 44 shows the peak height of a PE(P-18:0/0:0) metabolite as shown in FIG. 39. Difference between groups were analyzed by one-way ANOVA test. *$p<0.001$, $p<0.01$, *$p<0.05$.

FIG. 45 shows the peak height of a Lyso-PC(0:0/16:1) metabolite as shown in FIG. 39. Difference between groups were analyzed by one-way ANOVA test. *$p<0.001$, $p<0.01$, *$p<0.05$.

FIG. 46 shows the peak height of a Lyso-PC (16:1/0:0) metabolite as shown in FIG. 39. Difference between groups were analyzed by one-way ANOVA test. *$p<0.001$, $p<0.01$, *$p<0.05$.

FIG. 47 shows the peak height of a PC(18:1/20:1) metabolite as shown in FIG. 39. Difference between groups were analyzed by one-way ANOVA test. *p<0.001, p<0.01, *p<0.05.

FIG. 48 shows the peak height of a PC(20:1/18:3) metabolite as shown in FIG. 39. Difference between groups were analyzed by one-way ANOVA test. *p<0.001, p<0.01, *p<0.05.

FIG. 49 shows the peak height of a PE(38:4) metabolite as shown in FIG. 39. Difference between groups were analyzed by one-way ANOVA test. *p<0.001, p<0.01, *p<0.05.

FIG. 50 shows the peak height of a PE(38:5) metabolite as shown in FIG. 39. Difference between groups were analyzed by one-way ANOVA test. *p<0.001, p<0.01, *p<0.05.

FIG. 51 shows the result of studies of the effect of AM580 on SREBP-dependent lipid biosynthesis. AM580 decreased the cellular lipid droplets (LDs) level. Huh7 cells were infected with MERS-CoV at 0.01 MOI for 24 h, in the presence of 0.1% DMSO, or 20 μM AM580 or mock-infected. Cells were fixed and stained with DAPI and BODIPY 493/503.

FIG. 52 shows the result of studies of the effect of AM580 on SREBP-dependent lipid biosynthesis. AM580 reduced cellular cholesterol level. Huh7 cells were fixed and stained with filipin (blue) that specifically binds free cholesterol.

FIG. 53 shows the results of gene expression analyses of MERS-CoV-infected cells with or without AM580 treatment. The expression of multiple genes in fatty acid synthesis pathways were analyzed by RT-qPCR. The difference between MERS-CoV and MERS-CoV treated by AM580 groups were statistically analyzed with the Student's t-test. Error bars represent standard deviations. *p<0.05.

FIG. 54 shows the results of gene expression analyses of MERS-CoV-infected cells with or without AM580 treatment. The expression of multiple genes in cholesterol synthesis pathways were analyzed by RT-qPCR. The difference between MERS-CoV and MERS-CoV treated by AM580 groups were statistically analyzed with the Student's t-test. Error bars represent standard deviations. *p<0.05.

FIG. 55 shows the results of studies of the effect of siRNA knockdown on viral replication. The siRNA knockdown of either SREBP1 or 2 reduced MERS-CoV replication. Huh7 cells were transfected with 75 nM SREBP1, SREBP2, or scramble control siRNA for two consecutive days. The knockdown efficiency was evaluated with Western blots. siRNA-treated cells were infected with MERS-CoV at 0.01 MOI. After 24 hpi, viral load in the cell culture supernatant was evaluated with qPCR analysis. *p<0.05 when compared with the control siRNA treated group.

FIG. 56 shows the results of AM580 in combination with over-induction of n-SREBP on viral replication. Over-induction of endogenous n-SREBP1 or 2 rescued MERS-CoV replication in the presence of AM580. Huh7 cells were depleted of sterols by incubating in medium containing 5% LPDS and 10 μM mevastatin for 16 h, i.e. starvation. Cells were harvested and lysed to prepare nuclear fractions before detection of n-SREBP1 and n-SREBP2 by Western blots, respectively. Starved cells were infected with MERS-CoV at the indicated MOIs and treated with AM580 (10 μM) for 24 h. Viral load in the cell culture supernatant was quantified with qPCR analysis. Difference between groups with or without starvation treatment was analyzed using Student's t-test.

FIG. 57 shows the results of studies of the effects of n-SREBP processing inhibitors on viral replication. The n-SREBP processing inhibitors PF 429242 and betulin showed anti-MERS-CoV activity. Huh7 cells were infected with MERS-CoV and treated with the compound with indicated concentrations. After 24 h, viral load in the supernatant was analyzed by qPCR *p<0.05 when compared with the 0 μM group.

FIG. 58 shows the effect of AM580 on binding of n-SREBP to SRE. AM580 blocked n-SREBP1 and SRE binding. An SREBP1-specific double stranded DNA (dsDNA) sequence containing the SRE is immobilized onto the wells of a 96-well plate. Huh7 nuclear extraction was added together with positive control competitor dsDNA, betulin (50 μM), or AM580 (20 μM). Bound SREBP-1 was detected according to the manufacturer's protocol. *indicates p<0.05 when compared with the mock control that without drug input.

FIG. 59 shows the effect of AM580 on binding of n-SREBP to SRE. The SREBP2 DNA binding activity assay showed that AM580 inhibited SRE and SREBP2 binding in a dose-dependent manner.

FIG. 60 shows the effect of AM580 on binding of n-SREBP to SRE. AM580 of indicated concentrations were incubated with SRE-immobilized wells for 2 hours, intensively washed before addition of the nuclear extract. Alternatively, AM580 was pre-incubated with equal amount of nuclear extraction for 2 h before adding to the detection wells. AM580 was found to bind to n-SREBP1 rather than SRE.

FIG. 61 shows the results of molecular docking studies of AM580. AM580 was predicted to occupy the SRE recognition sites of both SREBP1 and 2. Shown is the 3D molecular docking analysis. Potential interaction surfaces on SREBPs are red-colored, while AM580 is displayed in stick and mesh representation. Lower panel: partial sequence alignment of the DNA-binding portions of human and mouse SREBP1 and 2. Tyr335, the key residue for AM580 binding highlighted with a box and is shown to be completely conserved.

FIG. 62 shows the results of molecular docking studies of AM580. Docking analysis predicts the key amino acid residues of SREBP1 that interact with AM580.

FIG. 63 shows the results of mutations of n-SREBP1 on AM580 binding. Truncated n-SREBP1 (WT) and its mutant plasmid construct Y335R were transfected to HEK293T cells for 48 h, followed by nuclear extraction and measurement of DNA binding intensity. Differences between WT and Y335R were analyzed with the Student's t test. *p<0.05. Tyr335 was found to be critical for n-SREBP1 binding activity.

FIG. 64 shows the results of studies of the antiviral activity of an AM580 analog. A chemically modified compound AM580, azido-AM580, displayed similar antiviral potency in MERS-CoV infected Vero and Huh7 cells.

FIG. 65 shows the results of fluorescence imaging of cells treated with an AM580 analog. Huh7 cells were treated with azido-AM580 (20 μM) for 6 hours, fixed, permeabilized and immunofluorescence stained with DyLight™ 488-Phosphine, DAPI, and Phalloidin for confocal imaging. AM580 was used as a control due to the lack of a phosphine-specific azido group.

FIG. 66 shows the structure of an AM580-derived photoaffinity probe (AM580dp) showing the localization of designated groups with specific functionalities. Azido-AM580 was achieved through the reaction between azido-PEGS-amine and AM580. AM580dp was synthesized through addition of tri-functional crosslinker 2-{N2-[Nα-benzoylbenzoicamido-N6-6-biotinamidocaproyl]lysinylamido}ethyl-2'-(N sulfosuccinimidylcarboxy) ethyl disulfide sodium salt (Santacruz) with methyl 4-[2-[2-(2-aminoethoxy)ethoxy]ethylcarbamoyl]-2-diphenylphosphanyl-benzoate then with azido-AM580.

FIG. 67 shows the results of affinity binding studies performed using an AM580 analog as shown in FIG. 66. AM580dp was immobilized on streptavidin beads and incubated with the cell lysate that were transfected with either WT or Y335R constructs. After UV exposure to activate the crosslinking (click chemistry), AM580dp-bound protein complex was pulled down by its biotin tag. Western blotting was employed to detect n-SREBP1 using anti-flag and n-SREBP1 specific antibodies, while RAR-α was involved as a positive control protein among the pull-down molecules, while azido-AM580 was used as a negative control to exclude non-specific binding.

FIG. 68 shows the results of studies of transcriptional activation following AM580 treatment. Inhibition of HMGCS and FAS transcriptional activation by AM580 is shown by loss of luciferase activity in cells carrying HMGCS-promoter-Luc and FAS-promoter-Luc reporting constructs and exposed to the drug.

FIG. 69 depicts a schematic diagram showing the n-SREBPs processing, downstream pathways, reported virus families that are affected and control inhibitors used in studies of AM580 effects on lipogenic enzymes.

FIG. 70 shows the results of studies of the effects of AM580 treatment on lipogenesis and viral replication. Huh7 cells infected with MERS-CoV (0.01 MOI) were treated with DMSO (0.1%), or C75 (10 μM), or AM580 (20 μM) in the absence (white bars) or presence (grey bars) of supplemental, exogenous palmitate (100 μM). Viral yield at 24 hpi was shown. Differences between groups were analyzed by one-way ANOVA test. Exogenous palmitate was found to rescue MERS-CoV replication in cells undergoing AM580 treatment.

FIG. 71 shows the results of studies of the effects of AM580 treatment on lipogenesis and viral replication. MDCK cells infected with influenza A (H1N1) (0.001 MOI) were treated with DMSO (0.1%), or C75 (10 μM), or AM580 (20 μM) in the absence (white bars) or presence (red bars) of supplemental, exogenous palmitate (100 μM). Viral yield at 24 hpi was shown. Differences between groups were analyzed by one-way ANOVA test. Exogenous palmitate rescued influenza A (H1N1) virus replication in cells undergoing AM580 treatment.

FIG. 72 shows the results of studies of the effects of AM580 treatment on lipogenesis and viral replication. RD cells infected with EVA-71 (0.001 MOI) were treated with DMSO (0.1%), or C75 (10 μM), or AM580 (20 μM) in the absence (white bars) or presence (blue bars) of supplemental, exogenous palmitate (100 μM). Viral yield at 24 hpi was shown. Differences between groups were analyzed by one-way ANOVA test. Exogenous palmitate rescued EVA-71 virus replication in cells undergoing AM580 treatment.

FIG. 73 shows the results of studies of the effects of AM580 treatment on lipogenesis and viral replication. HEp-2 cells infected with Human AdV5 (0.1 MOI) were treated with DMSO (0.1%), or C75 (10 μM), or AM580 (20 μM) in the absence (white bars) or presence (grey bars) of supplemental, exogenous palmitate (100 μM). Viral yield at 24 hpi was shown. Differences between groups were analyzed by one-way ANOVA test. Exogenous palmitate rescued Human AdV5 virus replication in cells undergoing AM580 treatment.

FIG. 74 shows the results of AM580 treatment on formation of double membrane vesicles ("DMVs"). Vero cells were infected with MERS-CoV and incubated for 18 h with or without AM580. The cell pellets were fixed with glutaraldehyde and processed for electron microscopy. Virus-infected cells without treatment showed perinuclear clusters of DMVs (red box) and the lack of DMVs production upon AM580 treatment (20 μM). Each representative image shown was selected from a pool of over 30 images captured in two separate experiments. AM580 inhibited DMVs formation.

FIG. 75 shows the results of studies of the effect of AM580 treatment on palmitoylation. A549 cells were transfected with HA plasmid from influenza A(H1N1) virus. Drug treatment DMSO (0.1%), or 5 μM 2-BP (positive control inhibitor), or 20 μM AM580 was carried out at 5 hours post-transfection, while cell lysates were harvested 24 hours later. Total HA (input) and palmitoylated HA of different groups were analyzed using Western blotting. β-actin was taken as internal controls. AM580 reduced viral protein palmitoylation.

FIG. 76 shows the results of studies of the effect of 2-BP on viral replication. MDCK cells were infected by influenza A(H1N1) with 0.001 MOI and treated with the compound with indicated nontoxic concentrations. After 24 hpi, viral titer in the supernatant was analyzed by standard plaque assay. 2-BP reduced influenza A(H1N1) virus replication. 2-BP also reduced MERS-CoV replication in Huh7 cells. **p<0.01 when compared with the 0 μM group. All data represents mean and standard deviation from two independent experiments.

DETAILED DESCRIPTION

Figures 5, 6, 7:
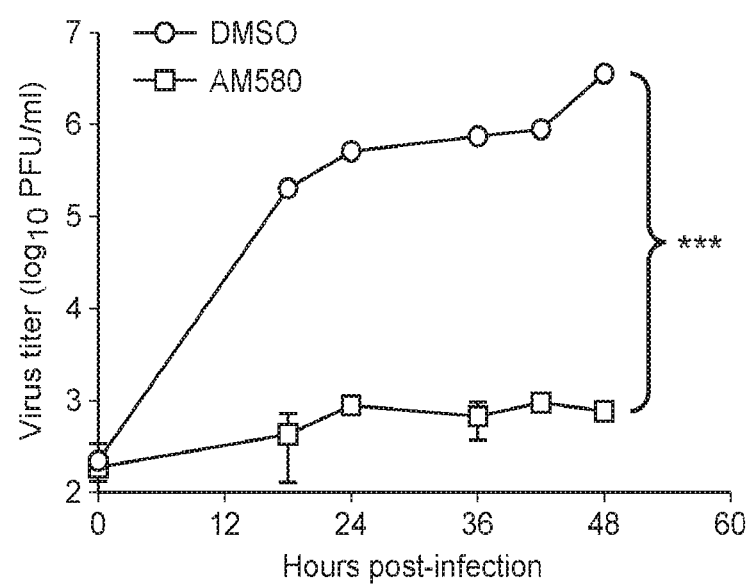
FIG. 5.
FIG. 6.
FIG. 7.

The following description includes information that may be useful in understanding the present invention. It is not an admission that any of the information provided herein is prior art or relevant to the presently claimed invention, or that any publication specifically or implicitly referenced is prior art.

The inventive subject matter provides apparatus, systems and methods in which small molecules that interfere with lipogenesis are utilized to provide broad spectrum antiviral activity, both in vitro and in vivo. The Inventors have found that modulation of cellular lipid metabolism to interfere with virus multiplication can provide a broad-spectrum approach to antiviral therapy. Without wishing to be bound by theory, the Inventors believe that perturbation on the lipogenesis and/or lipid metabolism can diminish and/or reduce virus fitness. Pharmacological screening of a bio-active lipid library can identify potential antiviral inhibitors. For example, AM580 (known as a retinoid derivative, see FIG. 1) was found to provide potent and broad-spectrum antiviral activities in vitro and in vivo. Structure-activity analyses further identified Tamibarotene (FIG. 2), an analog of AM580, as a potent MERS-CoV replication inhibitor. Such compounds can be used in conjunction with other compounds that modulate lipid metabolism and/or antiviral compounds.

Various objects, features, aspects and advantages of the inventive subject matter will become more apparent from the following detailed description of preferred embodiments. The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In some embodiments a broad spectrum antiviral compound can be a retinoid or retinoid derivative. Suitable retinoid derivatives include AM580, Tamibarotene, and/or bexarotene. The formulation can be administered orally, parenterally, by injection, by infusion, and/or by absorption through a mucus membrane. The formulation can be provided as a solution, a suspension, an injectable, a pill, a tablet, a capsule, and/or a suppository. In some embodiments the medication can also include a pharmaceutically acceptable carrier and/or another pharmaceutically active compound. Such a pharmaceutically active compound can be another anti-viral compound, such as ribavarin. In other embodiments the pharmaceutically active compound can have activity against symptoms or sequelae of a viral infection, such as an anti-inflammatory, an anti-emetic, an analgesic, and or an antibiotic.

A synergistic (i.e. greater than additive) effect can be observed when a retinoid derivative of the inventive concept is used in combination with one or more additional pharmaceutically active compounds. For example, effective IC50 equivalents of AM580 and Lopinavir when used in combination against MERS-CoV show an FICI of less than 0.5, indicating the presence of a synergistic effect.

TABLE 1

| Combination Ratio | IC50 Equivalent$^a$ | | |
|---|---|---|---|
| AM580:Lopinavir | AM580 | Lopinavir | FICI$^b$ |
| 10:1 | 0.21 | 0.05 | 0.26* |
| 5:1 | 0.39 | 0.07 | 0.46* |
| 1:1 | 012 | 0.12 | 0.24* |
| 1:5 | 0.09 | 0.34 | 0.43* |
| 1:10 | 0.07 | 0.39 | 0.46* |

$^a$Concentration in IC$_{50}$ equivalent is a normalized concentration calculated by dividing the IC$_{50}$ of the drug in combination by it IC$_{50}$ when used alone.
$^b$FICI is the sum of A580 and Lopinavir IC50-equivalent concentrations used in each combination.
*FICI < 0.50 is considered a significant synergistic effect.

Another embodiment of the inventive concept is method of treating a viral infection by administering a compound that decreases lipogenesis and/or interferes with or otherwise modulates lipid metabolism, and/or using such a compound to formulate a medication that shows broad spectrum (i.e. more than one viral strain or species) anti-viral activity. Susceptible viruses can include MERS-Conarovirus, SARS-Conarovirus, Zika virus, an Influenza A virus (such as Influenza A (H1N1) pdm09, Influenza virus A (H5N1), and Influenza virus A (H7N9)), a Human Adenovirus (such as Human Adenovirus 5), and an Enterovirus (such as EV71). In some embodiments the compound can be a retinoid or retinoid derivative. Suitable retinoid derivatives include AM580, Tamibarotene, and/or bexarotene. The formulation can be administered orally, parenterally, by injection, by infusion, and/or by absorption through a mucus membrane. The formulation can be provided as a solution, a suspension, an injectable, a pill, a tablet, a capsule, and/or a suppository. In some embodiments the medication can also include a pharmaceutically acceptable carrier and/or another pharmaceutically active compound. Such a pharmaceutically active compound can be another anti-viral compound, such as ribavarin. In other embodiments the pharmaceutically active compound can have activity against symptoms or sequelae of a viral infection, such as an anti-inflammatory, an anti-emetic, an analgesic, and or an antibiotic.

In such an embodiment the method can include a dosing schedule that provides the formulation at a dosage and frequency effective to reduce or control a viral infection. Such a dosing schedule can provide the compound that decreases lipogenesis and/or interferes with or otherwise modulates lipid metabolism in amounts ranging from 1 µg/kg body weight to 100 mg/kg body weight per dose. Such a dosing schedule can provide for constant infusion, or can provide periodic dosing. Suitable periodic dosing schedules can provide the formulation at frequencies ranging from every 4 hours to once a week or longer.

One should appreciate that the disclosed techniques provide many advantageous technical effects including provision of a broad spectrum antiviral compound, which can reduce the need for identification of specific viral strains and the subsequent delay in effective treatment.

In one embodiment of the inventive concept a compound that decreases lipogenesis and/or interferes with or otherwise modulates lipid metabolism forms at least part of a formulation that shows broad spectrum (i.e. more than one viral strain or species) anti-viral activity. Susceptible viruses can include MERS-Conarovirus, SARS-Conarovirus, Zika virus, an Influenza A virus (such as Influenza A (H1N1) pdm09, Influenza virus A (H5N1), and Influenza virus A (H7N9)), a Human Adenovirus (such as Human Adenovirus 5), and an Enterovirus (such as EV71). In some embodiments the compound can be a retinoid or retinoid derivative. Suitable retinoid derivatives include AM580, Tamibarotene, and/or bexarotene.

Figure 4:
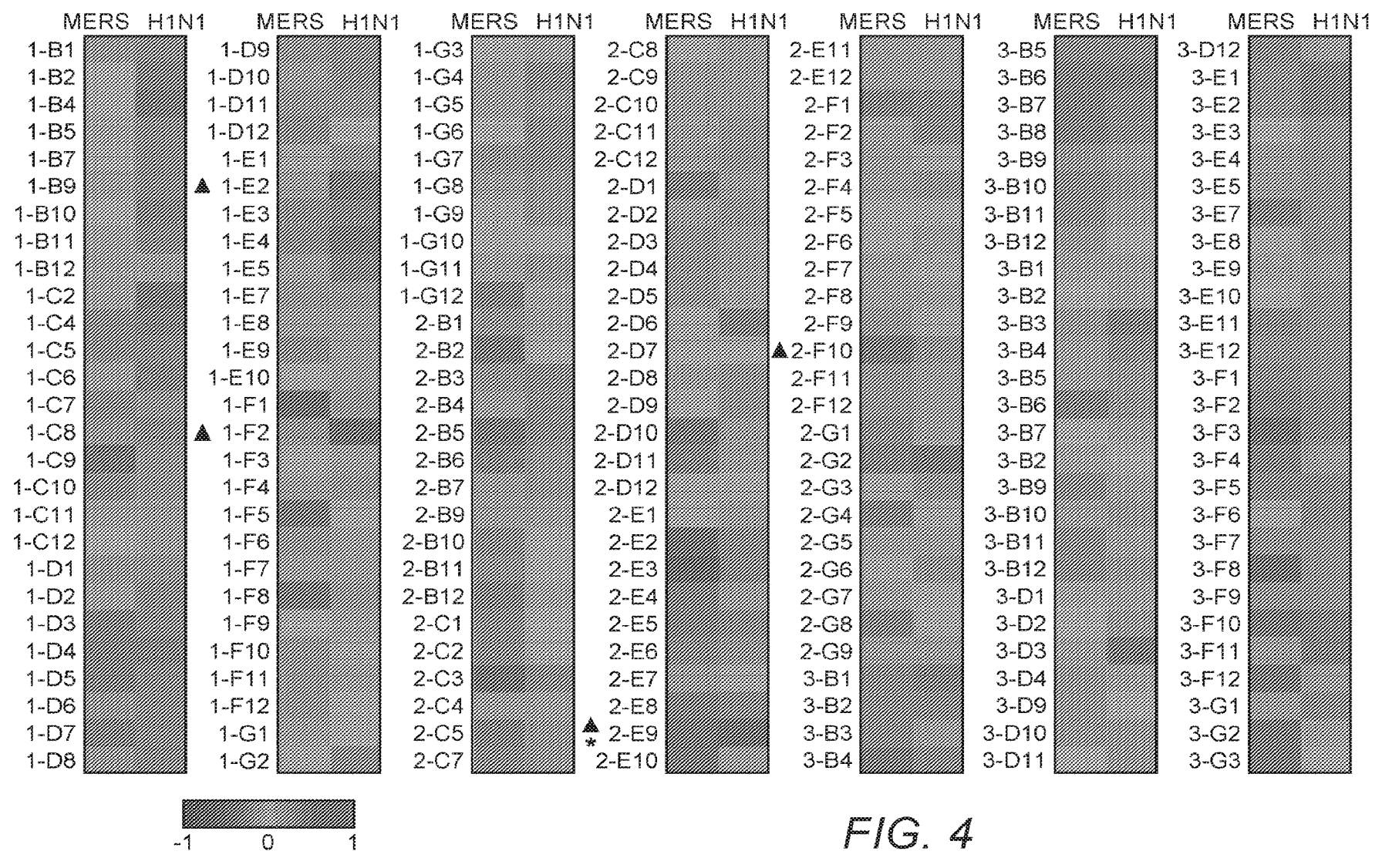

To identify antiviral compounds, Inventors developed colorimetric assays reflecting cell viability that were optimized to screen compounds that can inhibit cytopathic effect (CPE) development upon MERS-CoV and/or influenza A(H1N1)pdm09 virus infection. In order to maximally differentiate cell viability between drug-treated and untreated groups, various combinations of multiplicity of infection (MOI) and time-point of viability checks were evaluated. High MOIs of virus infection can compromise the antiviral activity and shorten the window for drug screening. On the other hand, low MOIs can require multiple rounds of virus replication to differentiate drug efficacies which can in turn result in drug degradation by cell metabolism. Huh7 and MDCK cells were employed as these can robustly support the replication of MERS-CoV and influenza A viruses, respectively. GS5734 (Remdesivir) and T-705 (Favipiravir) were utilized as positive control inhibitors due to their remarkable antiviral potency against coronavirus [20] and influenza A virus [21], respectively. The combination of 0.1 MOI and an end-point at 24 hours post-infection (hpi) was determined to be appropriate for anti-MERS-CoV screening, while for anti-influenza inhibitors was determined as 0.01 MOI and 48 hpi were found to be appropriate (see FIG. 3). Based on the optimized conditions, a library containing 189 bioactive lipids was employed for primary screening, followed by dose-dependent analyses to validate and prioritize candidate compounds (see FIG. 4).

Notably, compound AM580 protected cells against infection by both MERS-CoV and influenza A(H1N1)pdm09 virus. The aryl hydrocarbon receptor (AhR) agonist FICZ and apoptosis regulatory messenger C16 Ceramide specifically protected MDCK cells against influenza A(H1N1)pdm virus infection, while a lipid metabolite 25-Hydroxyvitamin D3 with anti-inflammatory effect protected Huh7 cells against MERS-CoV infection (see FIGS. 5 and 6). AM580 was identified as a compound that exhibited cell protection effects against both viruses, was selected for further characterization.

Figure 8:
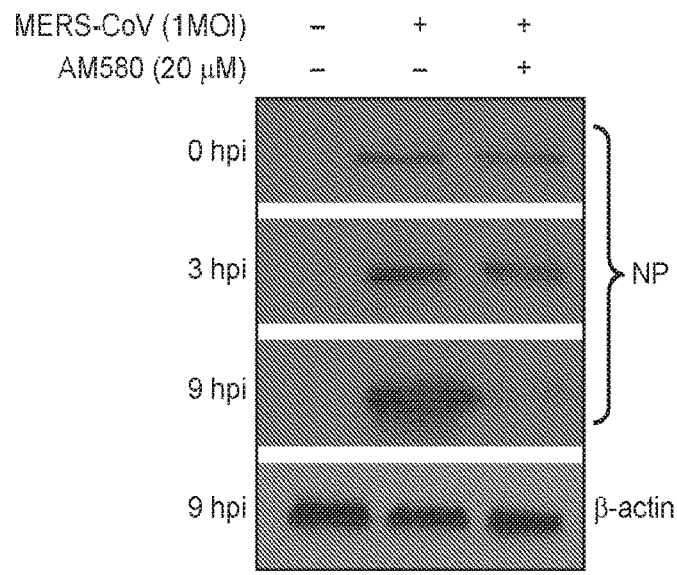
FIG. 8.

Using MERS-CoV infection as a model, Inventors characterized the antiviral activity of AM580 in cell culture. A multi-cycle virus growth assay was performed to plot the virus replication kinetics with or without AM580. At indicated time-points of 18, 24, 36, 42 and 48 hours after infection ("hpi"), AM580 treatment reduced viral titer in the cell supernatant for >3 logs when compared with the DMSO negative control (see FIG. 7). Strikingly, the infectious plaque-forming units (PFU) in the AM580 group were restricted to a baseline level during throughout the entire time course of the study, indicating highly efficient suppression of MERS-CoV by AM580 in initial infection cycles. Furthermore, Western blotting showed that expression of MERS-CoV nucleoprotein (NP) was dramatically decreased upon AM580 addition, particularly at 9 hpi (see FIG. 8).

Figure 9:
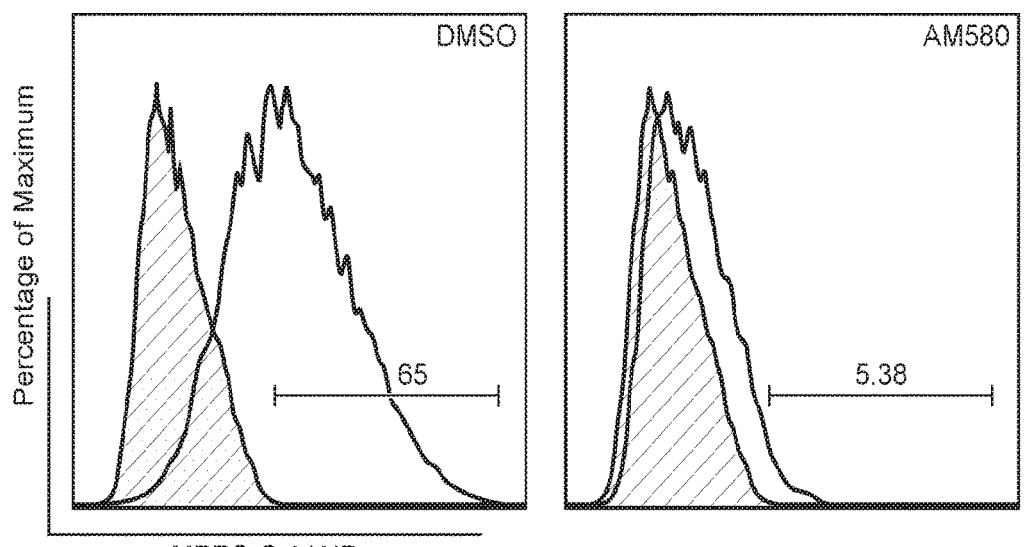
FIG. 9.
Figure 10:
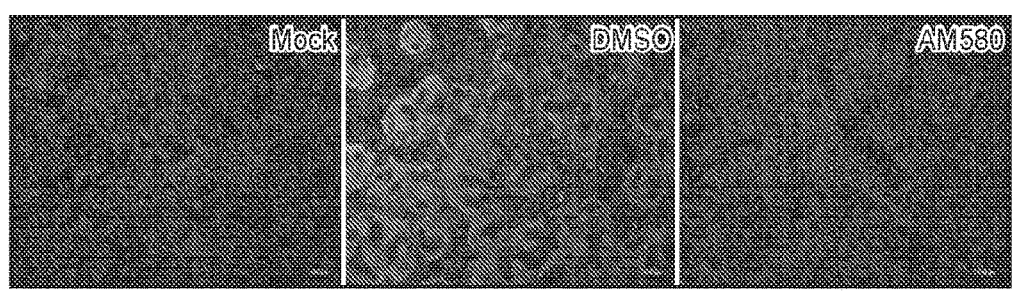
FIG. 10.

Flow cytometry was utilized to determine the percentage of cell infected with MERS-CoV after AM580 treatment. Huh7 cells were infected with 0.01 MOI of MERS-CoV and incubated with or without 20 µM AM580 for 24 hours. As shown in FIG. 9, MERS-CoV NP-positive cells were decreased from 65% (DMSO group) to 5.38% (AM580 group), indicating the efficient blockade of progeny virus production by AM580. Corroborating with the flow cytometry data, immunofluorescence staining for MERS-CoV NP in MERS-CoV-infected Huh7 cells suggested near-complete suppression of virus infection upon AM580 treatment (see FIG. 10).

Figure 11:
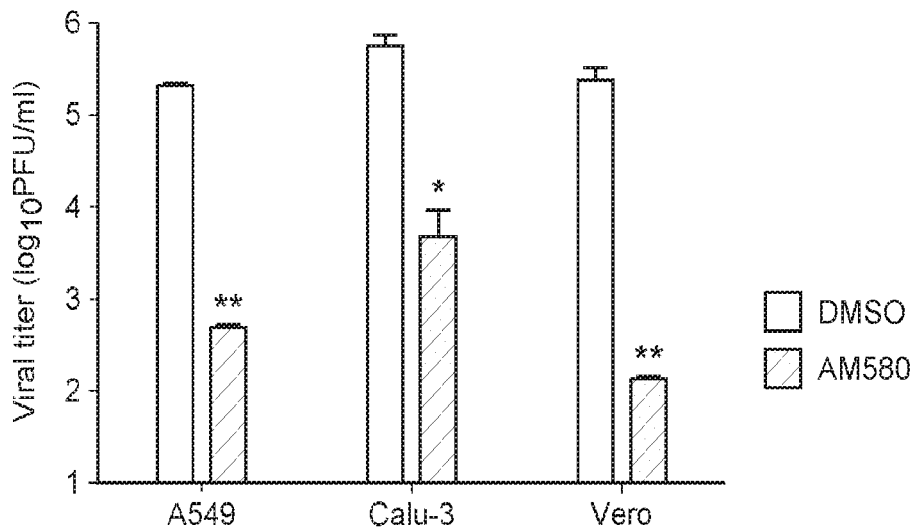
FIG. 11.
Figure 12:
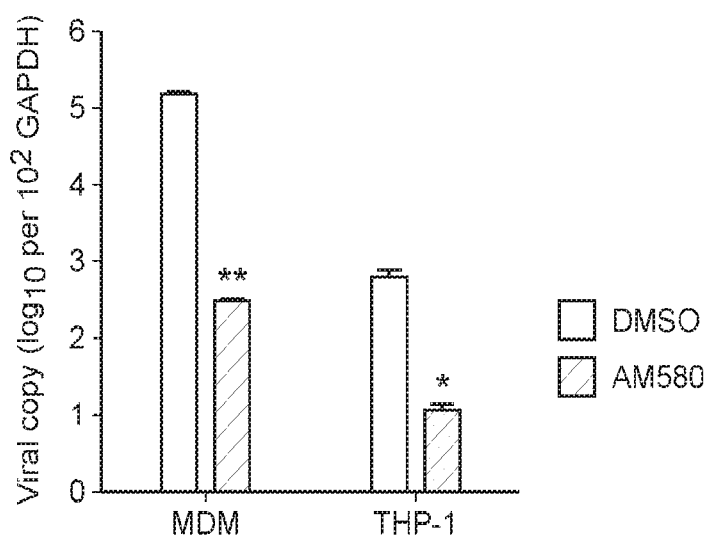
FIG. 12.
Figure 13:
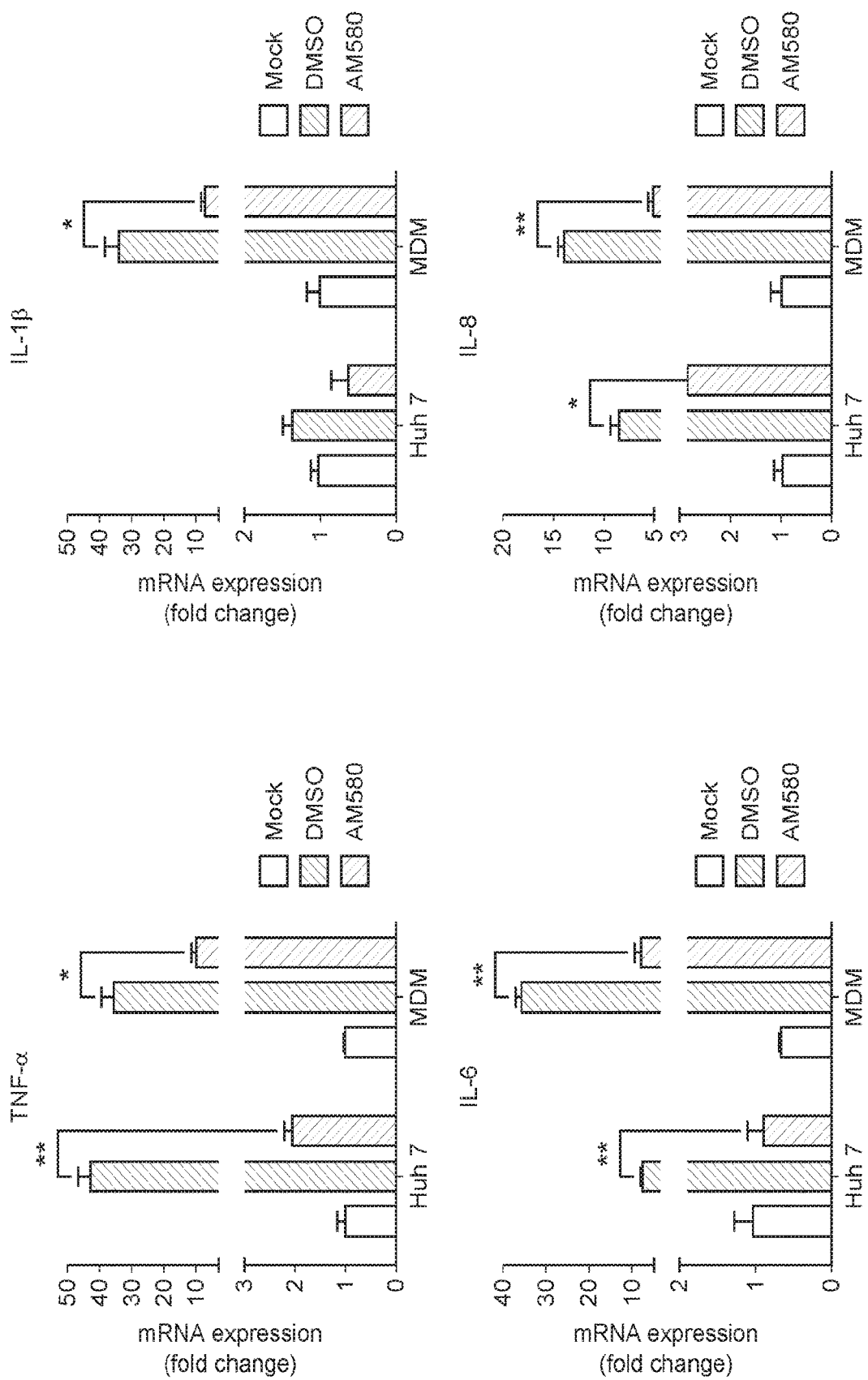
FIG. 13.

In addition, AM580 was also found to reduce MERS-CoV replication in multiple cell types, including pulmonary (A549 and Calu-3), kidney (Vero-E6), and immune cells [THP-1 and human primary monocyte-derived macrophages (MDMs)] (see FIGS. 11 and 12). AM580 was also found to suppress virus-induced pro-inflammatory cytokine activation in Huh7 cells and MDMs (see FIG. 13). Overall, AM580 showed potent anti-MERS activity in cell cultures with cell protection effects and inhibition of virus replication and anti-inflammatory responses.

Figure 14:
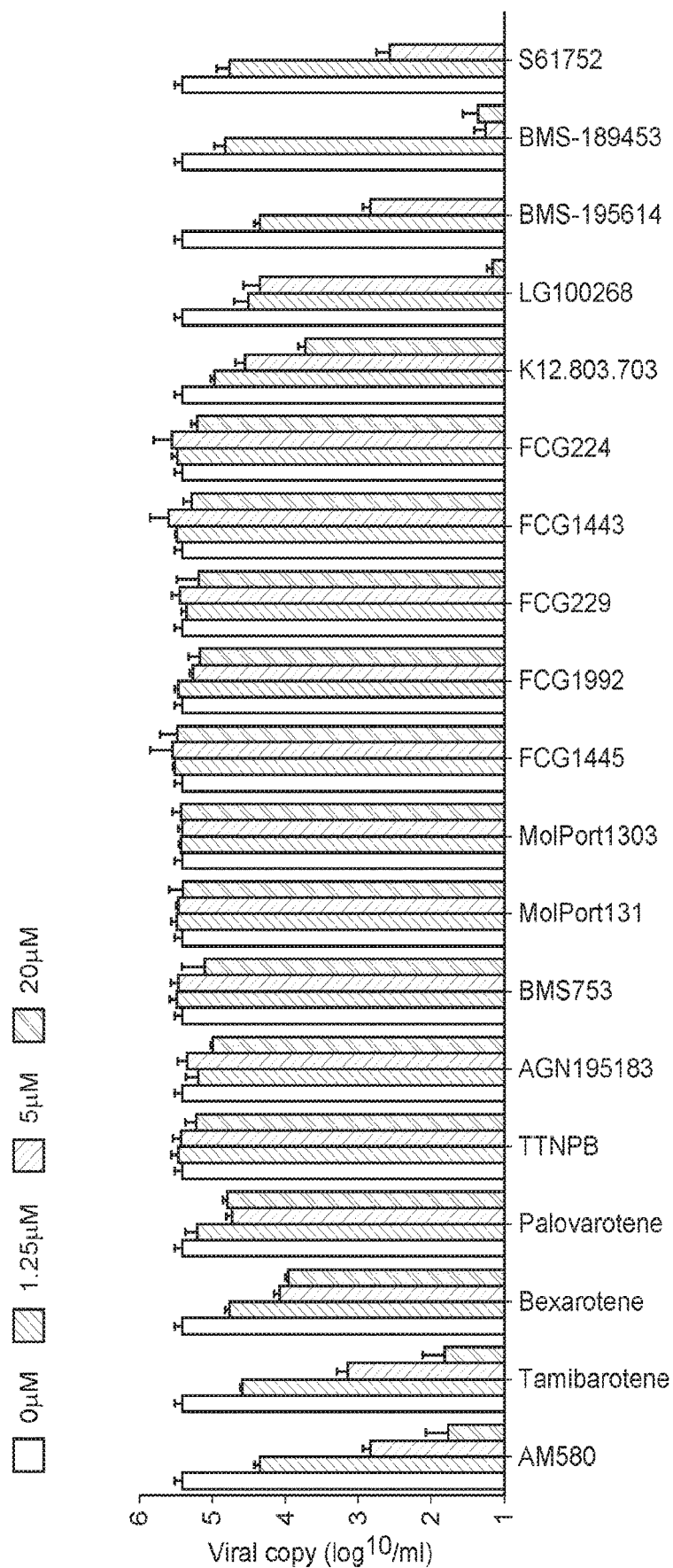
FIG. 14.

To screen AM580 analogs with enhanced bioavailability and antiviral potency, thirteen compounds with structural similarities to AM580 were tested for anti-MERS-CoV activity. Tamibarotene and bexarotene were found to have anti-MERS-CoV activity comparable to that of AM580, with $IC_{50}$'s of 320±26 nM and 875±15 nM, respectively (see FIG. 14). It should be appreciated that these three compounds share a high degree of structural similarity, with all possessing a tetralin moiety on one side of a bridging group and a benzoic acid moiety on the other side (see FIG. 15). A notable difference between these compounds is the central connection bridging group that links the tetralin and benzoic acid moieties. Specifically, both AM580 and tamibarotene utilize an amide bond, but in opposing orientations. Bexarotene has an ethylene in this position). Without wishing to be bound by theory, Inventors believe that both the tetralin and the benzoic acid moieties of these molecules may be important and/or critical to antiviral potency.

Figure 16:
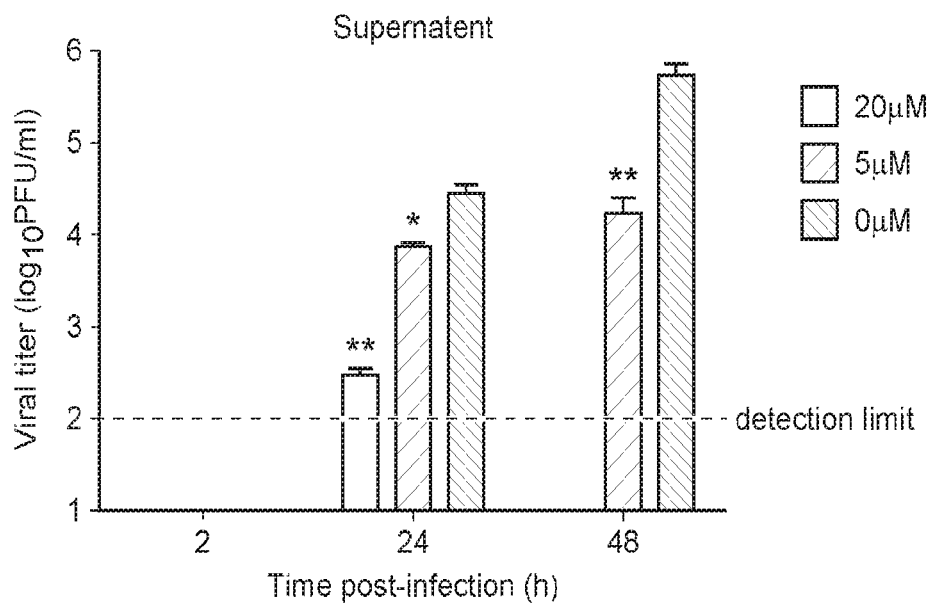
FIG. 16.
Figure 17:
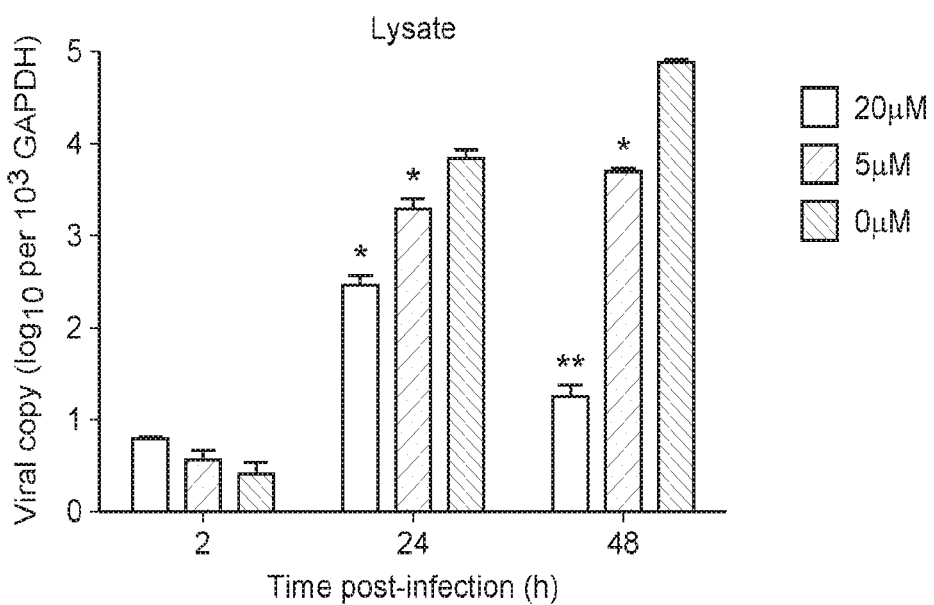
FIG. 17.
Figure 18:
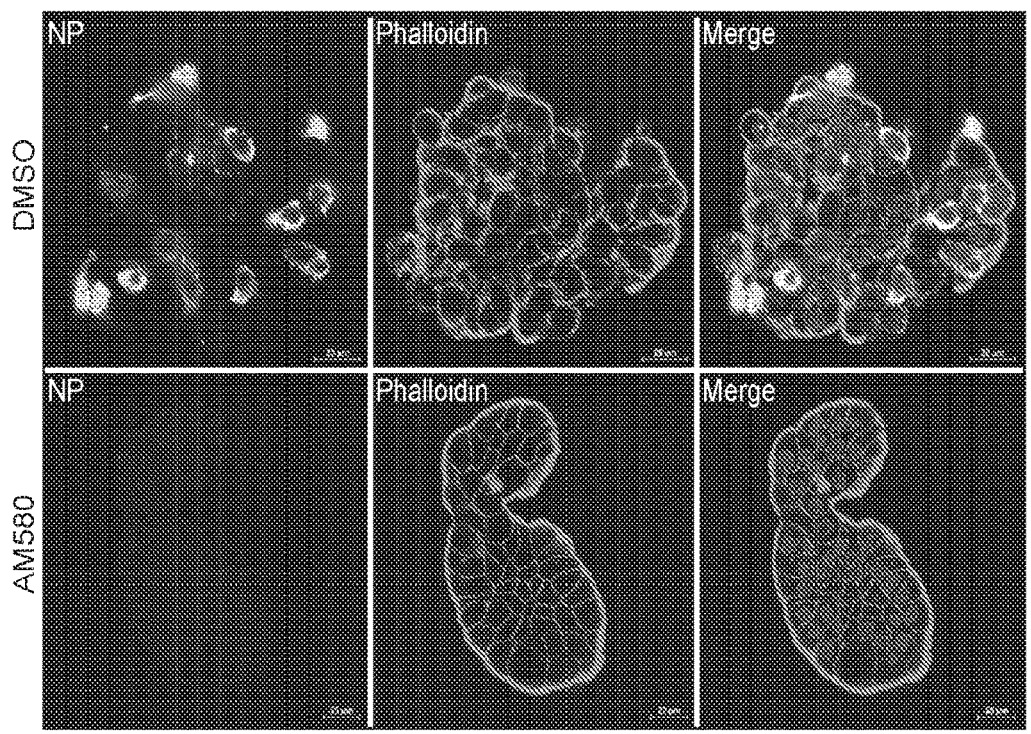
FIG. 18.
Figure 19:
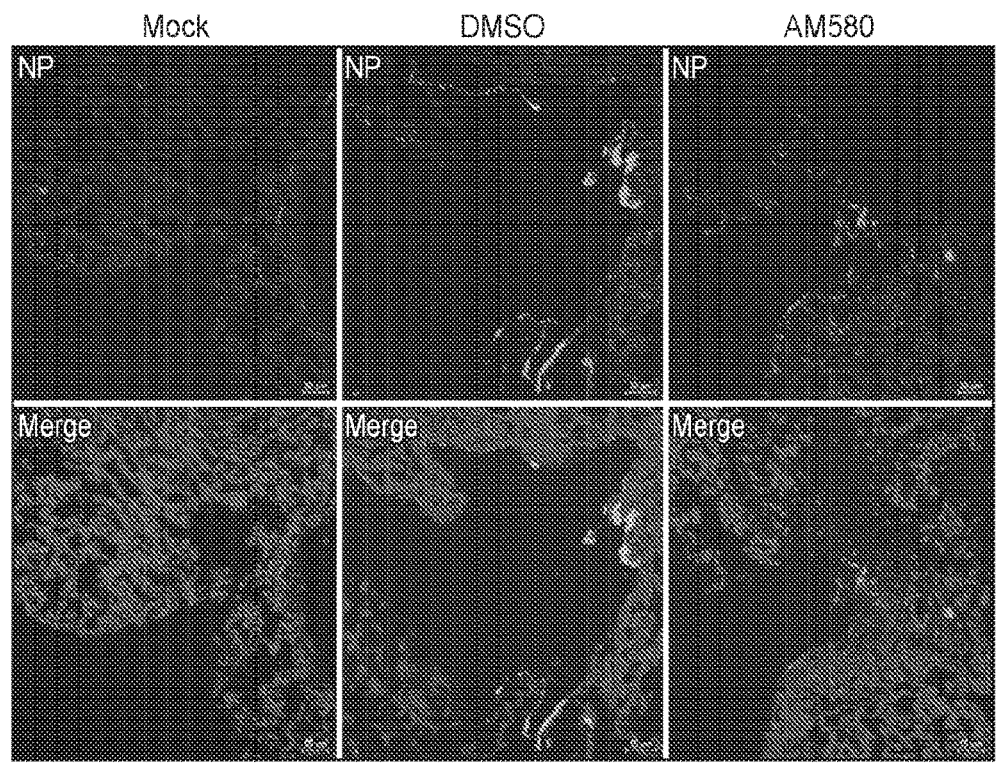
FIG. 19.

Three-dimensional cultured human organoids have substantially advanced the study of human infectious diseases [22]. Inventors have established and characterized MERS-CoV infectivity and replication kinetics in human intestinal organoids (intestinoids), which harbor most types of epithelial cells in the human intestine to simulate the morphological and functional properties of the in vivo setting [23]. Inventors evaluated the antiviral potency of AM580 in this human organ-like system. After inoculation with 0.1 MOI of MERS-CoV, intestinoids exhibited a steady increase in infectious viral titer in Matrigel and supernatant medium (i.e. about 3 $\log_{10}$ and 4 $\log_{10}$ increase at 24 hpi and 48 hpi, respectively) and productive virus replication was detected within the intestinoids (see FIGS. 16 and 17). AM580 treatment was found to significantly (p<0.05) reduce MERS-CoV replication both intra- and extra-cellularly. At 48 hpi, no PFU were detectable in AM580-treated (20 µM) intestinoid culture supernatant, which represents an approximately 6 $\log_{10}$ PFU/ml reduction relative to DMSO-treated control intestinoids (see FIG. 16). Moreover, the AM580-treated intestinoids remained morphologically intact and did not exhibit MERS-CoV-induced CPE as observed in the DMSO-treated control intestinoids (see FIG. 18). The inhibition of MERS-CoV by AM580 in intestinoids was also evidenced by markedly decreased expression of viral NP in the AM580-treated intestinoids compared with the DMSO-treated control intestinoids (see FIG. 18). Additionally, an ex vivo human lung organ culture model showed that AM580 treatment resulted in a marked reduction in MERS-CoV NP expression in the epithelial cells of terminal bronchioles (see FIG. 19). It is apparent that AM580 strongly inhibits viral replication of MERS-CoV in human pulmonary and extra-pulmonary tissues.

Figure 20:
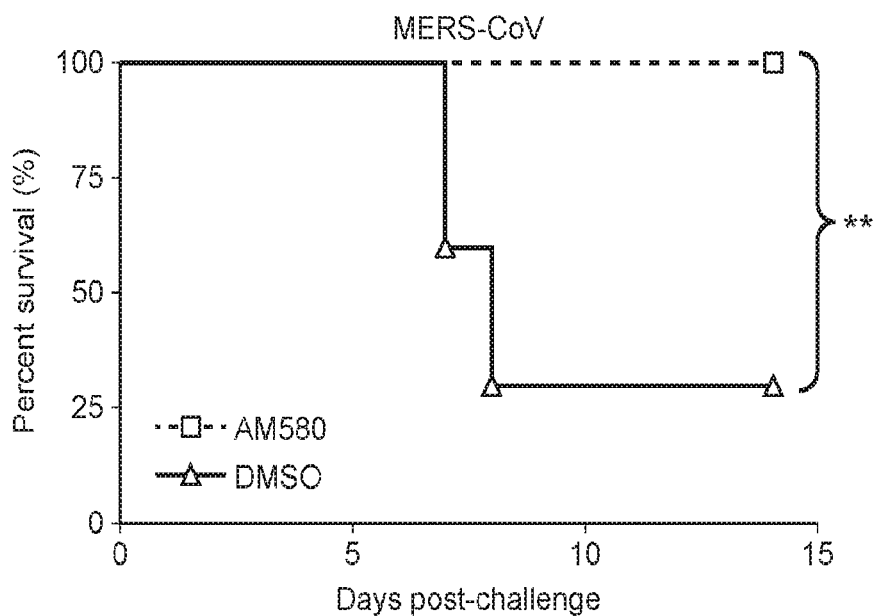
FIG. 20.
Figure 21:
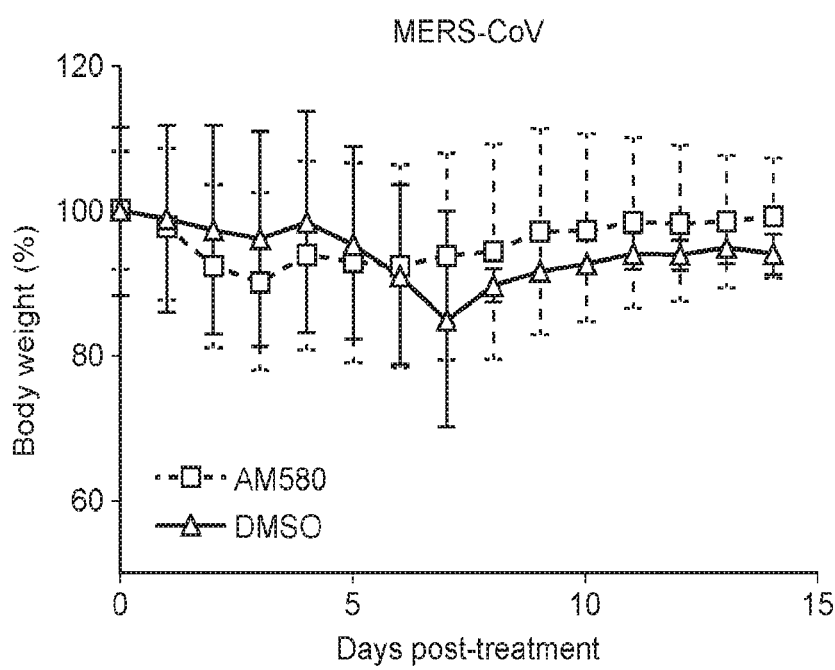
FIG. 21.

To evaluate in vivo antiviral activity of AM580, Inventors examined whether the drug compound conferred protection against lethal challenges of MERS-CoV and influenza A virus in established mouse models using human DPP4 (hDPP4)-transgenic mice [23]. As shown in FIG. 20, among hDPP4-transgenice mice challenged with 50 PFU of MERS-CoV, 10/10 mice (100%) survived after receiving 3 days of intraperitoneal injection with AM580, whereas only 3/10 (30%) PBS-treated mice survived (p<0.01). The mean body weight of the AM580-treated mice was also generally higher than that of the DMSO-treated control mice (see FIG. 21).

Figure 22:
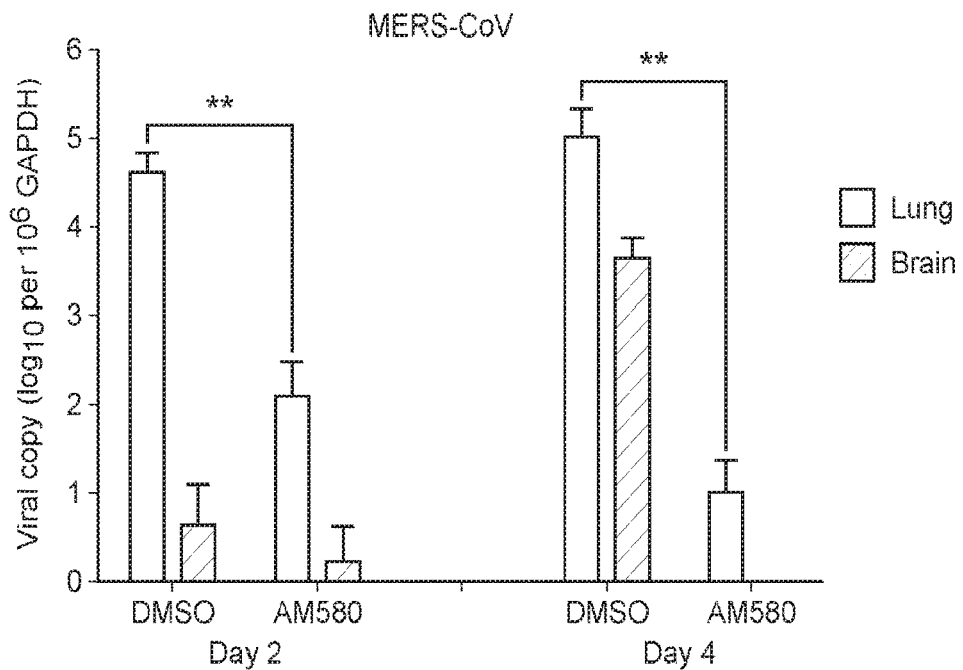
FIG. 22.
Figure 23:
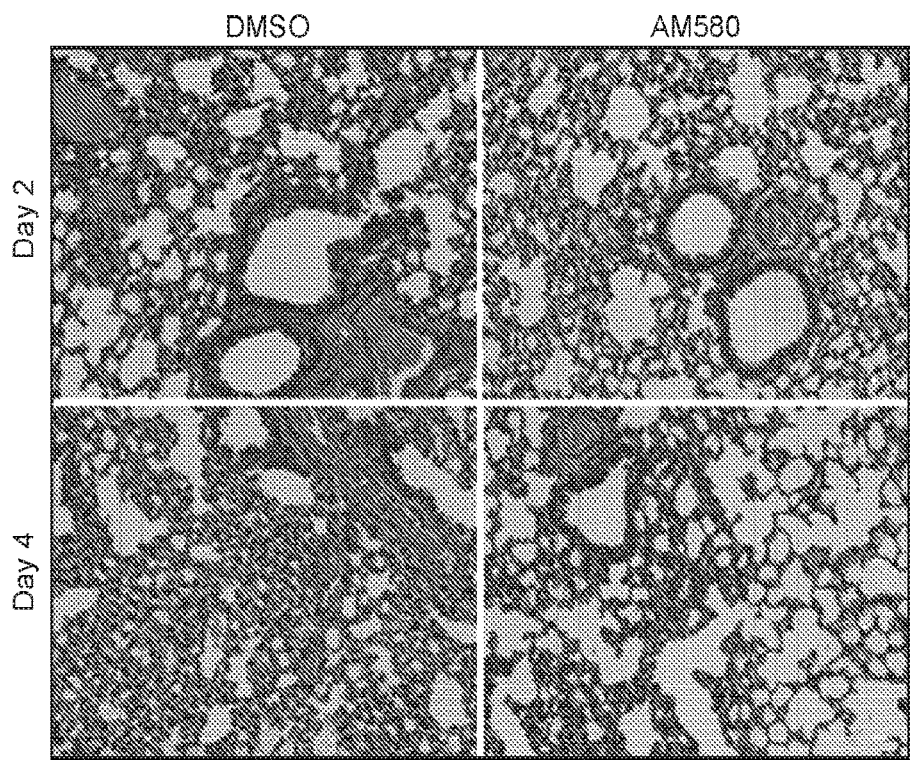
FIG. 23.

Four mice in each group were euthanized on days 2 and 4 after challenge for virological and histological analyses. AM580-treated mice had significantly (p<0.01) lower viral RNA content in their lung tissues as compared with the DMSO-treated control mice at both time-points. Similarly, on day 4 post-challenge the viral RNA content of the brain tissues of the AM580-treated mice was almost undetectable and 4-$\log_{10}$ lower than that of the DMSO-treated control mice (see FIG. 22). Histopathologic examination showed that the alveolar damage and interstitial inflammatory infiltration in lung tissues of the AM580-treated mice were significantly improved relative to those of the DMSO-treated control mice (see FIG. 23). Collectively, these results demonstrated that AM580 effectively protected hDPP4-transgenic mice from lethal MERS-CoV challenge through inhibiting MERS-CoV replication and virus-associated pathology in vivo.

Figures 24, 25:
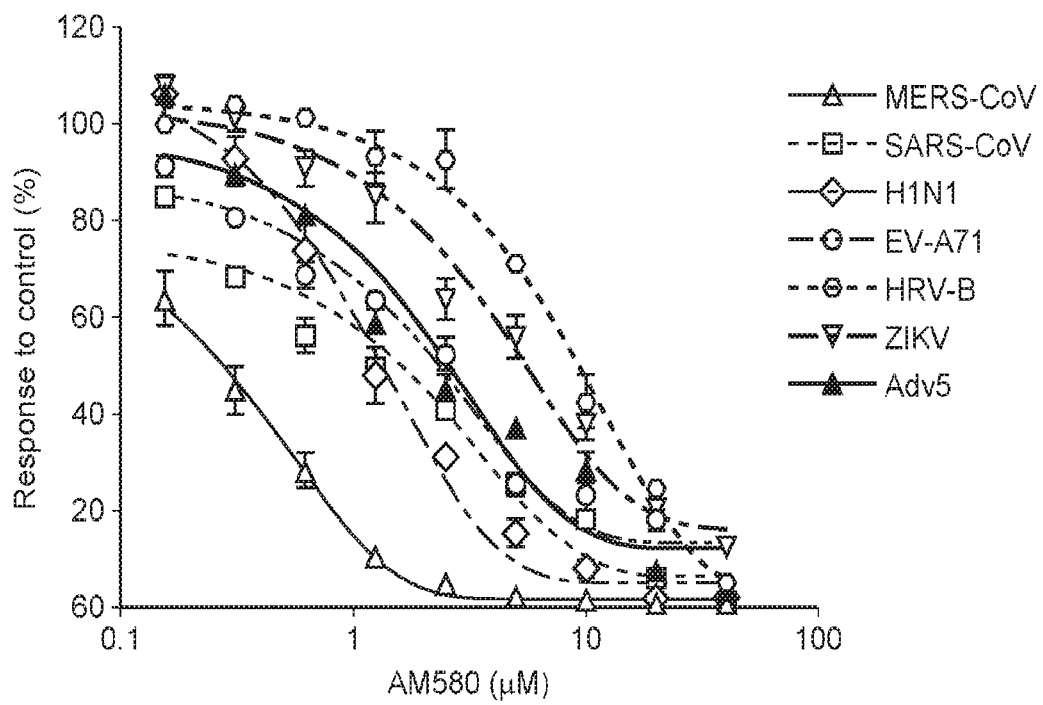
FIG. 24.
FIG. 25.

Inventors have also characterized AM580's antiviral effect against other viral pathogens, including both RNA [e.g. SARS-CoV, Zika virus (ZIKV), influenza virus (e.g. influenza A(H1N1)pdm009 virus), and enterovirus (e.g. enterovirus-A71 (EV-A71)] and DNA [e.g. human adenovirus type 5 (AdV5)] viruses. Surprisingly, AM580 inhibited replication of all these varied viruses species within a range of nanomolar to low micromolar concentrations and in a dose-dependent manner (see FIGS. 24 and 25). The cytotoxicity of AM580 was similar (~100-200 μM) across different cell lines, including those derived from both human and non-human origins, using both the methylthiazol tetrazolium (MTT) and CellTiter-Glo assays (see FIG. 26). Importantly, the selectivity index of AM580 was appropriately adequate high for most of the tested viruses, especially MERS-CoV (507), SARS-CoV (114), and influenza A(H1N1)pdm09 virus (159), which can provide a desirable safety window for clinical use (see FIG. 27). Overall, AM580 has been found to have broad-spectrum antiviral activities against both RNA and DNA viruses, with appropriate pharmaceutical characteristics.

Figure 29:
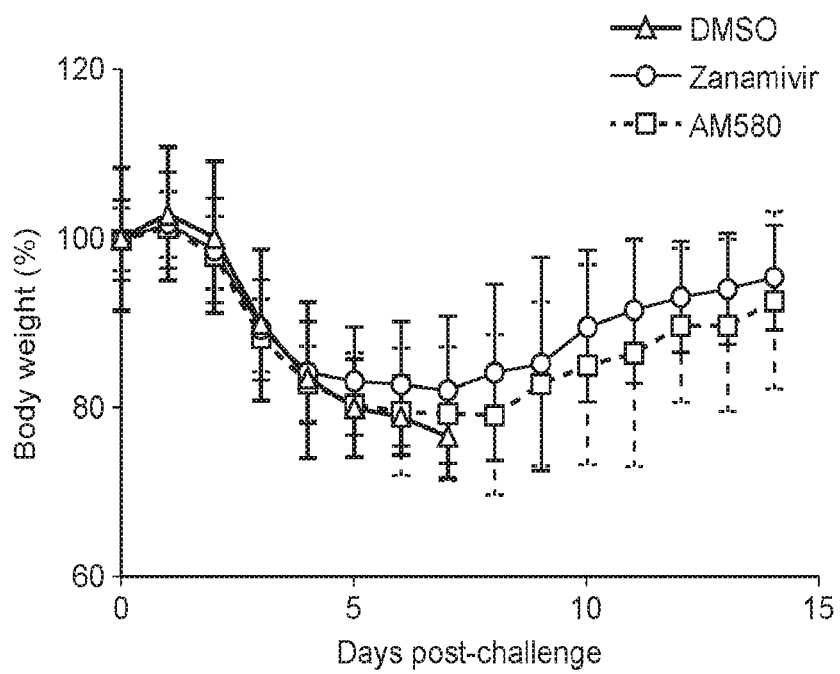
FIG. 29.
Figure 30:
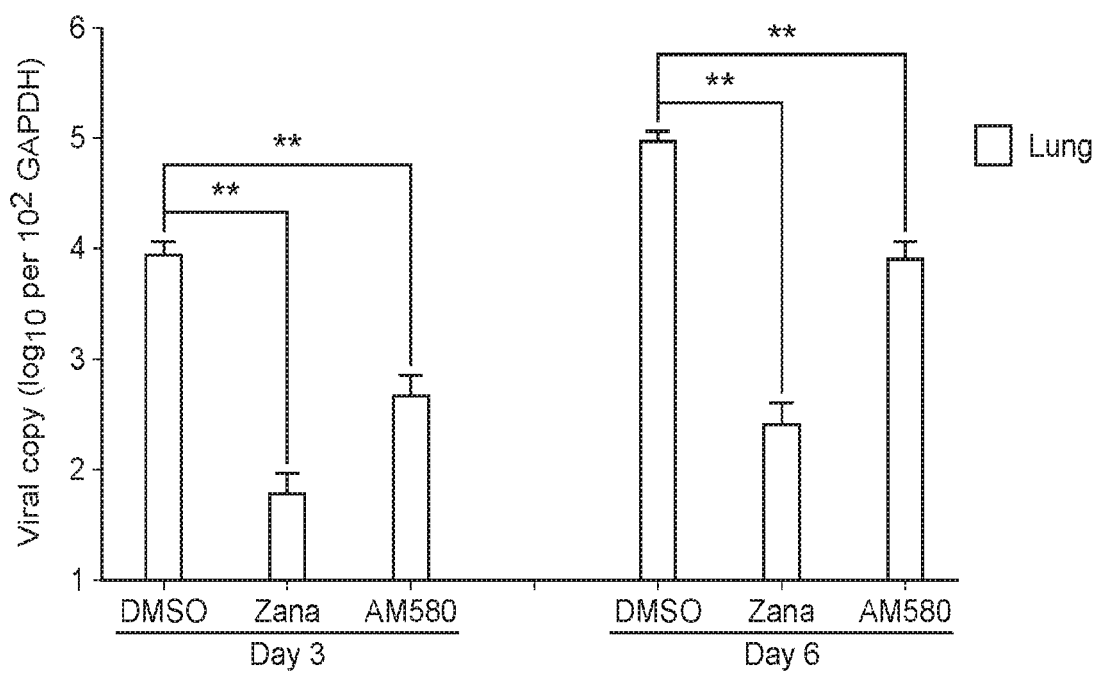
FIG. 30.
Figure 31:
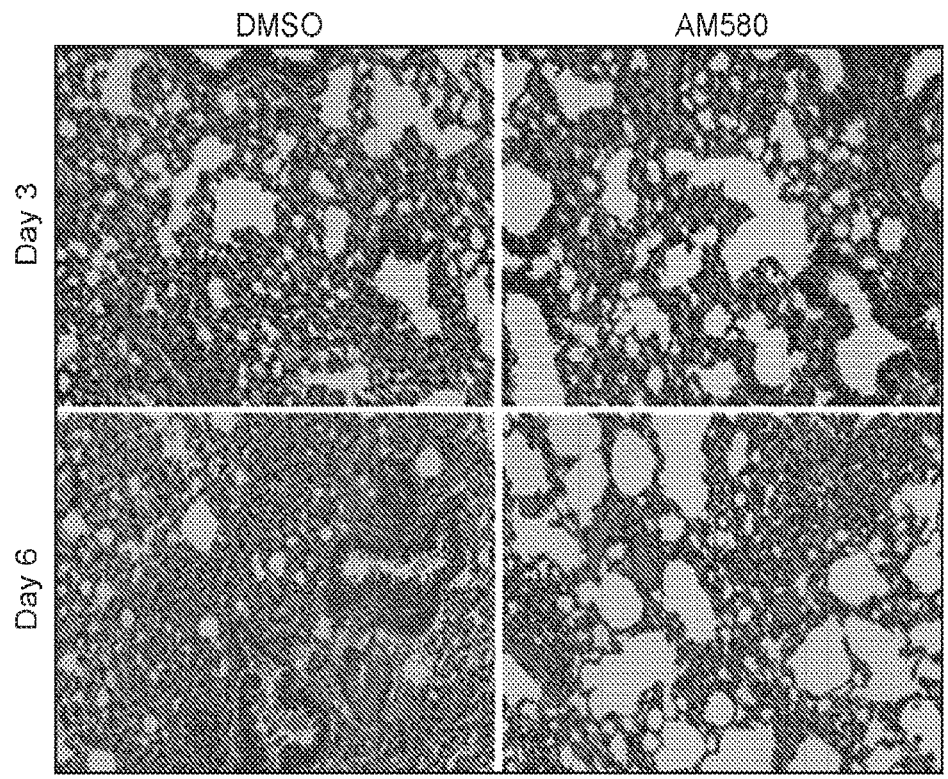
FIG. 31.

Antiviral activity of AM580 against the highly pathogenic Influenza A(H7N9) influenza virus, a more virulent subtype than A(H1N1)pdm09, was also evaluated, using a wild-type Balb/c mouse model. In the mice challenged with 100 PFU of A(H7N9) virus, the AM580-treated mice had significantly (p<0.01) higher survival rates (6/10, 60%) than the DMSO-treated control mice (0/10, 0%) (see FIG. 28). The mean body weight of the AM580-treated mice gradually rebounded starting on day 8 post-challenge (see FIG. 29). The mean viral RNA load in the lung tissues of the AM580-treated mice was significantly (p<0.01) lower than that of the DMSO-treated control mice (see FIG. 30). Histopathological examinations revealed that AM580 treatment ameliorated virus-associated pulmonary inflammatory infiltration and bronchopneumonia (see FIG. 31). It is apparent that AM580 provides significant in vivo protective effects against a highly virulent/lethal influenza A(H7N9) virus challenge.

AM580 is a known selective retinoic acid receptor-α (RAR-α) agonist. Inventors have found, surprisingly, that the antiviral activity of AM580 is not dependent on the activation of RAR-α signaling or on activation of the host's innate antiviral response. To determine the extent to which the antiviral activity of AM580 relies on activation of the RAR-α signaling pathway, loss-of-function and gain-of-function assays were performed. Neither down-regulation of the pathway through RAR-α gene silencing (see FIG. 32) nor hyper-expression of the RAR-α receptor (see FIG. 33) significantly affected MERS-CoV replication. Combined use of downstream RAR-α antagonist ER50891 and AM580 did not diminish the antiviral potency of AM580 (se FIG. 34). These results suggest that the antiviral activity of AM580 is independent of the RAR-α signaling pathway. RAR-α is a nuclear receptor, however, the possibility of AM580 acting as a pan-transcriptional inhibitor was excluded by reporter-gene luciferase assays which included CMV, TK and SV40 promoters (see FIG. 35).

Figure 36:
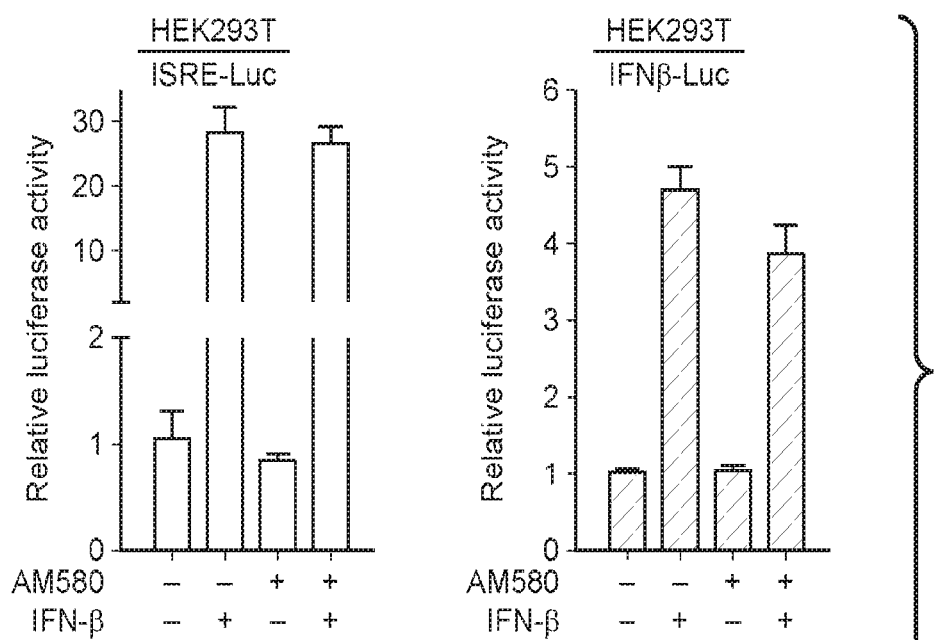
FIG. 36.

To explain the broad-spectrum antiviral activity of AM580 and determine the extent to which host innate immune response was modified by the drug, the Inventors developed reporter constructs driven by an IFN-β promoter (IFNβ-Luc) or by IFN-stimulated response elements (ISRE-Luc) (see FIG. 36). These results indicate that the antiviral activity of AM580 was unlikely to be related to activation of the host's innate immune response and did not function as a signaling amplifier. This is supported by the observation that AM580 exhibited similar antiviral activities in RIG-I knock-out and wildtype A549 cells (see FIG. 37). Collectively, these data suggested that the broad-spectrum antiviral activity of AM580 is not exerted through the activation of the RAR-α-signaling pathway or through the host's innate immune response.

Figures 37, 38:
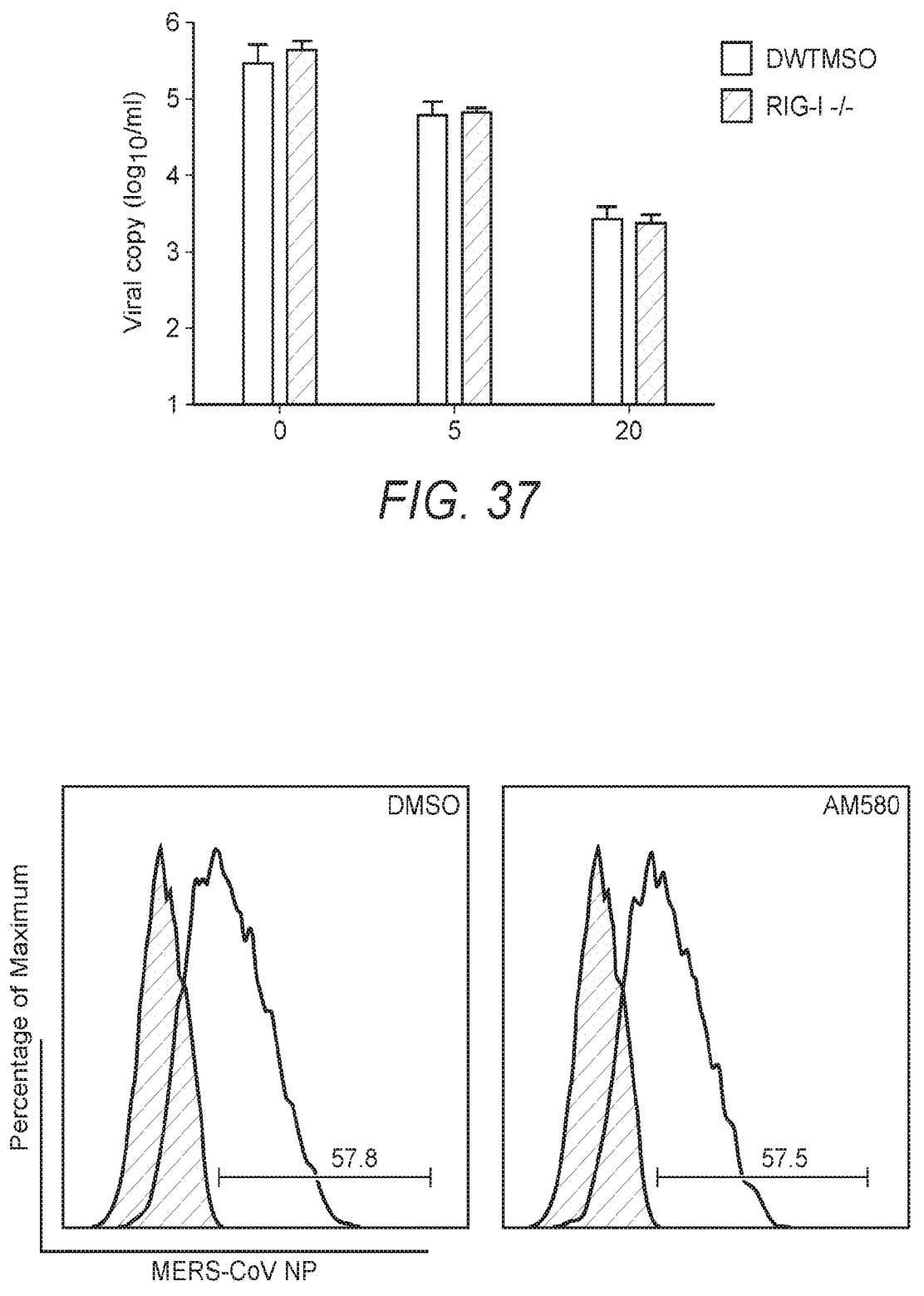

In order to determine the antiviral mechanism of AM580, Inventors utilized a time-of-drug-addition assay, in order to demonstrate that the drug compound did not interfere with MERS-CoV attachment or internalization (see FIG. 38). Without wishing to be bound by theory, the Inventors believe that the drug compound may interrupt the post-entry steps of the MERS-CoV life cycle. To characterize how AM580 affects intracellular virus-host interactions, Inventors performed global gene expression studies of MERS-CoV-infected cells in the presence or absence of the compound. A number of genes were up-regulated (n=2061) or down-regulated (n=1626) in MERS-CoV-infected Calu-3 cells. Notably, the gene expression profiles in AM580-treated and mock-infection groups were similar.

Inventors also conducted pathway enrichment analysis of genes that were significantly differentially expressed among AM580-treated and DMSO-treated cells. Two gene clusters with biggest changes as evidenced by enrichment score >2.0 are listed (see Table 1).

TABLE 1

| Enrichment cluster 1 (score, 5.99) | Count | P |
|---|---|---|
| Alzheimer's disease | 50 | $2.73 \times 10^{-8}$ |
| Non-alcoholic fatty liver disease (NAFLD) | 44 | $4.10 \times 10^{-7}$ |
| Oxidative phosphorylation | 39 | $1.77 \times 10^{-6}$ |
| Huntington's disease | 49 | $5.46 \times 10^{-6}$ |
| Parkinson's disease | 39 | $9.80 \times 10^{-6}$ |

| Enrichment cluster 2 (score, 2.53) | Count | P |
|---|---|---|
| Lysine degradation | 19 | $6.37 \times 10^{-5}$ |
| Fatty acid degradation | 16 | $3.12 \times 10^{-4}$ |
| Tryptophan metabolism | 15 | $3.61 \times 10^{-4}$ |
| Butanoate metabolism | 10 | $5.89 \times 10^{-3}$ |
| Fatty acid metabolism | 14 | $7.59 \times 10^{-3}$ |
| Valine, leucine and isoleucine degradation | 12 | $3.86 \times 10^{-2}$ |

The differentially expressed genes in AM580-treated and untreated samples are subjected to pathway enrichment and cluster analyses.

The highest scoring pathway in each gene cluster were associated with Alzheimer's disease and lysine degradation, respectively. Ranking after this, MERS-CoV-infected cells treated with AM580 had significantly reduced expression of genes that were functionally related to fatty acid metabolism, fatty acid degradation, and non-alcoholic fatty liver disease (NAFLD). Overall, without wishing to be bound by theory Inventors believe that AM580 may reprogram the lipid metabolism profile triggered by virus replication. Notably, dysregulation of cholesterol and phosphoinositides pathways has been highly implicated in amyloidogenesis of Alzheimer's Disease [24], while ketogenic essential amino acid such as Lysine modulates lipid synthetic pathways [25].

Figure 39A:
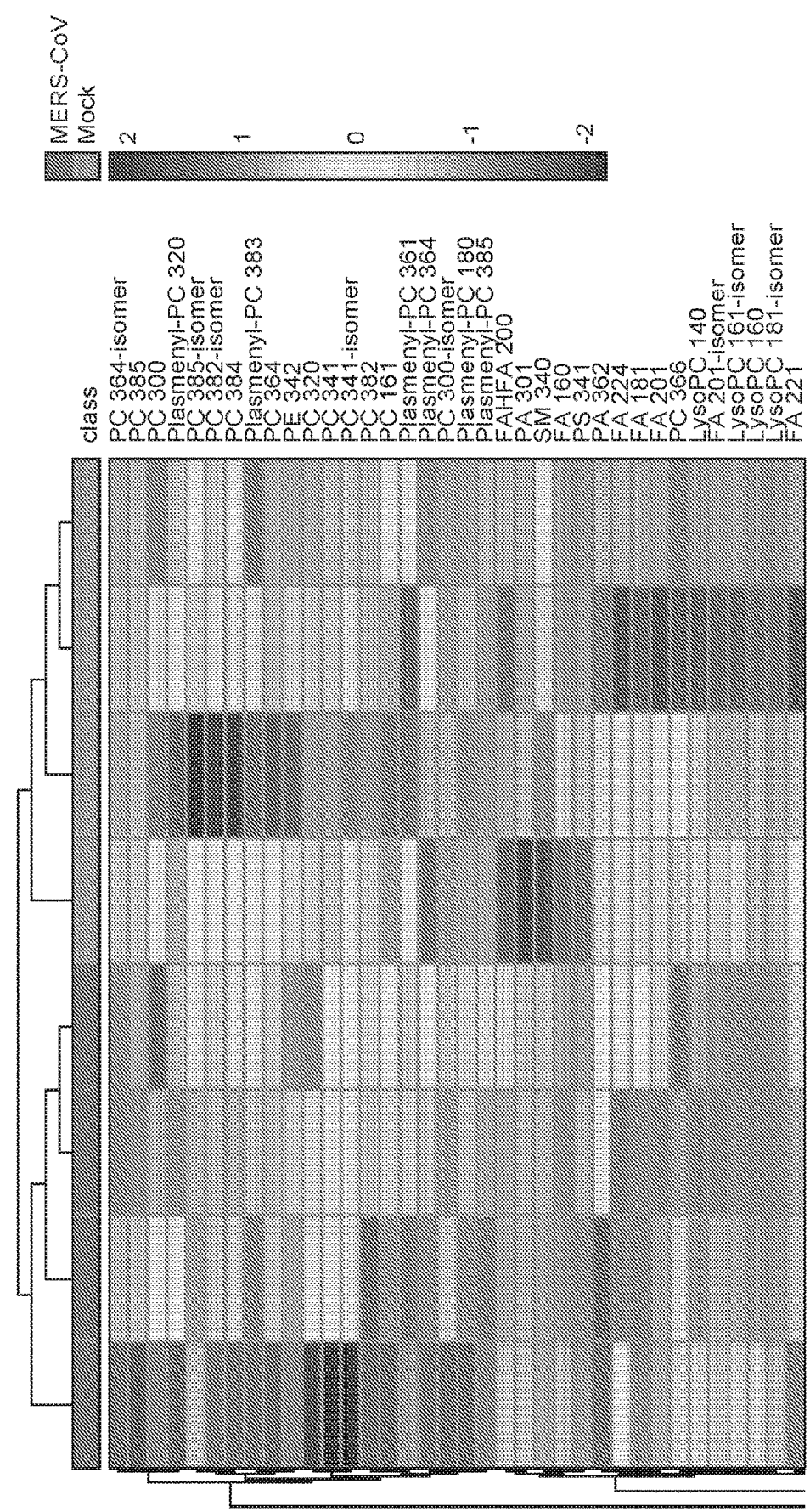
FIG. 39.
Figure 39B:
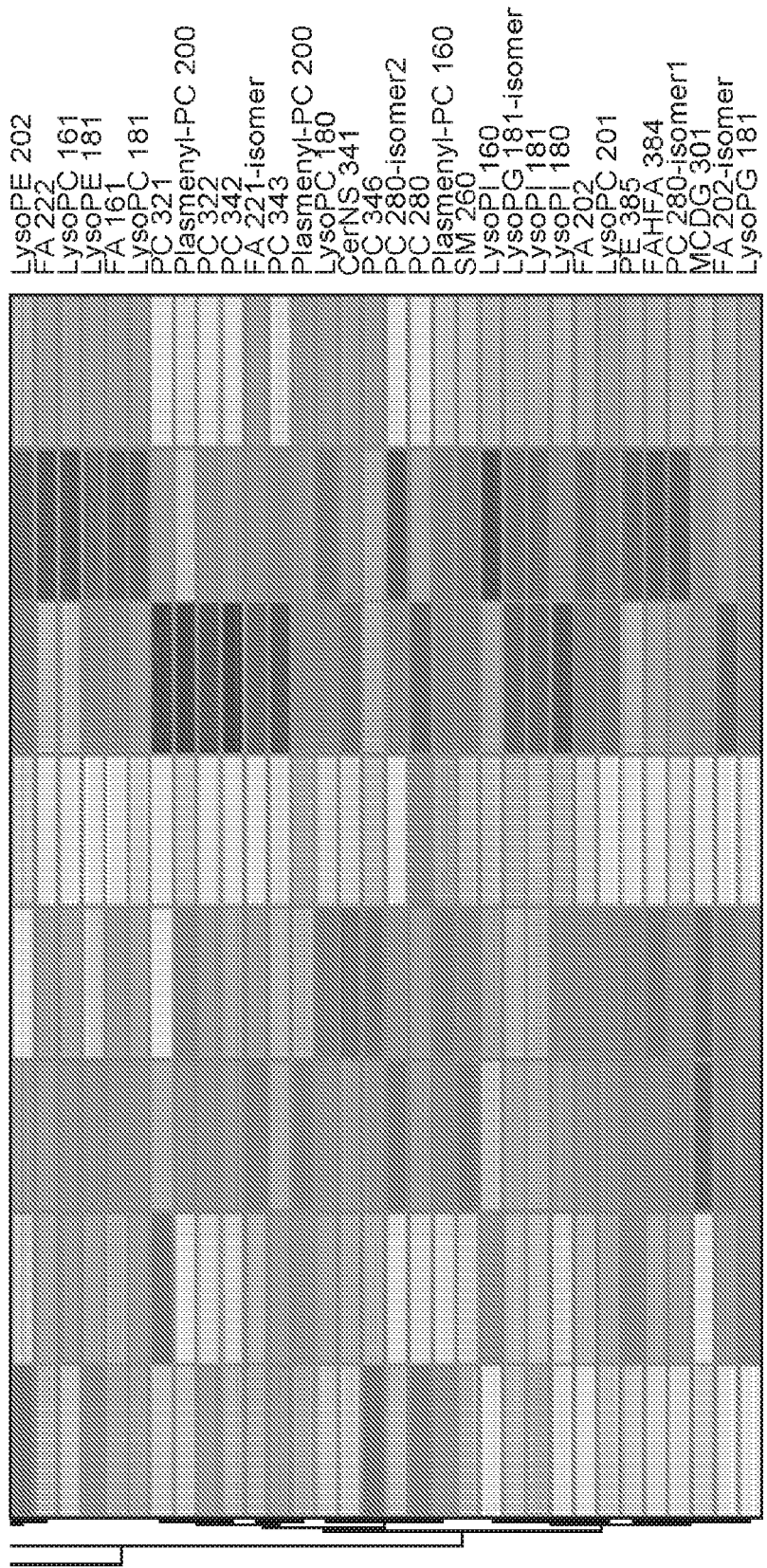
Figure 42:
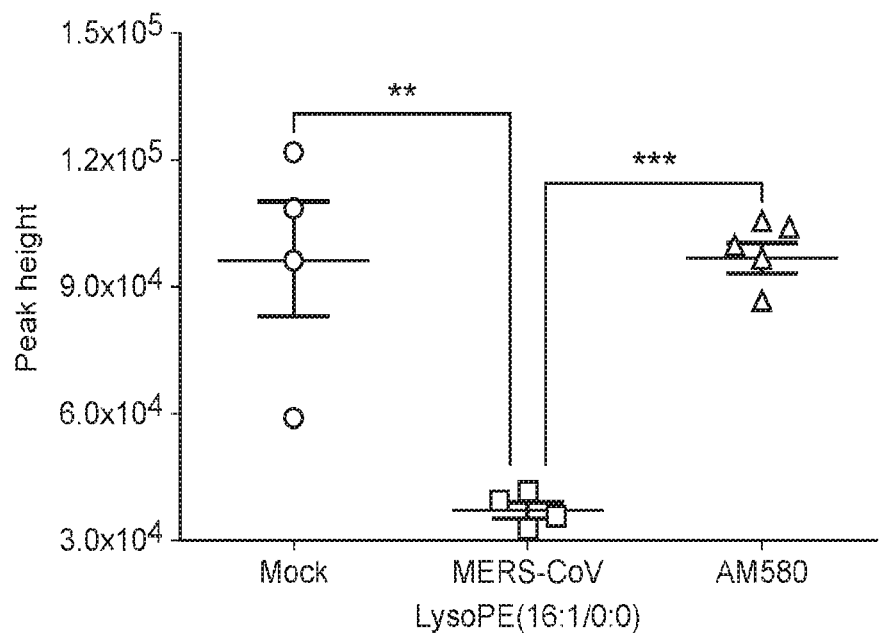
FIG. 42.
Figure 43:
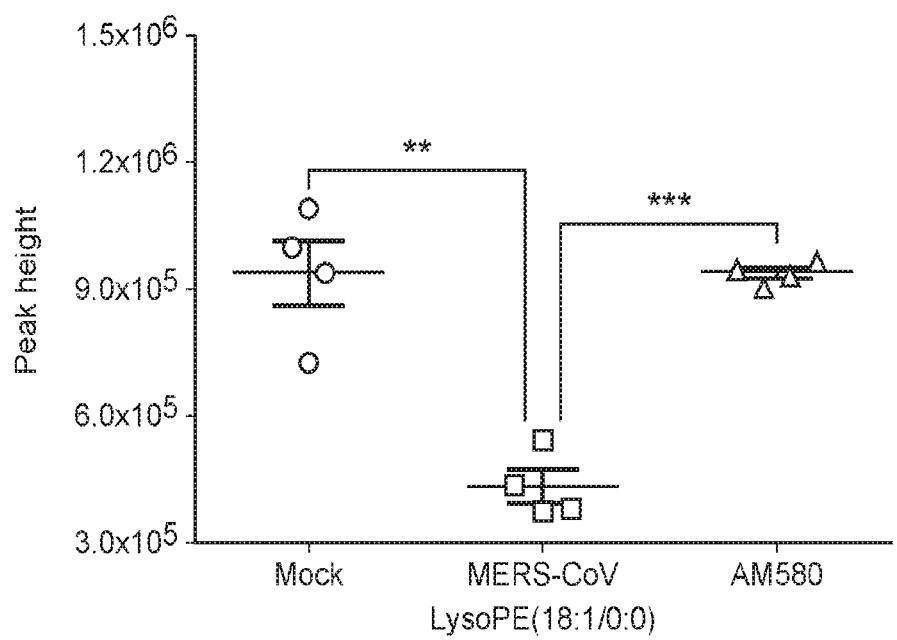
FIG. 43.
Figure 44:
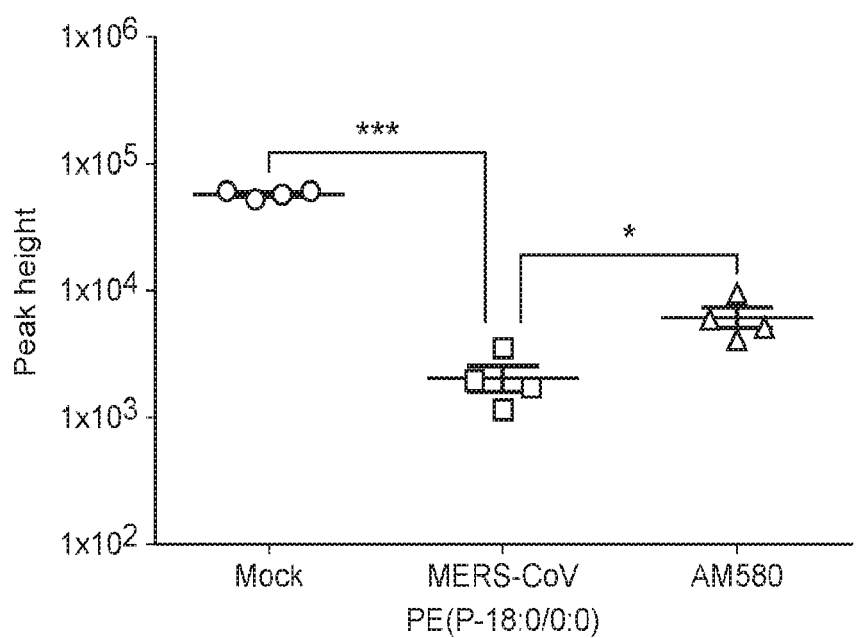
FIG. 44.
Figure 45:
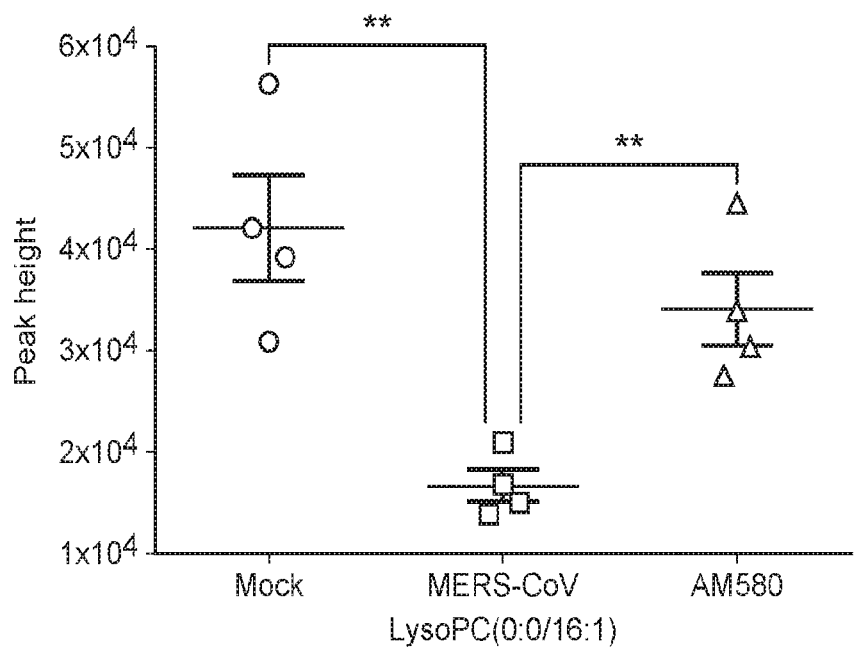
FIG. 45.
Figure 46:
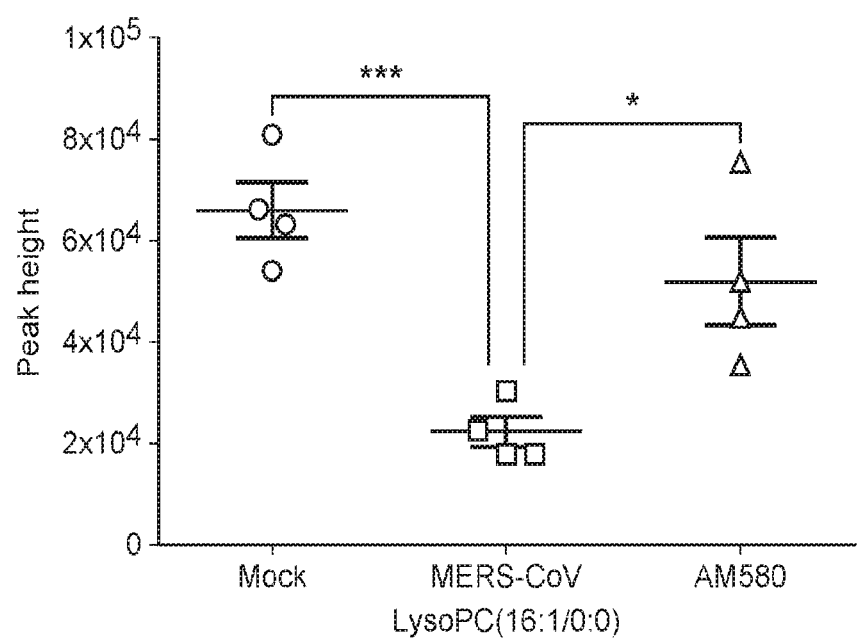
FIG. 46.
Figure 47:
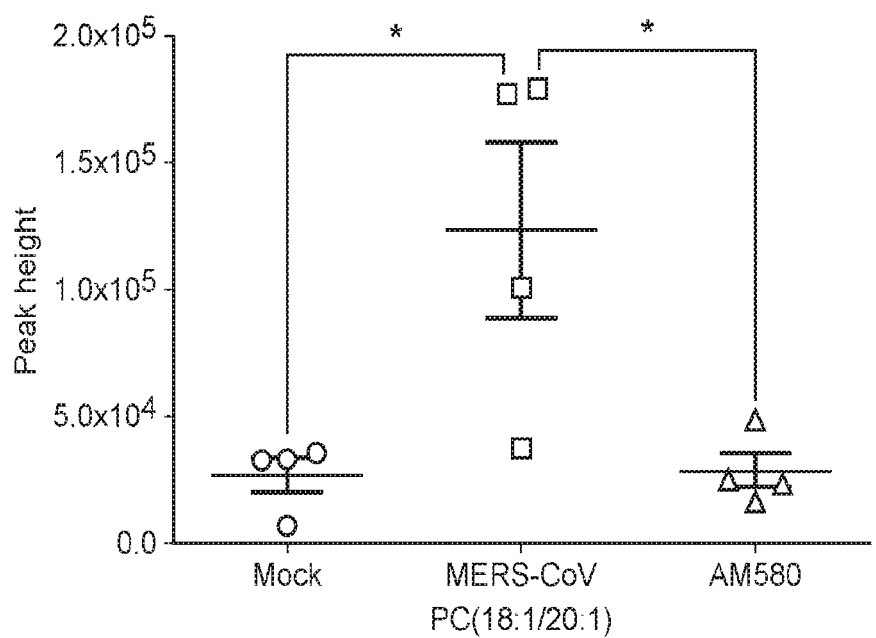
FIG. 47.
Figure 48:
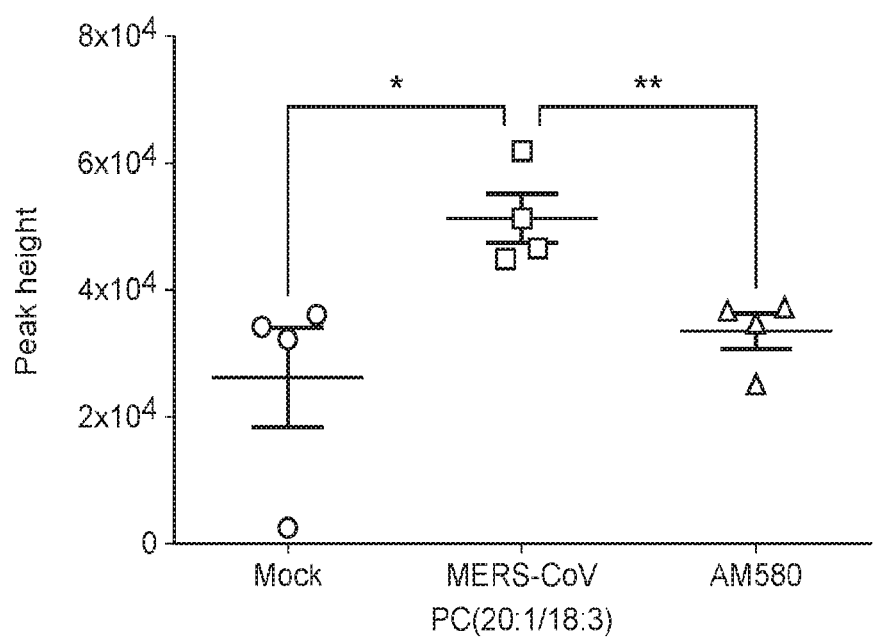
FIG. 48.
Figure 49:
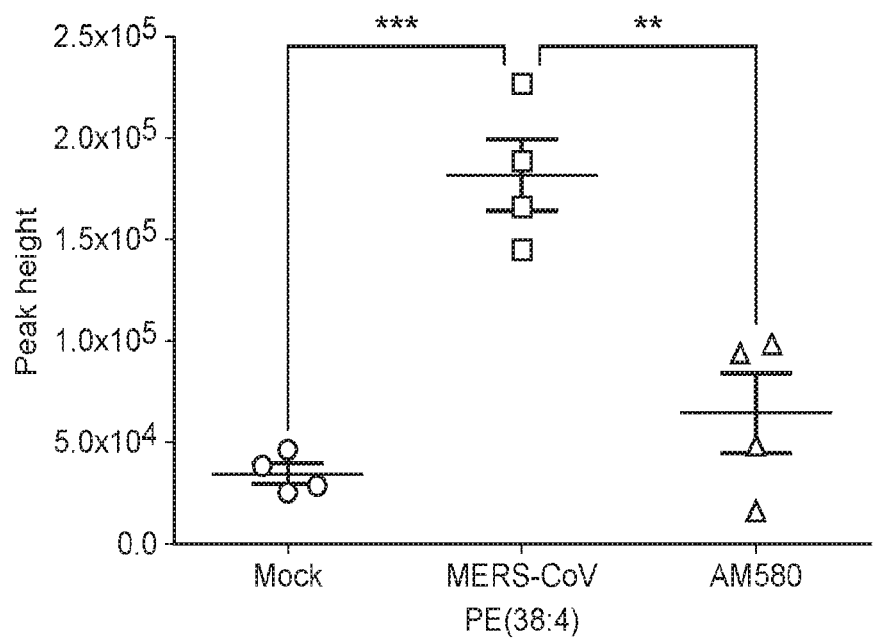
FIG. 49.
Figure 50:
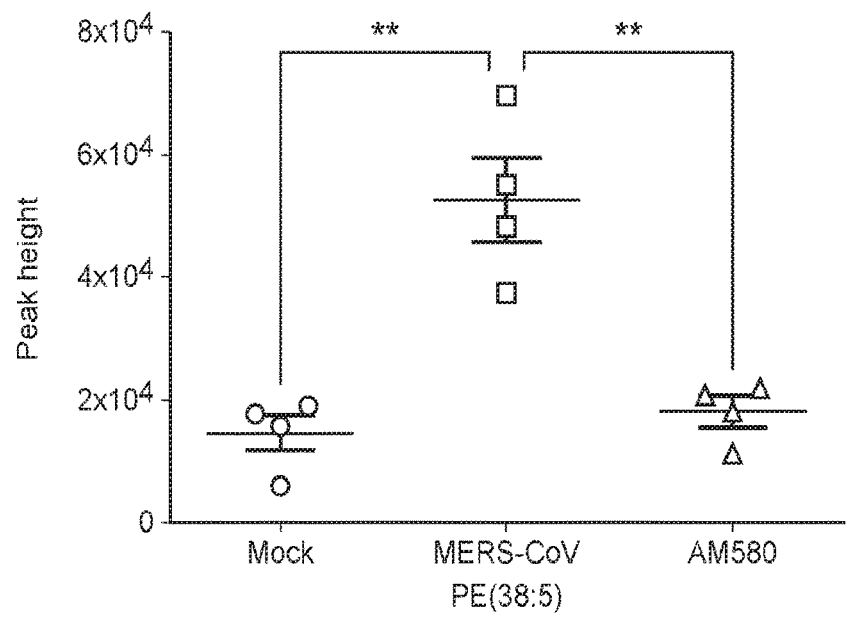
FIG. 50.

To further explore the role of AM580 in MERS-CoV-induced perturbation of lipid homeostasis, Inventors performed untagged lipidomic analysis of MERS-CoV-infected Calu-3 cells in the presence or absence of AM580 (see FIG. 39). Lipids were isolated at 24 hpi. The abundances of 308 lipid features in positive mode and 199 lipid features in the negative mode of 11 lipid classes were characterized. After removing duplicated lipid features, data processing and statistical analysis were performed. A number of changes in the cellular lipidome were observed in AM580-treated, MERS-CoV-infected cells when compared with those of the mock-infected and DMSO-treated MERS-CoV-infected control cells. Twelve endogenous lipids showed significant ($p<0.05$) changes (see FIGS. 40 to 50). All of the identified lipids belonged to the glycerophospholipid class. Glycerophospholipids (GPs) constitute the main lipid category of mammalian cell membrane. Structurally, GPs are further classified into four subgroups, including two lysophospholipids (LysoPLs) [lysophosphatidylcholine (LysoPC) and lysophosphatidylethanolamine (LysoPE)] and two phospholipids (PLs) [phosphatidylcholine (PC) and phosphatidylethanolamine (PE)]. To characterize the trend of variations, Inventors performed a hierarchical clustering analysis based on the degree of abundance of different lipids. At 24 hpi, MERS-CoV infection down-regulated LysoPLs (LysoPC and LysoPE) and up-regulated PLs (PC and PE) when compared with mock-infected control (see FIG. 39). AM580 antagonized this virus-induced perturbation of lipid homeostasis and exhibited a similar lipidome as the mock-infected control (see FIGS. 40 to 50).

Two concerted enzymes, namely, phospholipase A2 (PLA2) and lysophospholipid acyltransferase (LPCAT), balance the turnover of LysoPLs and PLs in the Lands' cycle [26]. PLA2 specifically hydrolyze the sn-2 position ester bond of PLs to form LysoPLs. Subsequently, the lipid-regenerating enzyme LPCAT transfer an acyl-group from acyl-CoA to LysoPLs to regenerate phospholipids, thus completing the de-acylation/re-acylation cycle. MERS-CoV replication favored PLs rather than LysoPLs formation (see FIGS. 40 to 50). In line with the lipidomic data, gene expression of a panel of PLA2s, including PLA2G4A, PLA2G10, PLA2G12A, PLA2G16, and PLA2R1, were significantly suppressed with MERS-CoV infection ($p<0.05$) when compared with the AM580-treated or mock-infected control groups. Collectively, these results indicate that MERS-CoV infection perturbs lipid homeostasis through de-acylation and re-acylation of the Lands' cycle, in which the cellular phospholipases played a modulatory role. Inventors believe these to be viral induced changes in favor of viral replication and survival.

Figure 51:
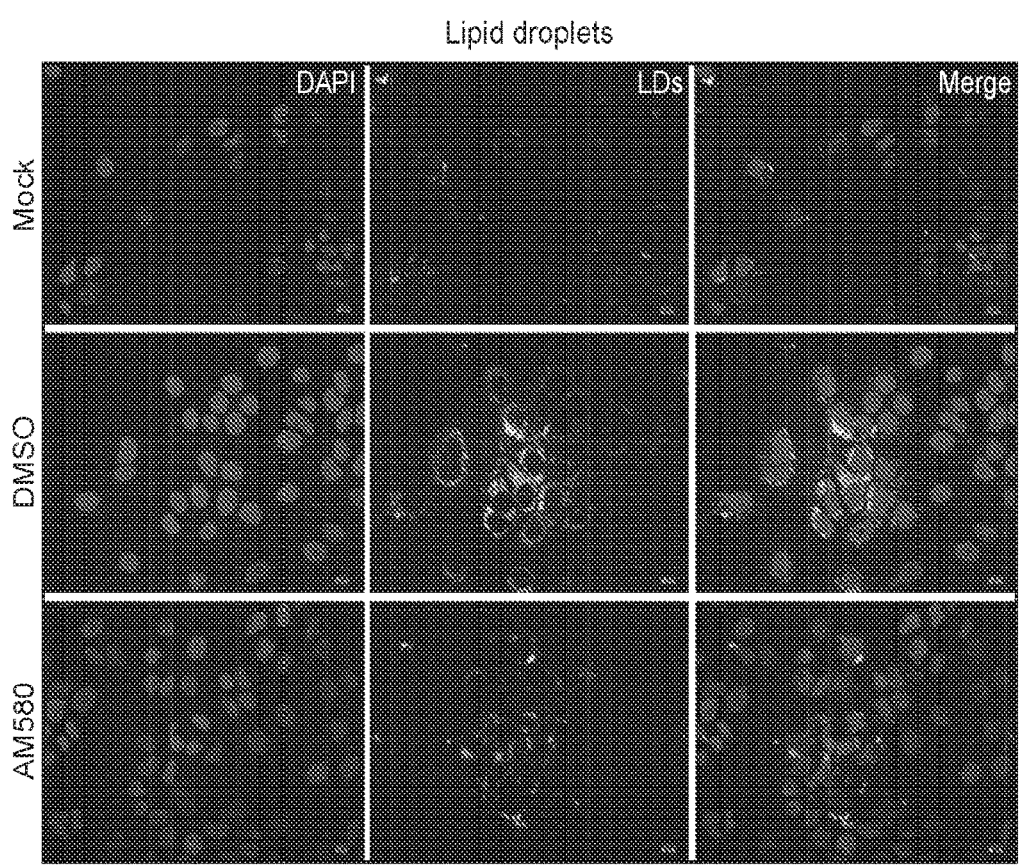
FIG. 51.
Figure 52:
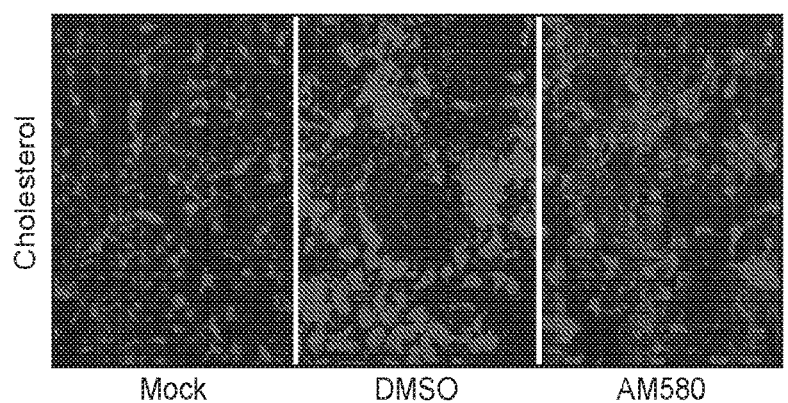
FIG. 52.
Figure 53:
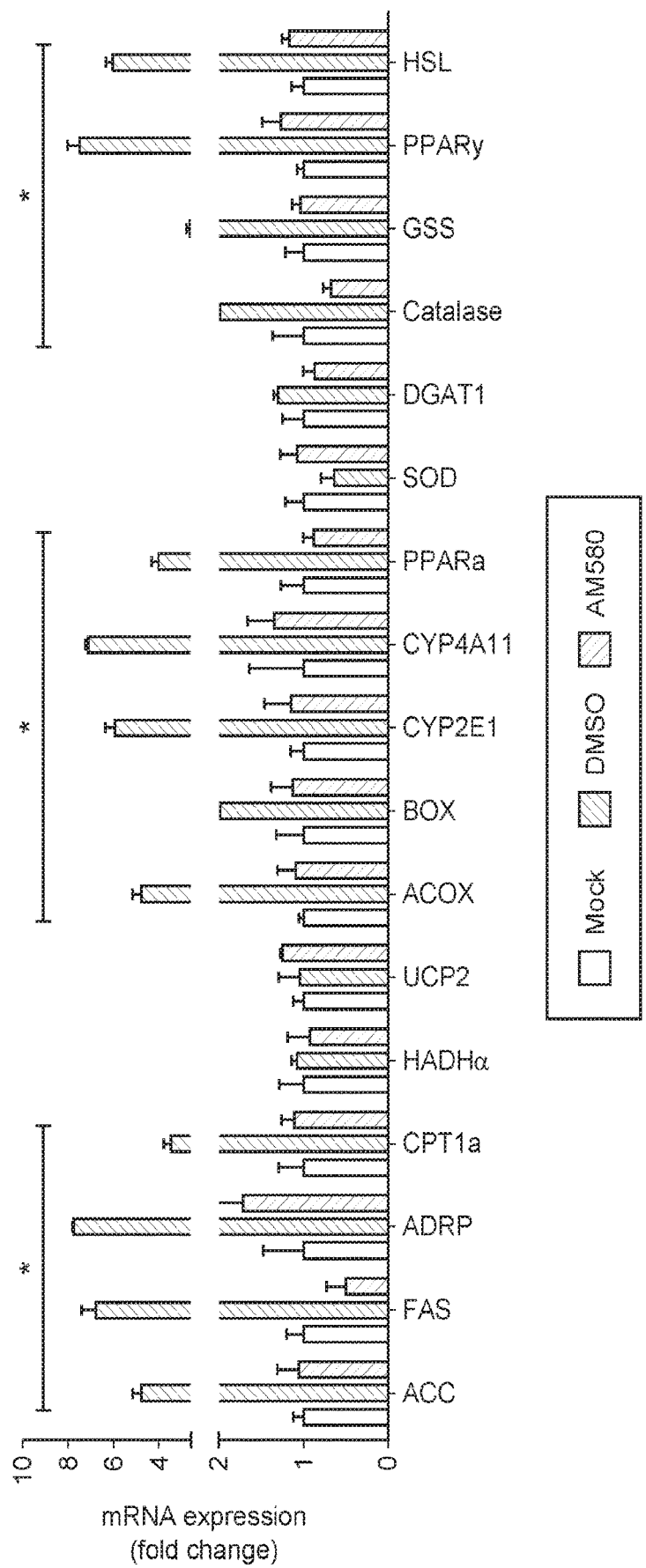
FIG. 53.

In order to characterize lipid metabolic changes, Inventors used immunofluorescence to visualize the distribution patterns of cellular lipid droplets (LDs) and cholesterol within MERS-CoV-infected Huh7 cells in the presence or absence of AM580 and a RT-qPCR assay to measure changes in mRNA expression. As shown in FIGS. 51 and 52, infection by MERS-CoV markedly enhanced the accumulation of LDs and cholesterol, whereas addition of AM580 significantly reduced their production. In addition the expression of 18 key catalytic genes involved in fatty acid metabolism, including the de novo fatty acid synthesis and uptake pathway (ACC, FAS, ADRP), fatty acid oxidation pathway (CPT1a, HADHa, UCP2, ACOX, BOX, CYP2E1, CYP4A11, PPARα), antioxidant pathway (SOD, catalase, GSS), and triglyceride synthesis and catalysis pathway (DGAT1, PPARγ, HSL), were characterized. Significant decreases in mRNA expression were detected in 13/17 (76.5%) genes in the AM580-treated infected cells, when compared with those of the DMSO-treated infected controls (see FIG. 53).

Figure 54:
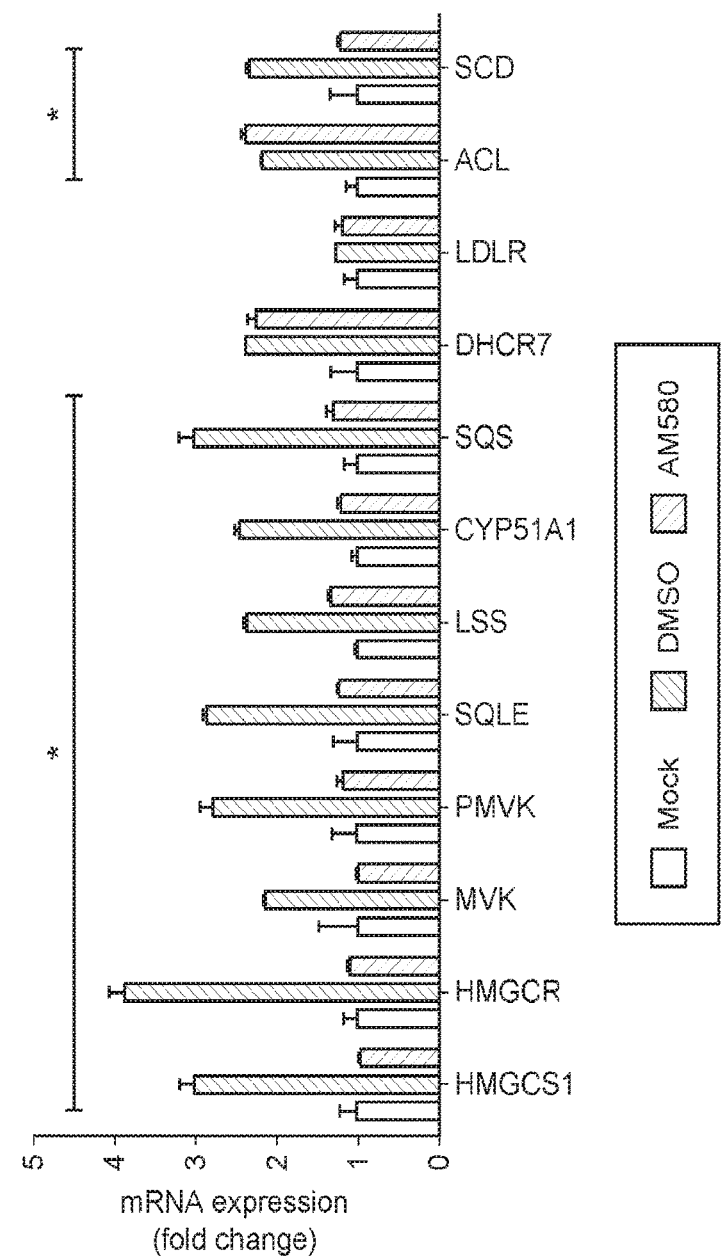
FIG. 54.

Similarly, mRNA expression in 10/12 (83.3%) measured genes in the cholesterol synthetic pathway, such as HMGCR, HMG-CoA synthase (HMGCS), and SCD, were reduced by AM580 treatment (see FIG. 54). These findings not only suggested that fatty acid and cholesterol synthesis is an essential component of the MERS-CoV life cycle (as evidenced by the profound increase of the major biosynthetic enzymes, acetyl-CoA carboxylase (ACC), fatty acid synthase (FAS), and HMGCS during MERS-CoV infection), but also that AM580 and its analogs can inhibit lipid synthesis in a fashion that affects one or more steps of virus replication. Without wishing to be bound by theory, the Inventors believe that the heightened metabolic demands triggered by MERS-CoV infection rapidly up-regulates lipid biosynthetic pathways, while AM580 might antagonize such reprogramming and result in reduced virus replication.

SREBP-1 and SREBP-2 are the primary transcription factors that control biosynthesis of cholesterol, fatty acids, and triglycerides [27]. In order to characterize the role of SREBPs during MERS-CoV replication Inventors compare the growth of MERS-CoV between wildtype (mock treatment) and pretreated (knockdown or hyper-expression of SREBPs) cells. Notably, transfection with SREBP-1- or SREBP-2-targeted siRNAs diminished precursor SREBPs (pre-SREBPs) production, which led to significantly ($p<0.05$) reduced MERS-CoV replication (see FIG. 56). This indicates that SREBPs are essential for MERS-CoV replication.

Transactivation of lipid biosynthesis genes requires cleavage of pre-SREBPs to release the nuclear form (n-SREBPs); this process is regulated by sterol [28]. To induce this mature form of SREBPs to mimic the over-activation of lipid biosynthesis during virus infection, Huh7 cells were depleted of sterols by incubation with 5% lipoprotein deficient serum (LPDS) and 10 μM mevastatin overnight. Starvation of the cells enriched endogenous n-SREBP1 and n-SREBP2 (see FIG. 56). The increased n-SREBPs, however, diminished the antiviral potency of 10 μM AM580 by about 1 $\log_{10}$ unit upon MERS-CoV infection with 0.1 or 1 MOI. This suggests a promotional role for SREBPs in MERS-CoV replication and an inhibitory role for AM580 and related compounds on the n-SREBPs involved.

Figure 57:
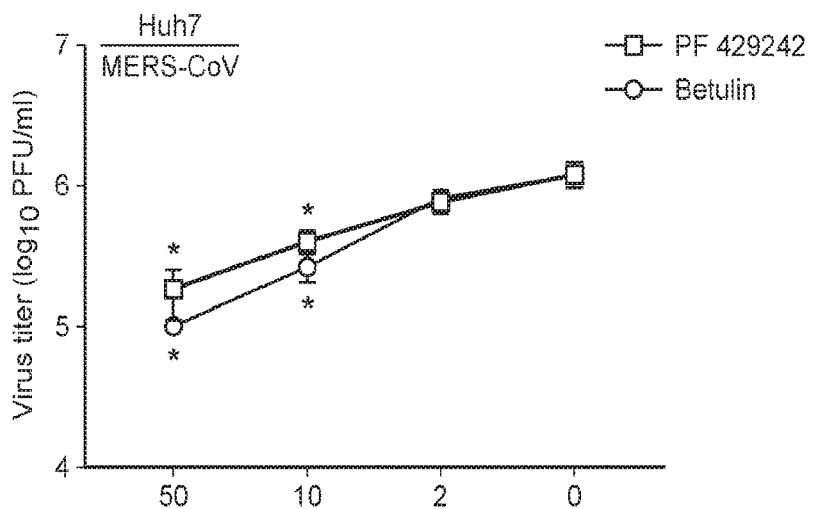
FIG. 57.

Maturation of SREBPs is induced by association with SREBP cleavage activating protein (SCAP) as well as the sequential cleavage of site-1 protease (S1P) and site-2 protease (S2P). Inventors believe that blockade of SREBPs maturation can be effective for antiviral therapy. To this end, Inventors characterized the anti-MERS-CoV activity of betulin (a SCAP inhibitor) and PF429242 (an S1P inhibitor). Both compounds reduced MERS-CoV replication in a dose-dependent manner, achieving about 1 log PFU/ml reduction in viral titer when using 50 μM for the treatment of MERS-CoV-infected Huh7 cells (see FIG. 57). The Inventors believe that these results are indicative of an important and/or indispensable role for SREBPs in MERS-CoV-induced metabolic reprogramming. Additionally, the processing steps of n-SREBPs can provide drug-modifiable molecular targets for suppressing virus replication.

Figure 56:
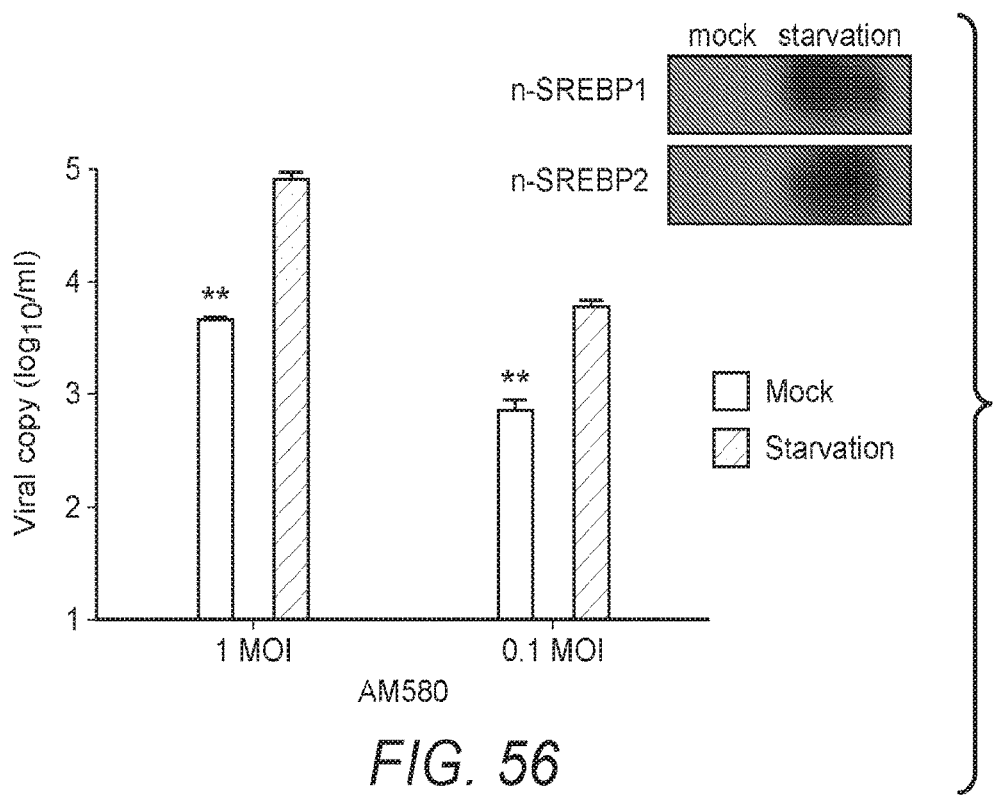
FIG. 56.
Figure 58:
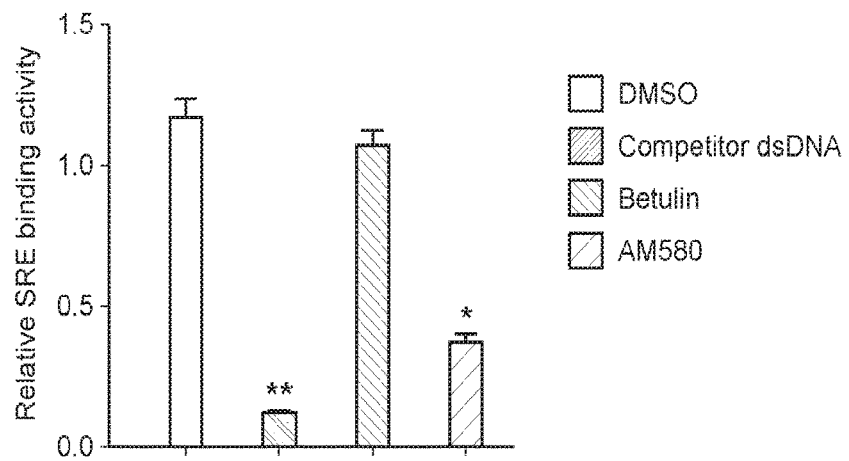
FIG. 58.
Figure 59:
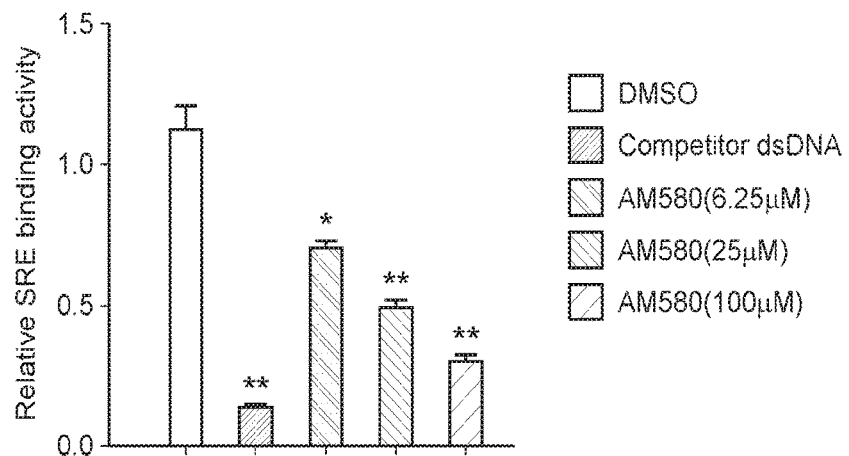
FIG. 59.

The observation that increased n-SREBPs diminished the antiviral potency of AM580 led the Inventors to speculate that AM580 and related compounds can function through binding to n-SREBP (see FIG. 56). Nuclear SREBPs upregulate gene expression of a group of lipogenic enzymes by binding to SREs that are present in the promoters for the genes, such as HMGCS, HMG-CoA reductase, FAS, ACC and squalene synthase [29]. To determine if AM580 and related compounds can interrupted such interactions the DNA binding activities of n-SREBPs were characterized. Specific double stranded DNA (dsDNA) sequences including SREBP1- or SREBP2-binding elements were immobilized onto test wells, and the extent of binding of nuclear-extracted SREBP1 or SREBP2 was then characterized in the presence or absence of candidate inhibitors. Surprisingly, AM580 inhibited binding of both n-SREBP1 and n-SREBP2 with their corresponding SREs (see FIGS. 58 and 59).

Figure 60:
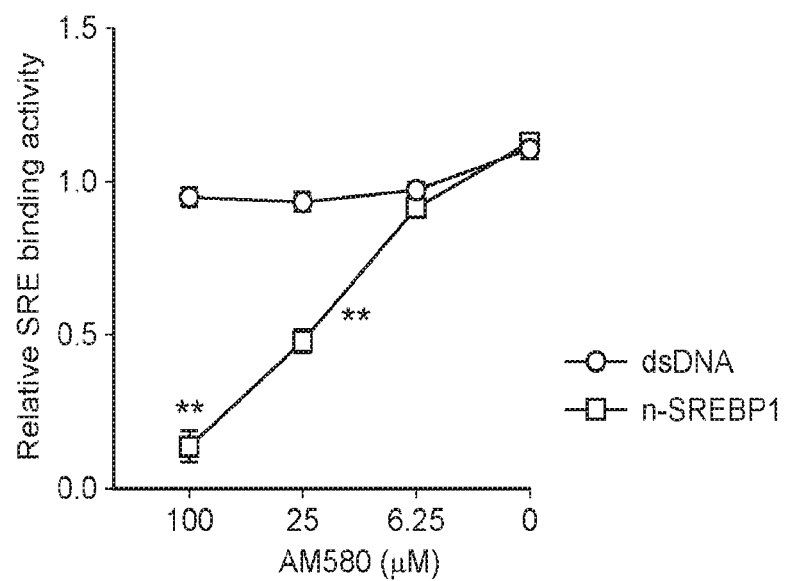
FIG. 60.

Inventors also investigated the mechanism for AM580 inhibition of n-SREBP binding. To determine whether AM580 targeted n-SREBP or SRE, Inventors pre-incubated the drug compound either: (1) with the immobilized dsDNA before adding n-SREBP, or (2) with n-SREBP before binding with the dsDNA. Using n-SREBP1 as an example, AM580 was found to bind with n-SREBP1 rather than SRE, and was found to inhibit the DNA binding activity of n-SREBP1 in a dose-dependent fashion (see FIG. 60).

Figure 62:
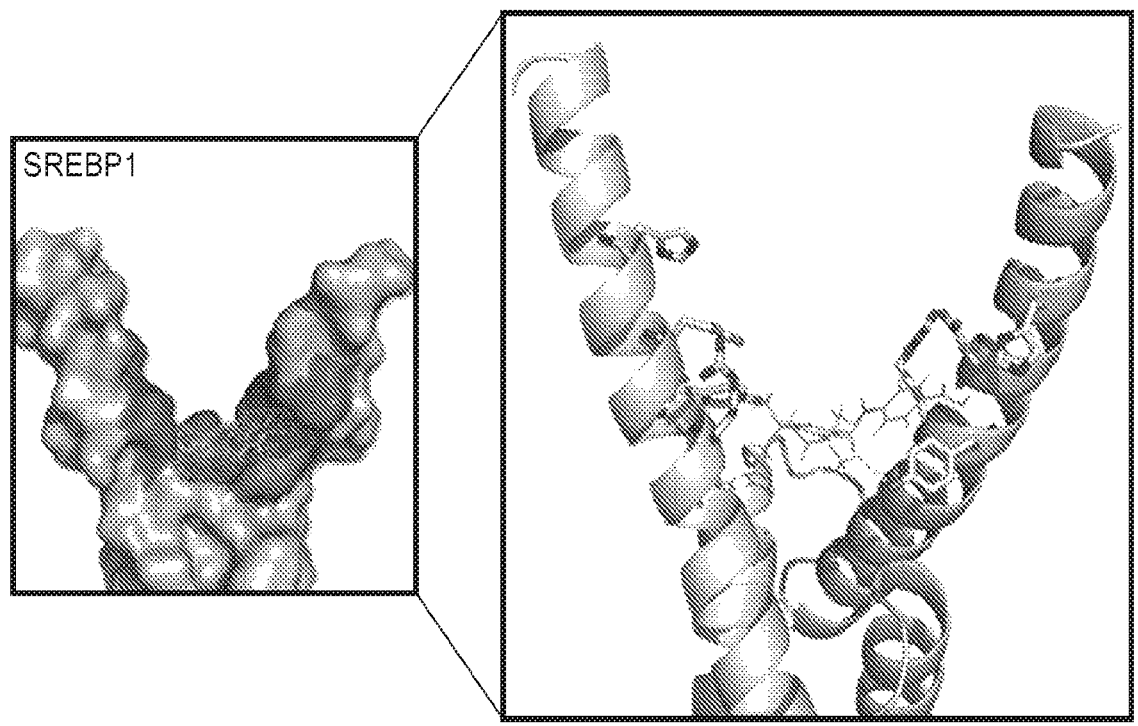
FIG. 62.
Figure 61:
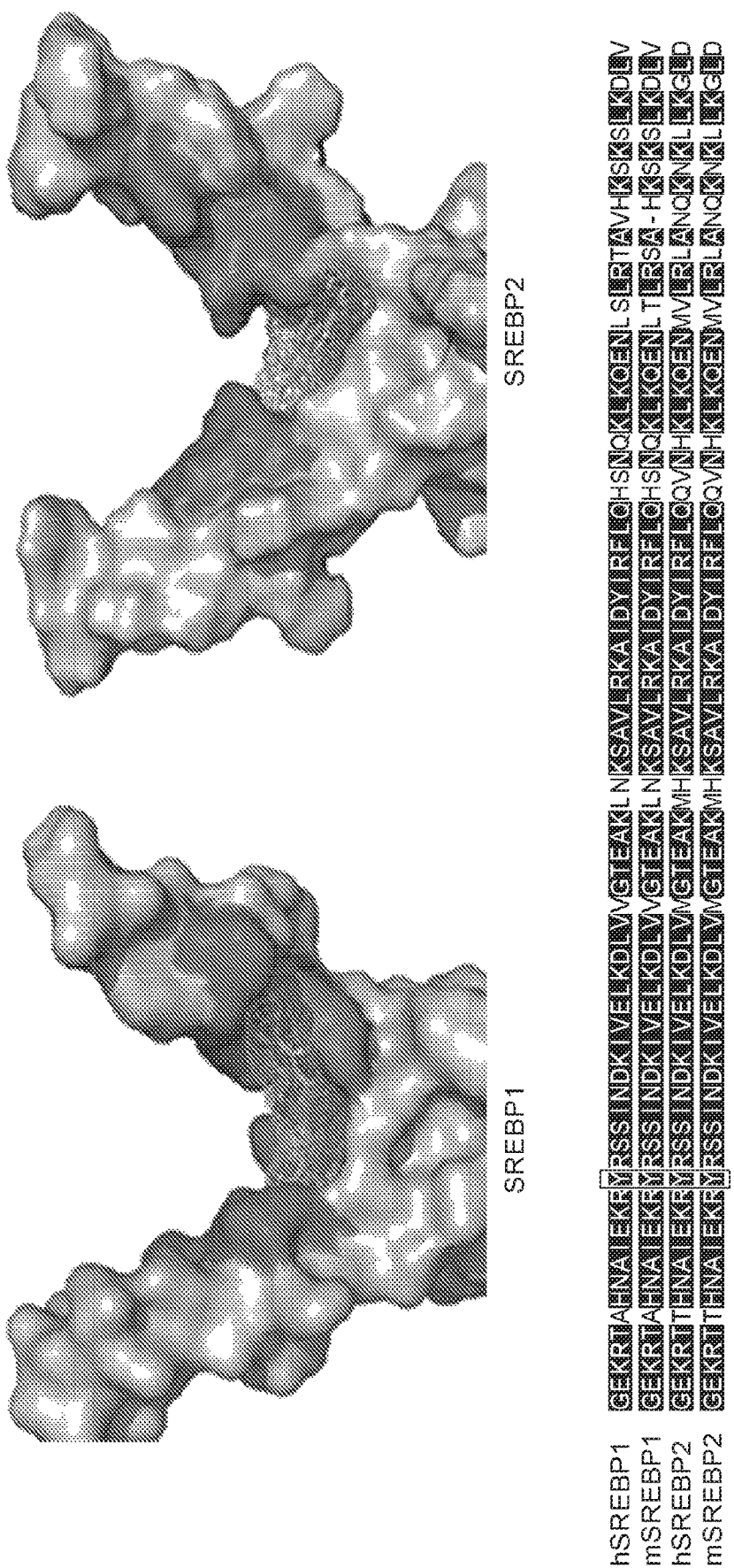
FIG. 61.

To predict the potential amino acid residue(s) that AM580 might interact with, Inventors performed molecular docking analysis using the published crystal structures of SREBP1 and SREBP2[30, 31]. AM580 was predicted to interact with residue Tyr335 (see FIGS. 61 and 62), which is located within the DNA-binding domain and determines SRE recognition [30]. It should be appreciated that the SRE recognition sites of both SREBP1 and SREBP2 are highly conserved between human and mouse (see FIG. 61), which can explain the consistent antiviral activities that Inventors observed across various cell lines, human organoids, ex vivo tissues, and mouse models. Without wishing to be bound by theory, Inventors believe that AM580 inhibits the DNA binding activity of SREBPs by blocking SRE recognition sites.

Figure 63:
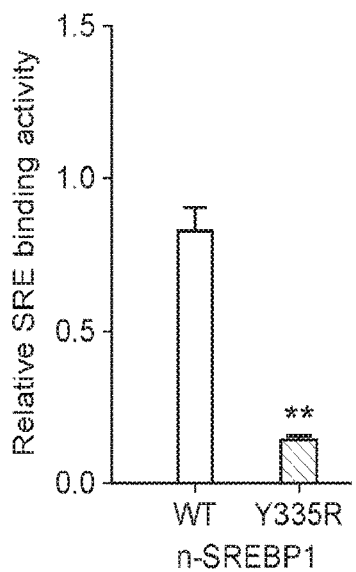
FIG. 63.
Figure 64:
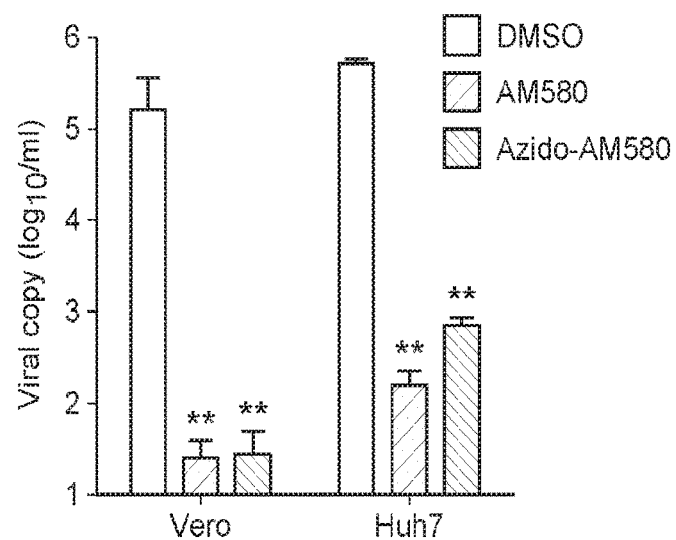
FIG. 64.
Figure 65:
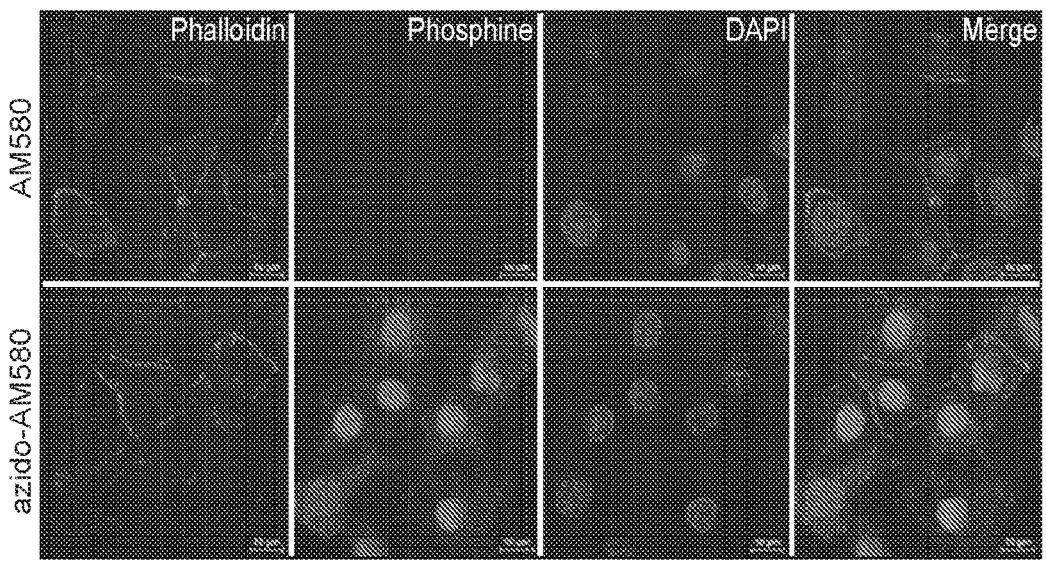
FIG. 65.
Figure 66:
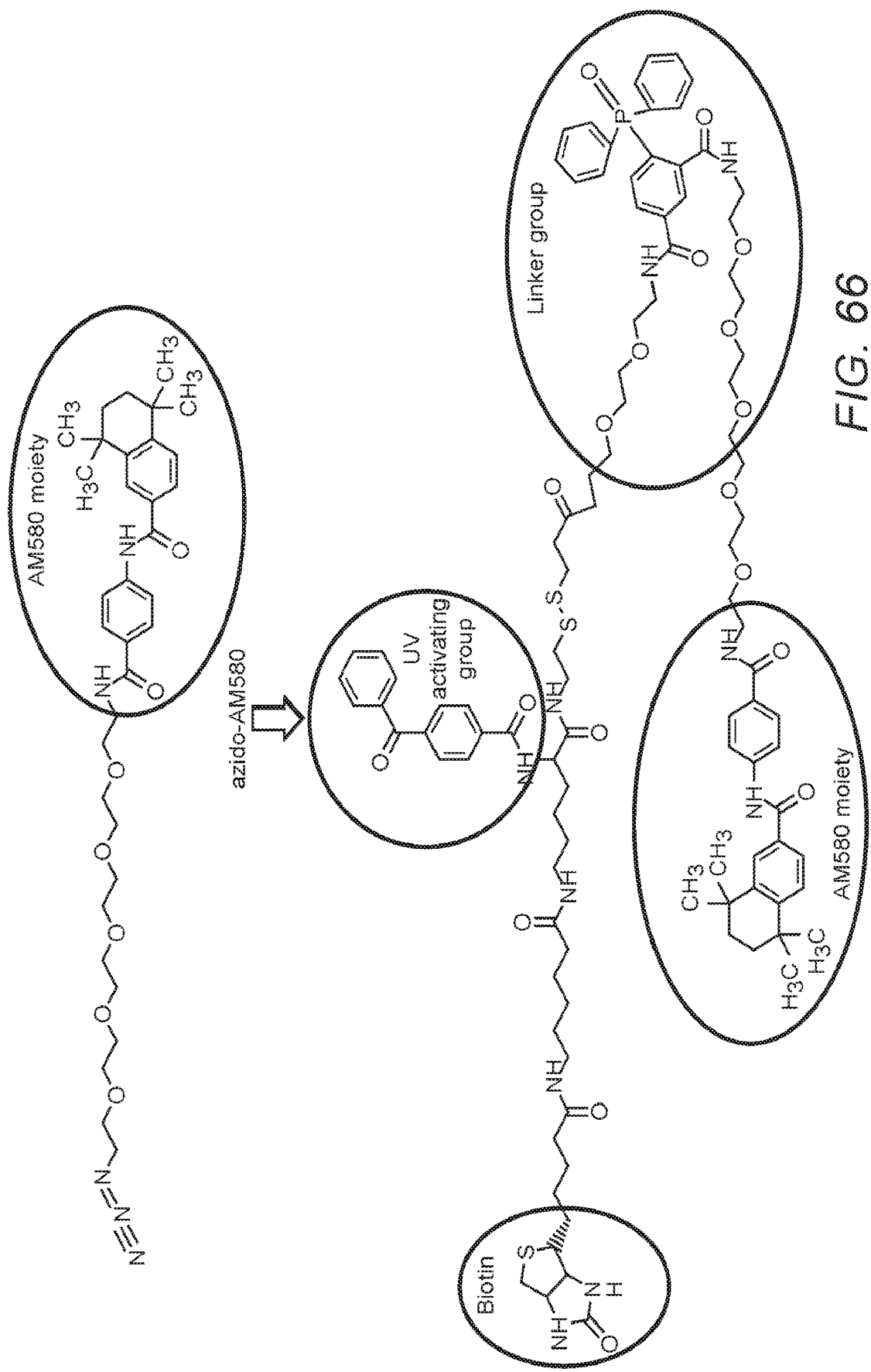
FIG. 66.

To determine if Tyr335 was the AM580-SREBP interaction site (or at least a portion of the interaction site), Inventors performed site-directed mutagenesis to construct a Y335R mutant n-SREBP1, and assessed the binding affinity of WT and Y335R n-SREBP1 against either AM580 or SRE. DNA binding activity of n-SREBP1 was significantly (p<0.01) diminished when Tyr335 was substituted with arginine (see FIG. 63). This indicates that the Tyr335 in n-SREBP1 may be crucial to binding to AM580. To compare the binding affinity of AM580 against WT and Y335R n-SREBP1, an AM580-derived probe (AM580dp) was synthesized. Prior to the synthesis of AM580dp, Inventors introduced a linker arm containing an azido moiety to the carboxylic acid group of AM580 to yield azido-AM580, which was designed for future addition of chemical groups with specific and/or additional probing functions. Similar to AM580, azido-AM580 was found to inhibit MERS-CoV replication in Huh7 and Vero cells (see FIG. 64). Using an azido-reactive green fluorescent dye, azido-AM580 was visualized to be largely localized in the host cell's nucleus, which is consistent with previous conclusions that AM580 targets a lipogenic transactivation event (see FIG. 65). AM580dp contains both a photoaffinity group and a biotin tag (see FIG. 66).

Figure 67:
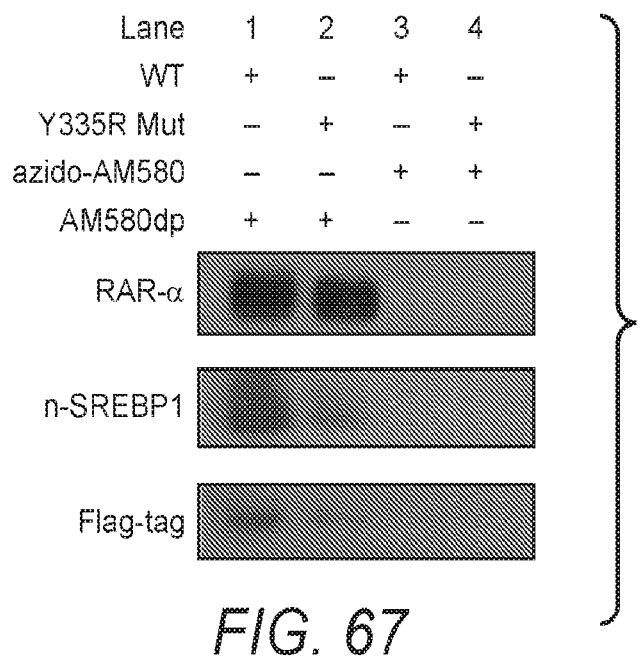
FIG. 67.

To capture the binding target, AM580dp was immobilized on streptavidin-conjugated agarose by its biotin group and incubated with the exogenously expressed WT and Y335R n-SREBP1, respectively. After ultraviolet (UV) irradiation to activate the non-specific crosslinking group in AM580dp based on click chemistry, the protein-AM580dp complex was fixed and pulled down together through biotin-tag purification. On characterization by Western blotting equal amounts of RAR-α were precipitated by WT and mutant Y335R n-SREBP1, indicating that AM580dp was biologically functional (see FIG. 67). Significantly more WT n-SREBP1 was pulled down than Y335R n-SREBP1, suggesting a much higher binding affinity between AM580 and WT n-SREBP1 than between Am580 and Y33R n-SREBP1 (see FIG. 67). Without wishing to be bound by theory, Inventors believe that AM580 targets n-SREBP1 at least in part due to interaction with residue Tyr335.

Figure 68:
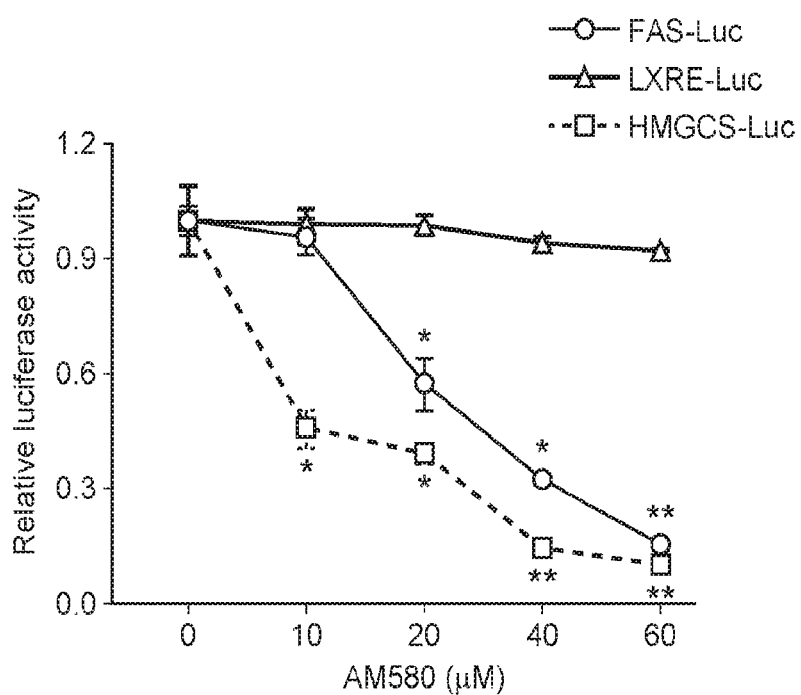
FIG. 68.
Figure 69:
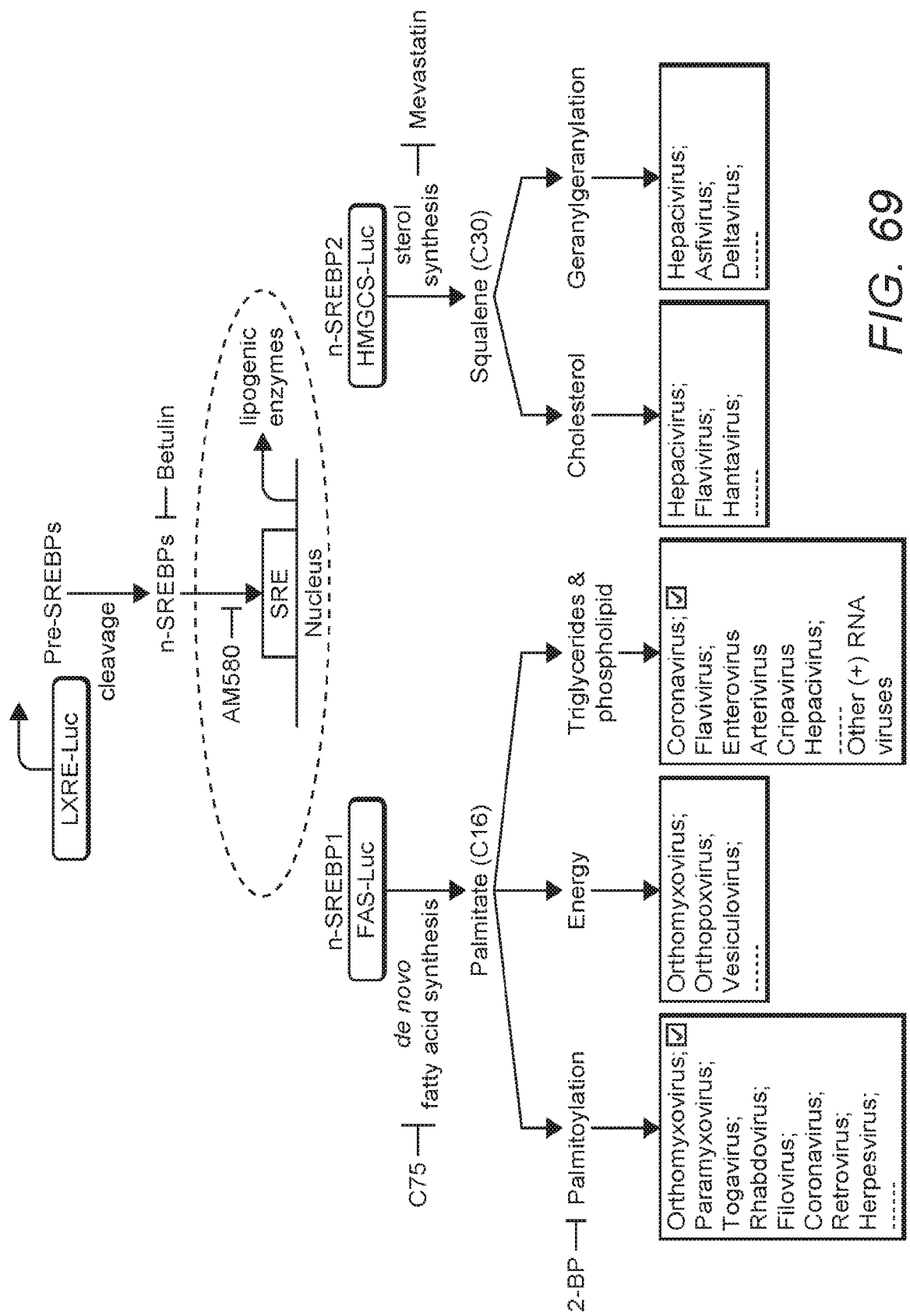
FIG. 69.
Figure 70:
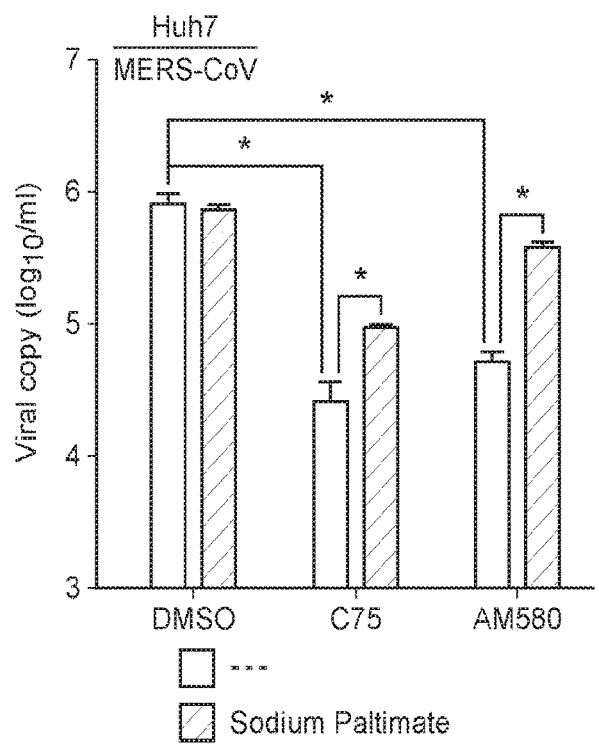
FIG. 70.

SREBPs regulate lipid homeostasis by controlling the expression of enzymes in the lipogenesis pathways, such as HMGCS and FAS. To determine if AM580 can inhibit SREBP-dependent transcriptional activation, two reporter constructs were prepared, HMGCS-promoter-Luc and FAS-promoter-Luc. The former includes a hamster HMGCS promoter sequence (−324/−225) [32] while the latter was includes with a FAS-promoter [33]. AM580 exhibited concentration-dependent inhibition of the reporter gene activities, indicating that lipogenic enzymes such as HMGCS and FAS were blocked at a transcriptional level (see FIG. 68). To confirm the correlation between AM580's anti-MERS-CoV activity and decreased lipid biosynthesis, Inventors characterized the ability of an end-product of the de novo fatty acid biosynthetic pathway, sodium palmitate (see FIG. 69), to reverse the antiviral activity of AM580. In these studies a known FAS inhibitor (C75) was used as a positive control. Notably, both C75 and AM580 showed anti-MERS-CoV activity (FIG. 70). Addition of sodium palmitate did not affect the virus yield in MERS-CoV-infected cells treated with DMSO, but increased the virus yield (p<0.05) in MERS-CoV-infected cells treated with either AM580 or C75 (see FIG. 70). This suggests that AM580 inhibits MERS-CoV replication at least in part by undermining fatty acid synthesis.

Figure 71:
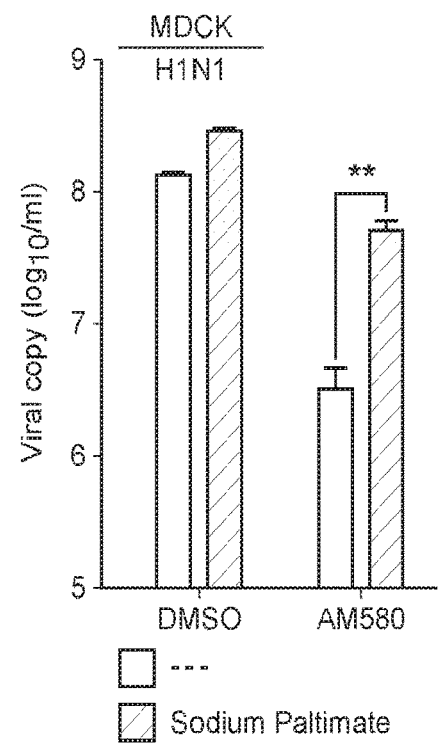
FIG. 71.
Figure 72:
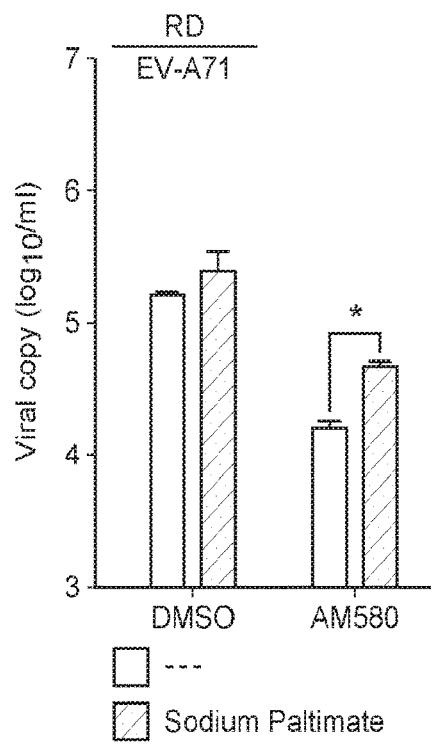
FIG. 72.
Figure 73:
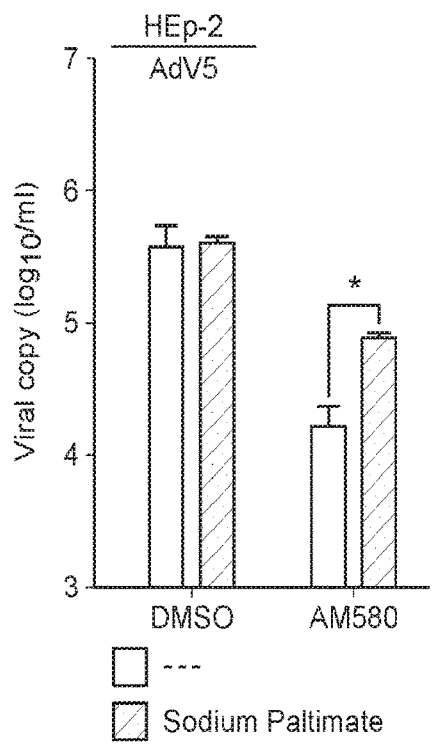
FIG. 73.

Inventors also explored whether fatty acid synthesis was critically involved in the replication of the other viruses that could be inhibited by AM580. To this end, replication rescue assays using influenza A(H1N1)pdm09 virus (negative-strand RNA virus), EV-A71 (non-enveloped RNA virus), and AdV5 (DNA virus) were performed (see FIGS. 71 to 73). Significant (p<0.05) extents of rescue were achieved for these viruses on the addition of 100 μM sodium palmitate. Among them, influenza A(H1N1)pdm09 virus showed the highest dependence on fatty acid synthesis (p<0.01). Overall, these data demonstrate that the broad-spectrum antiviral activity of AM580 and its analogs is at least in part related to the ability to reprogram the lipid metabolic flux.

Figure 74:
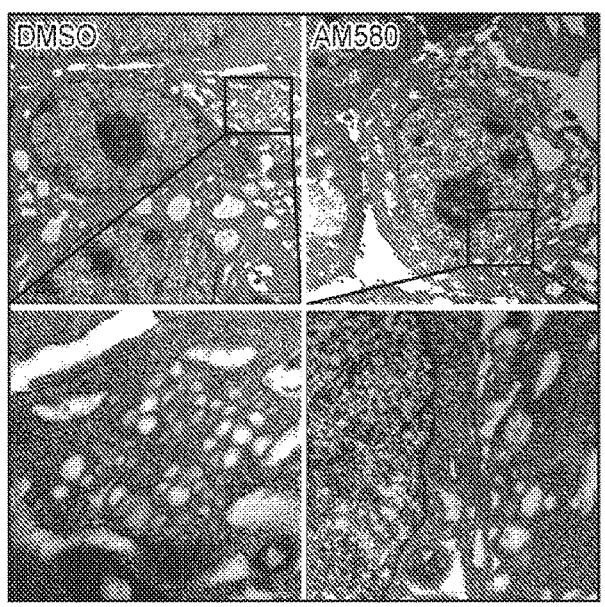
FIG. 74.

Positive-sense RNA viruses are known to replicate their genomes on intracellular membranes. In the case of MERS-CoV, double-membrane vesicles (DMVs) and other replicative organelles (ROs) provide the anchoring scaffold for viral replication/transcription complexes (RTCs). To determine if these virus-induced vesicles can serve as specific targets in the blocking of fatty acid synthesis by AM580 and similar compounds Inventors used MERS-CoV-induced DMVs as a representative study model. Perinuclear DMV clusters were readily detectable in MERS-CoV-infected cells (left panel, FIG. 74) by electron microscopy. In contrast, no DMVs were noted following treatment with AM580 (right panel, FIG. 74). Without wishing to be bound by theory, Inventors believe that AM580 and related compounds can inhibit viral replication at least in part by impeding the formation of DMVs.

Figure 75:
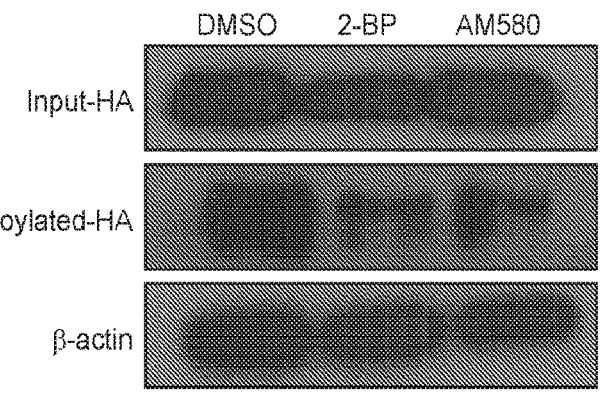
FIG. 75.

Negative-sense viruses (such as influenza A viruses) utilize a different mechanism of genome replication and transcription that is independent of intracellular membranes. Palmitate has several biological functions, including palmitoylation. Palmitoylation is the post-translational attachment of fatty acids that modulate protein function and protein localization [34]. In influenza A viruses, the best characterized viral palmitoylated protein is the surface glycoprotein hemagglutinin (HA) [35]. Palmitoylation levels with or without treatment with AM580 were characterized to determine if blockade of fatty acid synthesis impedes influenza HA palmitoylation and, as a result, arrests post-translational steps of the virus life cycle. HA-overexpressing A549 cells were cultured with AM580, vehicle/control (DMSO), or the positive control inhibitor 2-BP, which specifically impairs palmitoylation by inhibiting palmitoyl acyl transferases palmitate [36]. S-palmitoylated HA protein was purified via resin-assisted capture. No significant difference in the amount of total HA protein was detected among the different treatment groups, suggesting that 2-BP and AM580 had no impact on protein synthesis (see FIG. 75).

Figure 76:
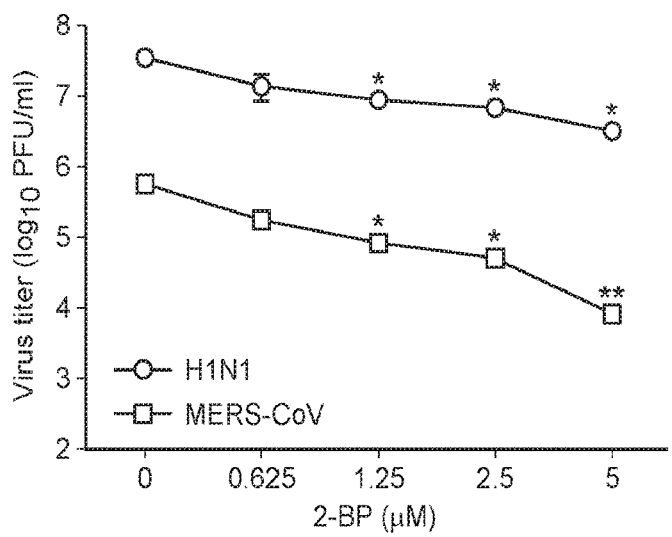
FIG. 76.

Reduced levels of palmitoylated-HA were observed with the addition of 2-BP and AM580, indicating decreased viral protein palmitoylation. Addition of 2-BP post-virus-entry exhibited 1 log 10/ml decrease in influenza A(H1N1)pdm09 viral titer in the supernatant when compared with the DMSO-treated control (see FIG. 76). Without wishing to be bound by theory, Inventors believe that AM580 inhibits SREBP-dependent pathways to impair viral palmitoylation and reduce influenza A(H1N1)pdm09 virus replication. Surprisingly, 2-BP also inhibited MERS-CoV replication in a dose-dependent manner (see FIG. 76), indicating that viral palmitoylation might be another important broad-spectrum antiviral target.

Figure 55:
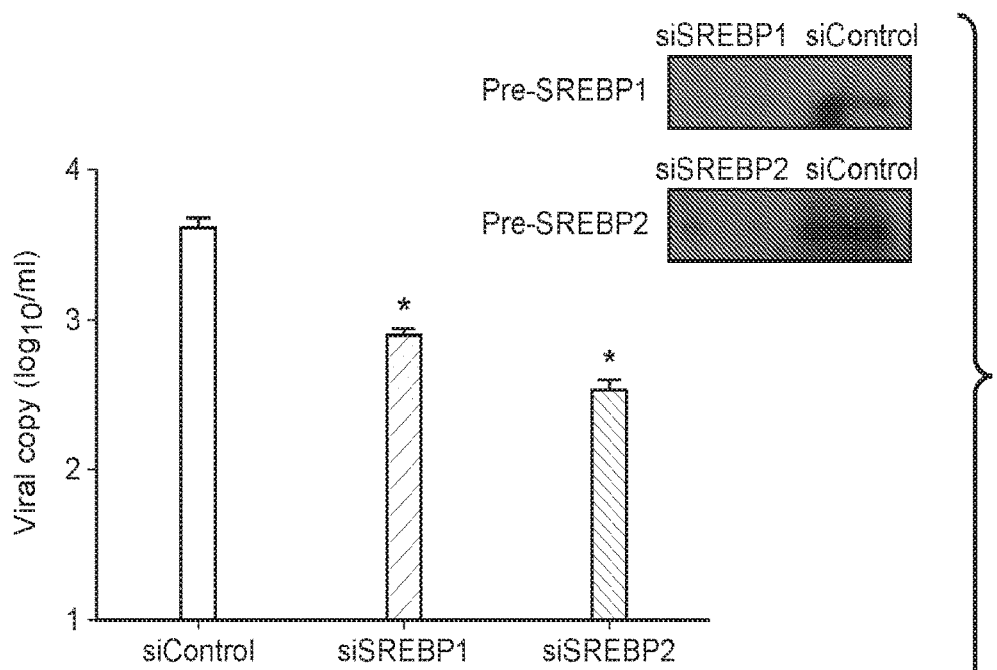
FIG. 55.

Viruses rely on the metabolic network of their cellular hosts to provide energy and building blocks for their replication. The remarkable antiviral efficacy of AM580 and related compounds through the inhibition of SREBP related pathways, in vitro and in vivo, indicates that reprogramming of host lipid metabolism is crucial in multiple aspects of virus life cycle, and importantly, demonstrates that these steps are vulnerable and represent pharmaceutically addressable molecular targets for antiviral intervention. Inventors have found that SREBPs are essential in coordinating virus-induced lipid hyper-induction (see FIG. 55), which consequently affects DMV biosynthesis (see FIG. 74) and post-translational protein palmitoylation (see FIG. 75). In the scenario of virus infection, AM580 down-regulates the genes in cholesterol and fatty acid biosynthesis and decreases the content of cellular lipids to restrict viral replication (see FIGS. 52 and 53). Prior to the proteolytic processing of SREBPs, pre-SREBPs are initially synthesized as ER trans-membrane proteins[19]. When sterol is low, SCAP escorts SREBP from ER to Golgi apparatus, where SREBP is sequentially cleaved by proteases S1P and S2P so that n-SREBP is released and transported to nucleus to transactivate gene expression. When cellular sterol level is high, however, cholesterol or oxysterols stimulate the association between SCAP and Insulin-induced gene 1 protein (INSIG1), causing the ER retention of SCAP-SREBP complex and thereby reducing n-SREBP and decreasing the expression of genes involved in lipid metabolism. Inventors have shown that AM580 transcriptionally inhibits multiple lipogenic enzymes via blockage of the binding between n-SREBPs and SRE (see FIGS. 59 and 61). Targeting to an earlier event, Tang and colleagues identified betulin that inhibits SREBPs by promoting the ER-retention of SREBP [28]. Indeed, both betulin and an inhibitor of S1P activity displayed inhibition of viral replication (see FIG. 57). Overall, Inventors have identified proteolytic processing of SREBPs as feasible targets for broad-spectrum antivirals.

Regulated by SREBPs, lipogenic enzymes involved in cellular lipid metabolism have been suggested to play an important role in host-virus interaction [37], which is consistent with Inventor's findings. Indeed, pharmacological inhibition of FAS by C75 has resulted in impaired replication of flavivirus [38] and vaccinia virus [39]. Using C75 as a positive control, Inventors demonstrated that AM580 inhibition of divergent viruses, enveloped (MERS, influenza) and non-enveloped (EV-A71), RNA or DNA (AdV5) virus, could be partially rescued by exogenous palmitate (see FIGS. 71 to 74). Results of such studies show the indispensability of lipid biosynthesis (particularly de novo fatty acid synthesis) for optimal and/or maximal viral replication. This also explains the observed broad-spectrum antiviral potency of AM580 across different cell lines, mouse models, human organoids and ex vivo models (see FIGS. 7 to 12, 15 to 22, 24, and 27 to 31). Inventors believe that, after transcriptional inactivation by AM580, the silencing of lipogenic enzymes other than FAS can also contribute to the impaired virus replication (see FIG. 69). As shown above, a palmitoylation inhibitor (2-BP) exhibited antiviral activity against both influenza A(H1N1) virus and MERS-CoV, suggesting that viral protein palmitoylation is another pharmaceutically addressable host molecular target for broad-spectrum antivirals (see FIG. 44). Functioning as a raft-targeting signal, palmitoylation is a common and conserved biological process essential in virus assembly and budding. Prominent examples reported for human pathogens include surface glycoproteins such as the HA of influenza A virus, NB of influenza B virus, the fusion (F) protein of measles virus, the glycoproteins of filoviruses and retroviruses (including HIV)[34]. Protein palmitoylation also regulates functions of cellular proteins. Thus it is important to weigh anticipated efficacy versus side effects before the development of palmitoylation inhibitors as antiviral therapeutics. Discovery of the DHHC protein family sheds lights along this way [40]. DHHC protein catalyzes palmitoylation with different substrate specificities, suggesting that these proteins might be promising drug targets since their blockade should result in suppression of viral replication, while acylation of cellular proteins will not be compromised [41].

Figure 32:
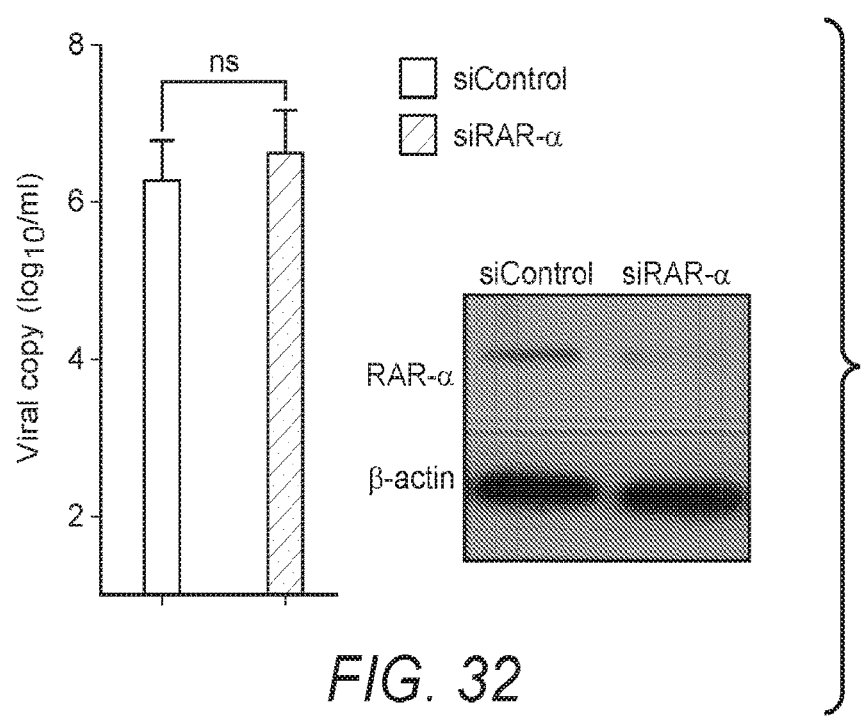
FIG. 32.
Figure 33:
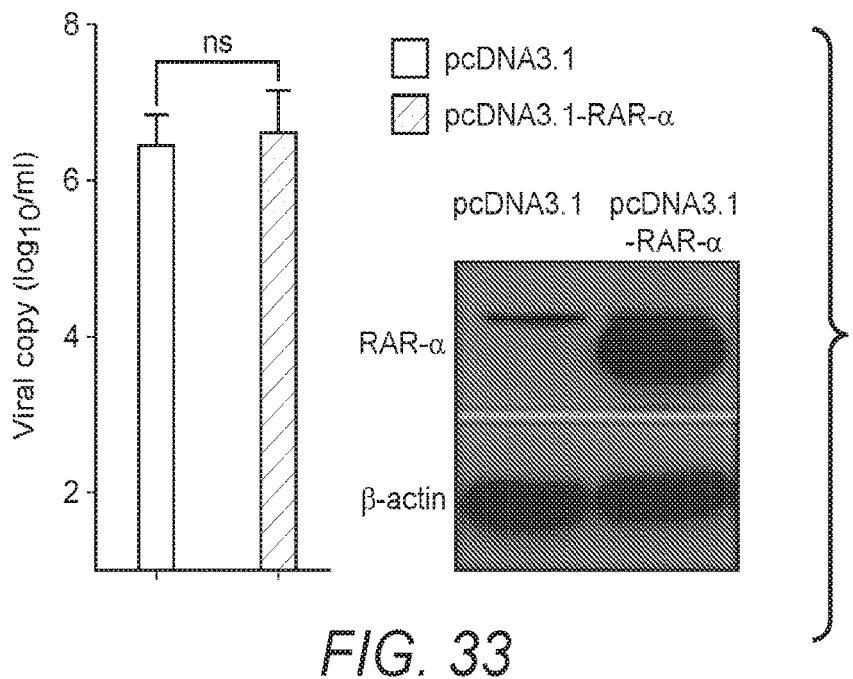
FIG. 33.
Figure 34:
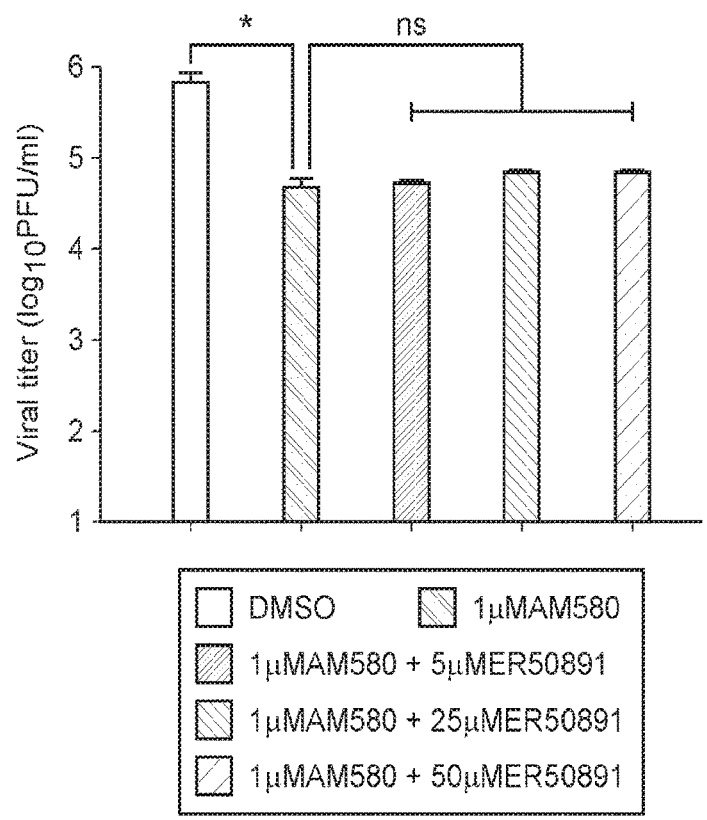
FIG. 34.
Figure 35:
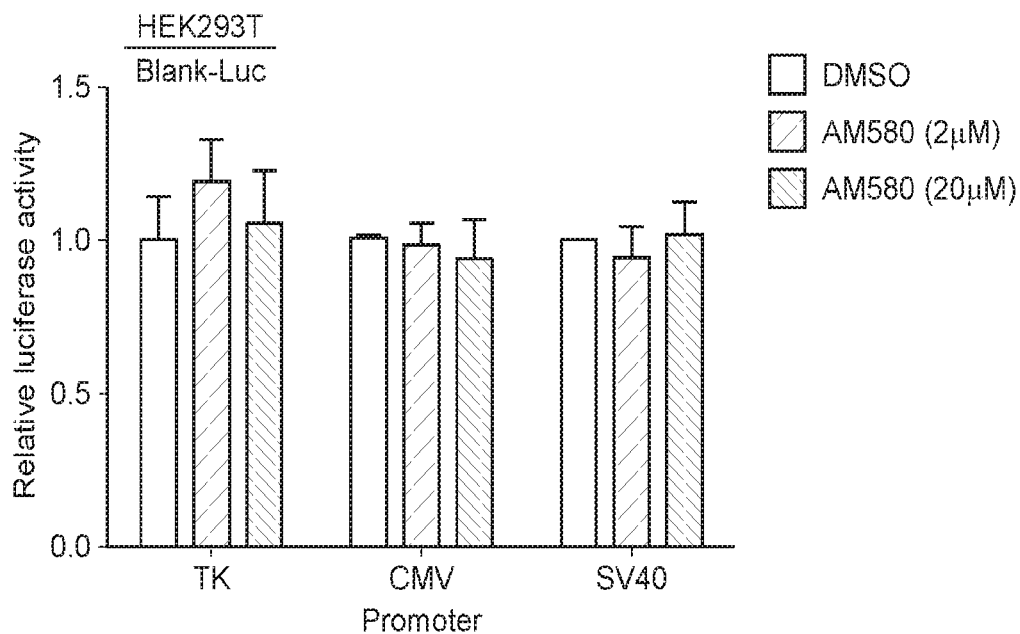
FIG. 35.

Surprisingly, the antiviral activity of AM580 is not dependent on the RAR-α pathway (see FIGS. 32 to 34). Structure-activity analysis of AM580 guided proper modification of azido-AM580 and AM580dp, which enabled the visualization of its cellular distribution (see FIG. 65) and pull-down of SREBP as a direct binding target of AM580 (see FIG. 68). Knockdown of SREBP1 or 2 did not exhibit similar level of antiviral potency as that of AM580 (see FIG. 55), which might be due to that SREBP1 and SREBP2 can compensate for each other when one protein was impaired [42]. Although the teratogenic effects of AM580 in mouse models has been reported [43] the anticipated therapeutic benefits outweigh the risk of such side effects, particularly when considering the short duration of 3 days of treatment by AM580 in the animal experiments. In exploring AM580 analogs with comparable potency and improved bioavailability, Tamibarotene, an orally active retinoid for treatment of acute promyelocytic leukemia was identified [44]. It should be appreciated that Tamibarotene has a known and comprehensive safety profile, and is a marketed product in Japan. With the clinical tolerability success of Tamibarotene, Inventors believe AM580 and/or related compounds can be modified as a safe and broad antiviral therapeutic, particularly since AM580 is active only during the burst of heightened lipid demand is triggered by virus infection.

EXAMPLES

Cells and viruses: Human embryonic kidney (HEK293T) cells, human lung carcinoma (A549) cells, human hepatoma (Huh7) cells, human rhabdomyosarcoma (RD) cells, human epithelial type 2 (HEp-2) cells, human lung adenocarcinoma (Calu-3) cells, human leukemic (THP-1) monocytes, Madin-Darby canine kidney (MDCK) cells, African green monkey kidney (Vero) cells, and Vero-E6 cells were obtained from ATCC and maintained in culture medium as suggested by the supplier/manufacturer. Human peripheral blood monocyte-derived macrophages (MDMs) were isolated from healthy adult blood samples collected from Hong Kong Red Cross Blood Transfusion Service according to a protocol approved by the Institutional Review Board of the University of Hong Kong. Monocyte preparation and differentiation were performed according to a well-established protocol as Inventors described previously[45]. All cell lines were cultured at 37° C. in 5% $CO_2$. All cell lines used in the study were confirmed to be free of mycoplasma contamination as determined by Plasmo Test (InvivoGen). Upon virus infection, the infected cells were maintained in FBS free medium with or without compounds. The Influenza A virus strain A/Hong Kong/415742/2009(H1N1)pdm09 was cultured in MDCK cells. The MERS-CoV (HCoV-EMC/2012) and SARS-CoV (GZ50) were propagated in Vero-E6 cells. A clinical isolate of ZIKV (Puerto Rico strain PRVABC59) was amplified in Vero cells. The Enterovirus A71 (SZ/HK08-5) was cultured in RD cells. A clinical isolate of human adenovirus type 5 (AdV5) was propagated in A549 cells. Two mouse-adapted virus strains, A/Anhui/1/2013 (H7N9) and MERS-CoV (HCoV-EMC/2012) were used for in vivo antiviral tests. All cultured viruses were titrated by plaque forming unit assays (plaque assay) and/or 50% tissue culture infectious dose ($TCID_{50}$) assay as Inventors previously described with slight modifications [46]. All virus stocks were kept at −80° C. in aliquots. All experiments with live viruses were conducted using biosafety level 2 or 3 facilities as Inventors described previously [47].

Chemical reagents and antibodies: AM580 was purchased from Cayman Chemical (Michigan, United States), while other chemical inhibitors were obtained from Sigma-Aldrich (Missouri, United States) unless specified. MERS-CoV NP was detected with the guinea pig anti-MERS-CoV NP serum as Inventors previously described [48]. Primary antibodies against human RAR-α (Abcam), SREBP1 (Santa Cruz), SREBP2 (Santa Cruz), n-SREBP1 (Novus Biological), n-SREBP-2 (Novus Biological), Flag-tag (Sigma) were purchased and used in relevant experiments. Alexa Fluor 488 goat anti-pg IgG (H+L) antibody (Invitrogen) was utilized as secondary antibody for immunofluorescence staining. 4',6-diamidino-2-phenylindole (DAPI, Sigma) and Phalloidin-Atto 647N (Sigma) was used for nuclear and cell membrane staining, respectively. Silencer Select human SREBP1 siRNA, Silencer Select human SREBP2 siRNA, and Silencer Select siRNA negative control were obtained from Life Technologies. Fluorescent neutral lipid dye 4,4-difluoro-1,3,5,7,8-pentamethyl-4-bora-3a,4a-diaza-s-indacene (BODIPY 493/503, Invitrogen) was used to stain lipid droplets (LDs), while Filipin III (Cayman chemical) was employed for visualization of intracellular cholesterol. The phosphine-activated fluorescent dye DyLight™ 488-Phosphine (Invitrogen) was utilized for specific labeling and detection of azide-tagged molecule, i.e. Azido-AM580.

Plasmids: FAS promoter luciferase was a gift from Dr. Bruce Spiegelman (Addgene plasmid #8890), pSynSRE-T-Luc containing HMG-CoA synthase promoter (Addgene plasmid #60444), pcDNA3.1-2×FLAG-SREBP-2 (Addgene plasmid #26807), pcDNA3.1-2×FLAG-SREBP-1c (Addgene plasmid #26802) were gifts from Dr. Timothy Osborne. The luciferase constructs IFNβ-Luc and ISRE-Luc were provided by Dr. Dong-yan JIN (The University of Hong Kong).

Primary screening: A compound library containing 189 bioactive-lipids (Cayman Chemical, Michigan, USA) was purchased for screening. The library collection included prostaglandins, receptor agonists and antagonists, and ceramide derivatives, which is ideal for G protein-coupled receptor screening and for routine pharmacological screening. An MTT-based CPE inhibition assay was performed as Inventors previously described with slight modifications [49]. To identify anti-MERS-CoV inhibitors, confluent Huh7 cells in 96-well culture plates ($4\times10^4$ cells/well) in triplicate were infected with MERS-CoV at 0.1 multiplicity of infection (MOI). One hour after virus absorption, the inoculum was removed, followed by addition of drug-containing medium (10 µM). Twenty-four hours later, 100 of 5 mg/ml MTT solution (Sigma) were added to the wells. The monolayers were incubated as above for 4 hours. Finally, 1000 of 10% SDS with 0.01M HCl was added and further incubated at 37° C. with 5% $CO_2$ overnight. The activity was read at 570 nm with reference wavelength at 640 nm. To screen anti-influenza-virus inhibitors, MDCK cells were infected with influenza virus A(H1N1)pdm09 virus at 0.01 MOI, while the time-point for scoring of cell viability was 48 hours post-infection (hpi). Other procedures were same as above. Next, a dose-response analysis using plaque reduction assay (PRA) [50] was performed to evaluate the in vitro antiviral efficacies of the primary hits, in which individual compound was serially-diluted (10, 5, 2.5, 1.25, and 0.625 µM) and tested for either MERS-CoV or influenza A(H1N1) virus inhibition.

Selectivity index: Selectivity index (SI) of each compound was calculated as the ratio of 50% cellular cytotoxicity concentration ($CC_{50}$) over 50% inhibitory concentration ($IC_{50}$). The $CC_{50}$ value was determined with an MTT assay (Invitrogen) and CellTiter-Glo assay (Promega)

according to the manufacturer's protocols, while $IC_{50}$ data was obtained with plaque reduction assay or by viral load reduction assay as indicated [51]. Both $CC_{50}$ and $IC_{50}$ were calculated using GraphPad Prism 6.

Flow Cytometry: For intracellular staining, cells were detached with 10 mM EDTA in PBS, fixed in 4% paraformaldehyde, and permeabilized with 0.1% Triton X-100 in PBS. Immunostaining for flow cytometry was performed following standard procedures as Inventors described previously [52]. The flow cytometry was performed using a BD FACSCanto II flow cytometer (BD Biosciences) and data was analyzed using FlowJo vX (Tree Star).

Animal experiments: Human dipeptidyl peptidase 4 (DPP4) transgenic C57BL/6 mice and BALB/c female mice were kept in biosafety level 3 housing and given access to standard pellet feed and water ad libitum. All experimental protocols were approved by the Animal Ethics Committee in the University of Hong Kong and were performed in compliance with the standard operating procedures of the biosafety level 3 animal facilities. MERS-CoV and influenza virus A(H7N9) were tested in DDP4 mouse model [23] and BALB/c mouse model [47] as Inventors previously described, respectively. To examine the anti-MERS-CoV activity of AM580, a total of 36 mice (18 mice/group) were evaluated. After anesthesia, mice were intranasally (i.n.) inoculated with 20 μL of virus suspension containing 50 PFU of MERS-CoV. The therapeutic treatment was initiated 6 hours post-virus-challenge by intraperitoneal (i.p.) inoculation. One group of mice was inoculated with 200 μL of AM580 i.p. for 3 days (12.5 mg/kg/day). The second group of mice was administered 200 μL 0.1% DMSO in PBS i.p. as an untreated control. Animal survival and sick signals were monitored for 14 days or until death. Four mice in each group were euthanized randomly on day 2 and 4 post-challenge, respectively. Mouse lungs and brains were collected for virus titration and H&E histopathologic analyses as Inventors described previously [47]. To evaluate the anti-influenza potency of AM580 in vivo, BALB/c mice (18 mice/group) were intranasally (i.n.) inoculated with 20 μL of virus suspension, i.e. 100 PFU of Influenza A(H7N9) virus. The therapeutic treatment was initiated 6 hours post-virus-challenge by i.n. intranasal administration. One group of mice was inoculated with 20 μL of i.n. AM580 (1 mg/kg/day). The second group of mice was treated with 20 μL of i.n. zanamivir (2 mg/kg/day) as a positive control. The third group was given i.n. 0.1% DMSO in PBS as an untreated control. Two i.n. doses per day of AM580, zanamivir or PBS were administered for 3 days (total 6 doses/mouse). Animal survival and sick signals were monitored for 14 days or until death. Lung tissues (4 mice/group) were collected for virus titration and H&E histopathological analyses on days 3 and 6 post-virus-challenge, respectively.

Human intestinal organoid culture and virus infection experiments: Under the protocol approved by Institutional Review Board of the University of Hong Kong/Hospital Authority Hong Kong West Cluster, normal small intestine was obtained from a patient who underwent surgical resection. Intestinal organoids were then cultured and differentiated for MERS-CoV infection as Inventors described elsewhere [23]. An inoculum of $10^5$ PFU of MERS-CoV was used to infect one droplet of intestinoids (containing 50 to 100 intestinoids), with an estimated MOI of 0.1. After the inoculum was removed, the virus-inoculated intestinoids were rinsed with PBS and then re-embedded in Matrigel and cultured in a 48-well plate with culture medium containing or lacking AM580 (20 μM). At the indicated time points, the intestinoids were harvested for the quantification of intracellular viral load, whereas cell-free Matrigel and culture medium were combined for viral titration of extracellular supernatant.

Ex vivo lung tissue culture and virus infection experiments: The ex vivo lung tissue culture and virus infection experiments were approved by the Institutional Review Board of the University of Hong Kong/Hospital Authority Hong Kong West Cluster. Fresh normal lung tissue was obtained from a patient undergoing lung surgical resection. Experimental conditions for virus infection and subsequent immunofluorescence staining were performed as Inventors described previously[45]. Briefly, lung tissue was cut into 2-mm$^3$ cubes and subsequently infected by a MERS-CoV inoculum of $2 \times 10^8$ PFU/ml or were mock-infected for 1 hour at 37° C. After inoculation, tissue cubes were maintained in DMEM/F12 medium supplemented with 10% human serum and penicillin/streptomycin before fixation and cryo sectioning.

Transcriptome analysis: Calu-3 cells were mock infected or infected with MERS-CoV at an MOI of 2 and incubated in DMEM medium containing (or lacking) AM580 (20 μM). At 24 hpi, total RNAs of individual group (n=3) were collected. The altered gene expression following MERS-CoV infection and AM580 treatment were analyzed using RNA-Seq technology[53]. The sequencing libraries were constructed and sequenced by Beijing Genomics Institute (BGI), averagely generating 23,977,722 clean reads after filtering the low quality. Clean reads were mapped to reference using HISAT[54]/Bowtie2 [55]. The differentially expressed genes in MERS-infected samples with or without AM580 treatment were submitted to DAVID server to perform the pathway enrichment and cluster analysis.

Lipidome analysis: Calu-3 cells were mock infected or infected with MERS-CoV at an MOI of 2 and incubated in DMEM medium containing (or lacking) AM580 (20 μM). At 8 and 24 hpi, cells were collected and subjected to cellular lipid extraction, respectively. Inactivation of virus infectivity was confirmed by plaque assay. Sample preparation was performed with minor modifications according to the published paper [56]. Briefly, an ice-cold quenching buffer of 150 mM ammonium bicarbonate was added to dissociate cells, which were then transferred into an anti-chloroform tube. Two milliliter of chloroform/methanol (v/v 2:1) was added to the tube, followed by vortex and centrifuge at 4500 rpm for 10 minutes at 4° C. The bottom phase was collected to glass vials and dried by vacuum concentrators for storage in −80° C. Upon LC-MS analysis, the dried samples were reconstituted in 3000 chloroform/Methanol (v/v 2:1) and analyzed using an Acquity UPLC system coupled to a Synapt G2-HDMS mass spectrometer system (Waters Corp., MA, USA). The chromatography was performed on a Waters ACQUITY BEH C18 column (1.7 μm, 2.1×100 mm, I.D., 1.7 mm, Waters, Milford, MA, USA). The mobile phase consisted of (A) 0.1% acetic acid in water and (B) acetonitrile. The separation was performed at a flow rate of 0.4 ml/min under a gradient program as follows: 0.5% B (0 to 1.5 minutes), 0.5 to 8% B (1.5 to 2 minutes), 8 to 35% B (2 to 7 minutes), 35 to 70% B (7 to 13 minutes), 70 to 99.5% B (13 to 29 minutes), 99.5% B (29 to 36 minutes). The mass spectral data were acquired in both positive and negative modes. Leucine encephalin was used as a lock mass for all experiments. Collision energy was used with the range from 20 to 40 eV for fragmentation to allow putative identification and structural elucidation of the significant metabolites.

Electron microscopy: Electron microscopy was utilized to observe double-membrane vehicles (DMVs) that induced by MERS-CoV infection. Vero cells were grown a 6-well plate. Following infection with MERS-CoV at an MOI of 3 (or mock infection) for 1 hour, the cell culture medium was replaced with fresh medium containing 20 μM AM580 or 0.1% DMSO as a control. After 12 hours the cell culture medium was removed. The cells were washed with PBS, trypsinized and fixed with 4% formaldehyde for further processing and counterstaining [57]. The images were acquired in Electron Microscope Unit of the University of Hong Kong.

Molecular docking: The crystal structures of SREBP1 (PDB code: 1AM9) and SREBP2 (PDB code: 1UKL) were retrieved from the Protein Data Bank database. SREBP1 dimer and SREBP2 dimer were extracted with Pymol. Missing residues in SREBP2 were modeled using I-TASSER server [58]. Protein models were prepared with the Protein Preparation Wizard module in Maestro [59]. The 3D conformer of AM580 was downloaded from PubChem database [60]. Leadfinder v 1.81 was used to perform the docking simulation with extra precision method [61].

Chemical synthesis: Azido-AM580 was used for intracellular visualization of AM580, while AM580dp was designed and synthesized for pull-down studies of AM580 binding targets.

To synthesize azido-AM580, 20 mg of AM580 was mixed with 3.14 ml of azido-PEGS-amine (Conju-Probe, LLC) (10 mg/ml) dissolved in dimethylformamide (DMF). Next, 1-[Bis(dimethylamino)methylene]-1H-1,2,3-triazolo[4,5-b]pyridinium 3-oxid hexafluorophosphate (HATU), 50 µl of N,N-diisopropylethylamine (DIPEA) and 2.46 ml of dichloromethane (DCM) were added to a final volume 5.7 ml. Reaction was performed at room temperature with shaking. After overnight incubation, the reaction mixture was lyophilized to remove solvent. Azido-AM580 was purified by HPLC and m/z 640 was detected by mass spectrometry (MS). Final yield was quantified by nuclear magnetic resonance (NMR).

To synthesize AM580dp, purified azido-AM580 was linked with an amine reactive tri-functional cross linker (2-{N2-[Nα-Benzoylbenzoicamido-N6-6-biotinamidocaproyl]lysinylamido}ethyl-2'-(N-sulfosuccinimidylcarboxy)ethyl Disulfide Sodium Salt (Santa Cruz), which was a biotin-UV activating-NHS ester compound designated Compound A. This tri-functional cross linker contains a NHS-ester head group for linking to the amine tail of another cross linker phosphine compound (Compound B) (methyl 4-[2-[2-(2-aminoethoxy)ethoxy]ethylcarbamoyl]-2-diphenylphosphanyl-benzoate (Shinsei Chemical Company Ltd.), a biotin head group for Streptavidin resin binding on the other end, and a UV activating benzophenone group for crosslinking with target binding proteins of AM580. Specifically, 1 mg of Compound A was mixed with 300 of 74.8 mM Compound B (dissolved in DMSO-d6) to a final volume of 1 ml by DMF. Molar ratio of Compound A to Compound B was 1:2. The reaction was performed at 40° C. with shaking at 1400 rpm. Excess azido-AM580 was added to the mixture to allow cross-linking with the phosphine group by Staudinger ligation reaction. The reaction product was then incubated with Streptavidin agarose resin (Pierce) to capture the AM580dp product.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

REFERENCES

1. Peiris, J. S., et al., Coronavirus as a possible cause of severe acute respiratory syndrome. Lancet, 2003. 361 (9366): p. 1319-25.
2. Chan, J. F., et al., Middle East respiratory syndrome coronavirus: another zoonotic betacoronavirus causing SARS-like disease. Clin Microbiol Rev, 2015. 28(2): p. 465-522.
3. Yuen, K. Y., et al., Clinical features and rapid viral diagnosis of human disease associated with avian influenza A H5N1 virus. Lancet, 1998. 351(9101): p. 467-71.
4. To, K. K., et al., The emergence of influenza A H7N9 in human beings 16 years after influenza A H5N1: a tale of two cities. Lancet Infect Dis, 2013. 13(9): p. 809-21.
5. De Clercq, E., Strategies in the design of antiviral drugs. Nat Rev Drug Discov, 2002. 1(1): p. 13-25.
6. Zumla, A., et al., Coronaviruses—drug discovery and therapeutic options. Nat Rev Drug Discov, 2016. 15(5): p. 327-47.
7. Simmons, G., et al., Inhibitors of cathepsin L prevent severe acute respiratory syndrome coronavirus entry. Proc Natl Acad Sci USA, 2005. 102(33): p. 11876-81.
8. Kaletsky, R. L., G. Simmons, and P. Bates, Proteolysis of the Ebola virus glycoproteins enhances virus binding and infectivity. J Virol, 2007. 81(24): p. 13378-84.
9. Warren, T. K., et al., Protection against filovirus diseases by a novel broad-spectrum nucleoside analogue BCX4430. Nature, 2014. 508(7496): p. 402-5.
10. Zhu, J. D., et al., Broad-spectrum antiviral agents. Front Microbiol, 2015. 6: p. 517.
11. Burke, J. D., L. C. Platanias, and E. N. Fish, Beta interferon regulation of glucose metabolism is PI3K/Akt dependent and important for antiviral activity against coxsackievirus B3. J Virol, 2014. 88(6): p. 3485-95.
12. Thakur, C. S., et al., Small-molecule activators of RNase L with broad-spectrum antiviral activity. Proc Natl Acad Sci USA, 2007. 104(23): p. 9585-90.
13. Graci, J. D. and C. E. Cameron, Mechanisms of action of ribavirin against distinct viruses. Rev Med Virol, 2006. 16(1): p. 37-48.
14. Goodwin, C. M., S. Xu, and J. Munger, Stealing the Keys to the Kitchen: Viral Manipulation of the Host Cell Metabolic Network. Trends Microbiol, 2015. 23(12): p. 789-98.
15. Tam, V. C., et al., Lipidomic profiling of influenza infection identifies mediators that induce and resolve inflammation. Cell, 2013. 154(1): p. 213-27.
16. Dimitrov, D. S., Virus entry: molecular mechanisms and biomedical applications. Nat Rev Microbiol, 2004. 2(2): p. 109-22.
17. Altan-Bonnet, N., Lipid Tales of Viral Replication and Transmission. Trends Cell Biol, 2017. 27(3): p. 201-213.
18. Lorizate, M. and H. G. Krausslich, Role of lipids in virus replication. Cold Spring Harb Perspect Biol, 2011. 3(10): p. a004820.
19. Horton, J. D., J. L. Goldstein, and M. S. Brown, SREBPs: activators of the complete program of cholesterol and fatty acid synthesis in the liver. J Clin Invest, 2002. 109(9): p. 1125-31.
20. Sheahan, T. P., et al., Broad-spectrum antiviral GS-5734 inhibits both epidemic and zoonotic coronaviruses. Sci Transl Med, 2017. 9(396).
21. Furuta, Y., et al., Favipiravir (T-705), a novel viral RNA polymerase inhibitor. Antiviral Res, 2013. 100(2): p. 446-54.

22. Qian, X., et al., Brain-Region-Specific Organoids Using Mini-bioreactors for Modeling ZIKV Exposure. Cell, 2016. 165(5): p. 1238-1254.
23. Zhou, J., et al., Human intestinal tract serves as an alternative infection route for Middle East respiratory syndrome coronavirus. Sci Adv, 2017. 3(11): p. eaao4966.
24. Di Paolo, G. and T. W. Kim, Linking lipids to Alzheimer's disease: cholesterol and beyond. Nat Rev Neurosci, 2011. 12(5): p. 284-96.
25. Noguchi, Y., et al., Ketogenic essential amino acids modulate lipid synthetic pathways and prevent hepatic steatosis in mice. PLoS One, 2010. 5(8): p. e12057.
26. Lands, W. E., Stories about acyl chains. Biochim Biophys Acta, 2000. 1483(1): p. 1-14.
27. Goldstein, J. L., R. A. DeBose-Boyd, and M. S. Brown, Protein sensors for membrane sterols. Cell, 2006. 124(1): p. 35-46.
28. Tang, J. J., et al., Inhibition of SREBP by a small molecule, betulin, improves hyperlipidemia and insulin resistance and reduces atherosclerotic plaques. Cell Metab, 2011. 13(1): p. 44-56.
29. Magana, M. M. and T. F. Osborne, Two tandem binding sites for sterol regulatory element binding proteins are required for sterol regulation of fatty-acid synthase promoter. J Biol Chem, 1996. 271(51): p. 32689-94.
30. Parraga, A., et al., Co-crystal structure of sterol regulatory element binding protein 1a at 2.3 A resolution. Structure, 1998. 6(5): p. 661-72.
31. Lee, S. J., et al., The structure of importin-beta bound to SREBP-2: nuclear import of a transcription factor. Science, 2003. 302(5650): p. 1571-5.
32. Dooley, K. A., S. Millinder, and T. F. Osborne, Sterol regulation of 3-hydroxy-3-methylglutaryl-coenzyme A synthase gene through a direct interaction between sterol regulatory element binding protein and the trimeric CCAAT-binding factor/nuclear factor Y. J Biol Chem, 1998. 273(3): p. 1349-56.
33. Kim, J. B., et al., Nutritional and insulin regulation of fatty acid synthetase and leptin gene expression through ADD1/SREBP1. J Clin Invest, 1998. 101(1): p. 1-9.
34. Veit, M., Palmitoylation of virus proteins. Biol Cell, 2012. 104(9): p. 493-515.
35. Veit, M., M. V. Serebryakova, and L. V. Kordyukova, Palmitoylation of influenza virus proteins. Biochem Soc Trans, 2013. 41(1): p. 50-5.
36. Webb, Y., L. Hermida-Matsumoto, and M. D. Resh, Inhibition of protein palmitoylation, raft localization, and T cell signaling by 2-bromopalmitate and polyunsaturated fatty acids. J Biol Chem, 2000. 275(1): p. 261-70.
37. Munger, J., et al., Systems-level metabolic flux profiling identifies fatty acid synthesis as a target for antiviral therapy. Nat Biotechnol, 2008. 26(10): p. 1179-86.
38. Heaton, N. S., et al., Dengue virus nonstructural protein 3 redistributes fatty acid synthase to sites of viral replication and increases cellular fatty acid synthesis. Proc Natl Acad Sci USA, 2010. 107(40): p. 17345-50.
39. Greseth, M. D. and P. Traktman, De novo fatty acid biosynthesis contributes significantly to establishment of a bioenergetically favorable environment for vaccinia virus infection. PLoS Pathog, 2014. 10(3): p. e1004021.
40. Mitchell, D. A., et al., Protein palmitoylation by a family of DHHC protein S-acyltransferases. J Lipid Res, 2006. 47(6): p. 1118-27.
41. Veit, M. and S. Siche, S-acylation of influenza virus proteins: Are enzymes for fatty acid attachment promising drug targets? Vaccine, 2015. 33(49): p. 7002-7.
42. Shimano, H., et al., Elevated levels of SREBP-2 and cholesterol synthesis in livers of mice homozygous for a targeted disruption of the SREBP-1 gene. J Clin Invest, 1997. 100(8): p. 2115-24.
43. Arafa, H. M., et al., Selective agonists of retinoic acid receptors: comparative toxicokinetics and embryonic exposure. Arch Toxicol, 2000. 73(10-11): p. 547-56.
44. Miwako, I. and H. Kagechika, Tamibarotene. Drugs Today (Barc), 2007. 43(8): p. 563-8.
45. Zhou, J., et al., Active replication of Middle East respiratory syndrome coronavirus and aberrant induction of inflammatory cytokines and chemokines in human macrophages: implications for pathogenesis. J Infect Dis, 2014. 209(9): p. 1331-42.
46. Kao, R. Y., et al., Identification of influenza A nucleoprotein as an antiviral target. Nat Biotechnol, 2010. 28(6): p. 600-5.
47. Zheng, B. J., et al., Delayed antiviral plus immunomodulator treatment still reduces mortality in mice infected by high inoculum of influenza A/H5N1 virus. Proc Natl Acad Sci USA, 2008. 105(23): p. 8091-6.
48. Chu, H., et al., Middle East Respiratory Syndrome Coronavirus Efficiently Infects Human Primary T Lymphocytes and Activates the Extrinsic and Intrinsic Apoptosis Pathways. J Infect Dis, 2016. 213(6): p. 904-14.
49. Chan, J. F., et al., Novel antiviral activity and mechanism of bromocriptine as a Zika virus NS2B-NS3 protease inhibitor. Antiviral Res, 2017. 141: p. 29-37.
50. Yuan, S., et al., A novel small-molecule compound disrupts influenza A virus PB2 cap-binding and inhibits viral replication. J Antimicrob Chemother, 2016.
51. Yuan, S., et al., Identification of a small-molecule inhibitor of influenza virus via disrupting the subunits interaction of the viral polymerase. Antiviral Res, 2016. 125: p. 34-42.
52. Chan, C. M., et al., Carcinoembryonic Antigen-Related Cell Adhesion Molecule 5 Is an Important Surface Attachment Factor That Facilitates Entry of Middle East Respiratory Syndrome Coronavirus. J Virol, 2016. 90(20): p. 9114-27.
53. Mortazavi, A., et al., Mapping and quantifying mammalian transcriptomes by RNA-Seq. Nat Methods, 2008. 5(7): p. 621-8.
54. Kim, D., B. Langmead, and S. L. Salzberg, HISAT: a fast spliced aligner with low memory requirements. Nat Methods, 2015. 12(4): p. 357-60.
55. Langmead, B., et al., Ultrafast and memory-efficient alignment of short DNA sequences to the human genome. Genome Biol, 2009. 10(3): p. R25.
56. Burnum-Johnson, K. E., et al., MPLEx: a method for simultaneous pathogen inactivation and extraction of samples for multi-omics profiling. Analyst, 2017. 142(3): p. 442-448.
57. de Wilde, A. H., et al., MERS-coronavirus replication induces severe in vitro cytopathology and is strongly inhibited by cyclosporin A or interferon-alpha treatment. J Gen Virol, 2013. 94(Pt 8): p. 1749-60.
58. Yang, J., et al., The I-TASSER Suite: protein structure and function prediction. Nat Methods, 2015. 12(1): p. 7-8.
59. Sastry, G. M., et al., Protein and ligand preparation: parameters, protocols, and influence on virtual screening enrichments. J Comput Aided Mol Des, 2013. 27(3): p. 221-34.
60. Kim, S., et al., PubChem Substance and Compound databases. Nucleic Acids Res, 2016. 44(D1): p. D1202-13.
61. Stroganov, O. V., et al., Lead finder: an approach to improve accuracy of protein-ligand docking, binding energy estimation, and virtual screening. J Chem Inf Model, 2008. 48(12): p. 2371-85.

What is claimed is:

1. A method of treating a viral infection, comprising: administering to a subject in need thereof, an effective amount of a compound AM580, having the structure:

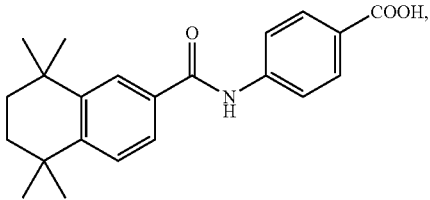 [SMILES: CC1(C)CCC(C)(C)c2cc(C(=O)Nc3ccc(C(=O)O)cc3)ccc21]

wherein the viral infection is caused by a virus selected from the group consisting of MERS-CoV, SARS-CoV, Zika virus, Influenza A virus, Human Adenovirus, and Enterovirus.

2. The method of claim 1, wherein the compound is administered in combination with a pharmaceutically active compound.

3. The method of claim 2, wherein the pharmaceutically active compound is selected from the group consisting of an anti-viral compound, an anti-inflammatory compound, an analgesic compound, an anti-emetic, and an antibiotic.

4. A method of reducing an inflammatory response associated with a viral infection, comprising administering to a subject in need thereof, an effective amount of the compound AM580, having the structure:

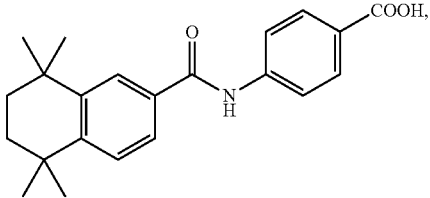 [SMILES: CC1(C)CCC(C)(C)c2cc(C(=O)Nc3ccc(C(=O)O)cc3)ccc21]

wherein the viral infection is caused by a virus selected from the group consisting of MERS-CoV, SARS-CoV, Zika virus, Influenza A virus, Human Adenovirus, and Enterovirus.

5. The method of claim 4, wherein the compound reduces interstitial inflammation or alveolar damage.

6. The method of claim 4, wherein the compound reduces viral induced activation of a pro-inflammatory cytokine.

7. The method of claim 6, wherein the pro-inflammatory cytokine is selected from the group consisting of TNFα, IL-1β, IL-6, and IL-8.

8. The method of claim 4, wherein the compound is administered in combination with a pharmaceutically active compound.

9. The method of claim 1, wherein the compound is administered in a pharmaceutically acceptable carrier.

10. The method of claim 4, wherein the compound is administered in a pharmaceutically acceptable carrier.

11. The method of claim 1, wherein the effective amount of the compound ranges from 1 μg/kg body weight of the subject to 100 mg/kg body weight of the subject.

12. The method of claim 1, wherein the viral infection is caused by Influenza A (H1N1) pdm09, Influenza virus A (H5N1), or Influenza virus A (H7N9).

13. The method of claim 1, wherein the viral infection is caused by Human Adenovirus 5.

14. The method of claim 1, wherein the effective amount of the compound ranges from 5 μM to 100 μM.

* * * * *

SEQUENCE LISTING

<160> NUMBER OF SEQ ID NOS: 1

<210> SEQ ID NO 1
<211> LENGTH: 80
<212> TYPE: PRT
<213> ORGANISM: Homo sapiens

<400> SEQUENCE: 1

Gly Glu Lys Arg Thr Ala His Asn Ala Ile Glu Lys Arg Tyr Arg Ser
1               5                   10                  15

Ser Ile Asn Asp Lys Ile Ile Glu Leu Lys Asp Leu Val Val Gly Thr
            20                  25                  30

Glu Ala Lys Leu Asn Lys Ser Ala Val Leu Arg Lys Ala Ile Asp Tyr
        35                  40                  45

Ile Arg Phe Leu Gln His Ser Asn Gln Lys Leu Lys Gln Glu Asn Leu
    50                  55                  60

Ser Leu Arg Thr Ala Val His Lys Ser Lys Ser Leu Lys Asp Leu Val
65                  70                  75                  80